(12) United States Patent
Nguyen et al.

(10) Patent No.: US 11,615,873 B2
(45) Date of Patent: Mar. 28, 2023

(54) DEEP LEARNING BASED DOSED PREDICTION FOR TREATMENT PLANNING AND QUALITY ASSURANCE IN RADIATION THERAPY

(71) Applicant: The Board of Regents of The University of Texas System, Austin, TX (US)

(72) Inventors: Dan Nguyen, Dallas, TX (US); Steve Jiang, Southlake, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 734 days.

(21) Appl. No.: 16/558,681

(22) Filed: Sep. 3, 2019

(65) Prior Publication Data
US 2020/0075148 A1    Mar. 5, 2020

Related U.S. Application Data

(60) Provisional application No. 62/725,622, filed on Aug. 31, 2018.

(51) Int. Cl.
*G16H 20/10*    (2018.01)
*G06N 5/04*    (2006.01)
(Continued)

(52) U.S. Cl.
CPC ............. *G16H 20/10* (2018.01); *G06N 3/04* (2013.01); *G06N 3/08* (2013.01); *G06N 5/04* (2013.01)

(58) Field of Classification Search
None
See application file for complete search history.

(56) References Cited

U.S. PATENT DOCUMENTS

| | | | |
|---|---|---|---|
| 2013/0197878 A1* | 8/2013 | Fiege | G06F 30/20 |
| | | | 703/2 |
| 2015/0367145 A1 | 12/2015 | Sjolund et al. | |
| 2018/0043182 A1* | 2/2018 | Wu | A61N 5/1039 |

OTHER PUBLICATIONS

Mahmood, et al., "Automated treatment planning in radiation therapy using generative adversarial networks", Proceedings of Machine Learning Research, Jul. 17, 2018, 15 pages.

(Continued)

*Primary Examiner* — Michael W Kahelin
*Assistant Examiner* — Naveed R. Kolia
(74) *Attorney, Agent, or Firm* — DLA Piper LLP (US)

(57) ABSTRACT

A method and system for generating a treatment plan are disclosed herein. A computing system receives a plurality of dose volume histograms for a plurality of patients and a plurality of volumetric dose distributions corresponding to the plurality of dose volume histograms. The computing system generates a volumetric dose prediction model using a neural network by learning, by the neural network, a relationship between a plurality of dose volume histograms for the plurality of patients and the corresponding plurality of volumetric dose distributions. The computing system receives a candidate dose volume histogram for a target patient. The computing system infers, via the volumetric dose prediction module, a volumetric dose prediction distribution matching the candidate dose volume histogram. The computing system generates a recommendation based on the inferred volumetric dose prediction distribution.

20 Claims, 57 Drawing Sheets
(55 of 57 Drawing Sheet(s) Filed in Color)

(51) Int. Cl.
G06N 3/08 (2006.01)
G06N 3/04 (2006.01)

(56) References Cited

OTHER PUBLICATIONS

Babier, et al., "Knowledge-based automated planning for oropharyngeal cancer", Medical physics, vol. 45, Jul. 2018, pp. 2875-2883.
Nguyen, et al., "3D radiotherapy dose prediction on head and neck cancer patients with a hierarchically densely connected U-net deep learning architecture", Physics in Medicine and Biology, 2019, 26 pages.
Nguyen, et al., "Generating Pareto optimal dose distributions for radiation therapy treatment planning", arXiv preprint arXiv:1906.04778, 2019, 9 pages.
Goodfellow, et al., "Generative Adversarial Nets", Advances in neural information processing systems, 2014, pp. 2672-2680.
Muralidhar, et al., "Incorporating Prior Domain Knowledge into Deep Neural Networks", 2018 IEEE International Conference on Big Data (Big Data), Dec. 10-13, 2018, 10 pages.
Mao, et al., "Least Squares Generative Adversarial Networks", Proceedings of the IEEE International Conference on Computer Vision, 2017, pp. 2794-2802.
Ronneberger, et al., "U-net: Convolutional networks for biomedical image segmentation", International Conference on Medical image computing and computer-assisted intervention, May 18, 2015, pp. 234-241.
LeCun, et al., "Gradient-based learning applied to document recognition", Proceedings of the IEEE, Nov. 1998, 46 pages.
LeCun, et al., "Object recognition with gradient-based learning", Shape, contour and grouping in computer vision, Springer, 1999, 28 pages.
Mirza, et al., "Conditional generative adversarial nets", arXiv preprint arXiv:1411.1784, Nov. 6, 2014, 7 pages.
Wu, et al., "Group normalization", Proceedings of the European Conference on Computer Vision (ECCV), 2018, 17 pages.
Ioffe, et al., "Batch normalization: Accelerating deep network training by reducing internal covariate shift", International Conference on Machine Learning, Mar. 2, 2015, 11 pages.
Nguyen, et al., "Integral dose investigation of non-coplanar treatment beam geometries in radiotherapy", Medical physics, vol. 41, Jan. 2014, 8 pages.
Reese, et al., "Integral dose conservation in radiotherapy", Medical physics, vol. 36.3, Mar. 2009, pp. 734-740.
Aoyama, et al., "Integral radiation dose to normal structures with conformal external beam radiation", International Journal of Radiation Oncology Biology Physics, vol. 64.3, Mar. 2006, pp. 962-967.
D'Souza, et al., "Nontumor integral dose variation in conventional radiotherapy treatment planning", Medical physics, vol. 30.8, Aug. 2003, pp. 2065-2071.
Jahn, "Scalarization in multi objective optimization", Mathematics of multi objective optimization, Springer, 1985, pp. 45-88.
Chambolle, et al., "A first-order primal-dual algorithm for convex problems with applications to imaging", Journal of mathematical imaging and vision, Jun. 9, 2010, hal-00490826, 50 pages.
Van't Riet, et al., "A conformation number to quantify the degree of conformality in brachytherapy and external beam irradiation: application to the prostate", International Journal of Radiation Oncology Biology Physics, vol. 37.3, 1997, Elsevier Science Inc., pp. 731-736.
Grégoire, et al., "State of the art on dose prescription, reporting and recording in intensity-modulated radiation therapy (ICRU report No. 83)", Elsevier Masson SAS, 2011, pp. 555-559.
Savitzky, et al., "Smoothing and differentiation of data by simplified least squares procedures", Analytical chemistry, vol. 36.8, Jul. 1964, pp. 1627-1639.
Boyd, et al., "Convex optimization" Cambridge university press, Mar. 15, 1999, 216 pages.
Nguyen, et al., "Incorporating human and learned domain knowledge into training deep neural networks: A differentiable dose volume histogram and adversarial inspired framework for generating Pareto optimal dose distributions in radiation therapy", arXiv preprint arXiv:1908.05874, Aug. 16, 2019, 21 pages.
Brahme, "Optimization of stationary and moving beam radiation therapy techniques", Radiotherapy and Oncology, vol. 12, 1988, pp. 129-140.
Bortfeld, et al., "Methods of image reconstruction from projections applied to conformation radiotherapy", Physics in Medicine & Biology, IPEM, vol. 35, 1990, pp. 1423-1434.
Bortfeld, et al., "X-ray field compensation with multileaf collimators", International Journal of Radiation Oncology Biology, Physics, Elsevier Science LTD, vol. 28, 1994, pp. 723-730.
Webb, "Optimisation of conformal radiotherapy dose distribution by simulated annealing", Physics in Medicine & Biology, IPEM, vol. 34, 1989, pp. 1349-1370.
Convery, et al., "The generation of intensity-modulated fields for conformal radiotherapy by dynamic collimation", Physics in Medicine and Biology, vol. 37, 1992, pp. 1359-1374.
Xia, et al., "Multileaf collimator leaf sequencing algorithm for intensity modulated beams with multiple static segments", Medical Physics, vol. 25, Jun. 1, 1998, pp. 1424-1434.
Keller-Reichenbecher, et al., "Intensity modulation with the "step and shoot" technique using a commercial MLC: A planning study", International Journal of Radiation Oncology Biology, Physics, Elsevier Science Inc., vol. 45.5, 1999, pp. 1315-1324.
Yu, "Intensity-modulated arc therapy with dynamic multileaf collimation: an alternative to tomotherapy", Physics in Medicine and Biology, vol. 40, 1995, pp. 1435-1449.
Otto, "Volumetric modulated arc therapy: IMRT in a single gantry arc", Medical physics, vol. 35, Jan. 2008, pp. 310-317.
Palma, et al., "Volumetric modulated arc therapy for delivery of prostate radiotherapy: comparison with intensity-modulated radiotherapy and three-dimensional conformal radiotherapy", Elsevier Inc., International Journal of Radiation Oncology Biology Physics, vol. 72, No. 4, 2008, pp. 996-1001.
Shaffer, et al., "Volumetric modulated Arc therapy and conventional intensity-modulated radiotherapy for simultaneous maximal intraprostatic boost: a planning comparison study", Clinical oncology, vol. 21, 2009, pp. 401-407.
Shaffer, et al., "A comparison of volumetric modulated arc therapy and conventional intensity-modulated radiotherapy for frontal and temporal high-grade gliomas", International Journal of Radiation Oncology Biology Physics, Elsevier Inc., vol. 76.4, 2010, pp. 1177-1184.
Crooks, et al., "Aperture modulated arc therapy", Physics in Medicine and Biology, Institute of Physics Publishing, vol. 48.10, 2003, pp. 1333-1344.
Earl, et al., "Inverse planning for intensity-modulated arc therapy using direct aperture optimization", Physics in Medicine and Biology, 48, 2003, pp. 1075-1089.
Cao, et al., "A generalized inverse planning tool for volumetric-modulated arc therapy", Physics in Medicine and Biology, vol. 54, 2009, pp. 6725-6738.
Penfold, et al., "Sparsity constrained split feasibility for dose-volume constraints in inverse planning of intensity-modulated photon or proton therapy", Physics in Medicine and Biology, 62, 2017, 35 pages.
Craft, et al., "Approximating convex Pareto surfaces in multiobjective radiotherapy planning", Medical physics, vol. 33, Sep. 2006, pp. 3399-3407.
Craft, et al., "Improved planning time and plan quality through multicriteria optimization for intensity-modulated radiotherapy", International Journal of Radiation Oncology Biology Physics, vol. 82, 2012, pp. e83-e90.
Monz, et al., "Pareto navigation-algorithmic foundation of interactive multi-criteria IMRT planning", Physics in Medicine and Biology, IPEM, vol. 53, 2008, pp. 985-998.
Nguyen, et al., "Dose domain regularization of MLC leaf patterns for highly complex IMRT plans", Medical physics, vol. 42.4, Apr. 2015, pp. 1858-1870.

(56) References Cited

OTHER PUBLICATIONS

Nguyen, et al., "Computerized triplet beam orientation optimization for MRI-guided Co-60 radiotherapy", Medical physics, vol. 43, Oct. 2016, pp. 5667-5675.

Nguyen, et al., "A comprehensive formulation for volumetric modulated arc therapy planning", Medical physics, vol. 43, Jul. 2016, pp. 4263-4272.

Nguyen, et al., "Deterministic direct aperture optimization using multiphase piecewise constant segmentation", Medical physics, vol. 44, Nov. 2017, pp. 5596-5609.

O'Connor, et al., "Fraction-variant beam orientation optimization for non-coplanar IMRT", Physics in Medicine and Biology, vol. 63, 045015, 2018, 41 pages.

Long, et al., "Threshold-driven optimization for reference-based auto-planning", Physics in Medicine and Biology, IPEM, vol. 63.4, 2018, 8 pages.

Zarepisheh, et al., "A DVH-guided IMRT optimization algorithm for automatic treatment planning and adaptive radiotherapy replanning", Medical physics, vol. 41, No. 6, Jun. 2014, 14 pages.

Zhu, et al., "A planning quality evaluation tool for prostate adaptive IMRT based on machine learning", Medical physics, vol. 38.2, Jan. 11, 2011, pp. 719-726.

Appenzoller, et al., "Predicting dose-volume histograms for organs-at-risk in IMRT planning", International Journal of Radiation Oncology Biology Physics, vol. 39, Dec. 2012, 2 pages.

Wu, et al., "Improved robotic stereotactic body radiation therapy plan quality and planning efficacy for organ-confined prostate cancer utilizing overlap-volume histogram-driven planning methodology", Radiotherapy and Oncology, Elsevier Ltd., vol. 112.2, 2014, pp. 221-226.

Shiraishi, et al., "Knowledge-based prediction of plan quality metrics in intracranial stereotactic radiosurgery", Medical physics, vol. 42.2, Feb. 2015, pp. 908-917.

Moore, et al., "Experience-based quality control of clinical intensity-modulated radiotherapy planning", International Journal of Radiation Oncology Biology Physics, vol. 81.2, Elsevier Inc., 2011, pp. 545-551.

Shiraishi, et al., "Knowledge-based prediction of three-dimensional dose distributions for external beam radiotherapy", Medical physics, vol. 43.1, Dec. 6, 2015, pp. 378-387.

Wu, et al., "Patient geometry-driven information retrieval for IMRT treatment plan quality control", Medical physics, vol. 36, Dec. 2009, pp. 5497-5505.

Wu, et al., "Data-driven approach to generating achievable dose-volume histogram objectives in intensity-modulated radiotherapy planning", International Journal of Radiation Oncology Biology Physics, vol. 79, 2010, 7 pages.

Wu, et al., "Using overlap volume histogram and IMRT plan data to guide and automate VMAT planning: a head-and-neck case study", Medical physics, vol. 40, Feb. 2013, 7 pages.

Tran, et al., "Predicting liver SBRT eligibility and plan quality for VMAT and 4π plans", Radiation Oncology, vol. 12:70, 2017, 9 pages.

Yuan, et al., "Quantitative analysis of the factors which affect the interpatient organ-at-risk dose sparing variation in IMRT plans", Medical physics, vol. 39.11, Nov. 2012, pp. 6868-6878.

Lian, et al., "Modeling the dosimetry of organ-at-risk in head and neck IMRT planning: an intertechnique and interinstitutional study", Medical physics, vol. 40, Dec. 2013, 9 pages.

Folkerts, et al., "SU-G-TeP1-09: Modality-Specific Dose Gradient Modeling for Prostate IMRT Using Spherical Distance Maps of PTV and Isodose Contours", Medical physics, vol. 43.6, Jun. 7, 2016, pp. 3653-3654.

Good, et al., "A knowledge-based approach to improving and homogenizing intensity modulated radiation therapy planning quality among treatment centers: an example application to prostate cancer planning", International Journal ol Radiation Oncology Biology Physics, vol. 87.1, Mar. 11, 2013, pp. 176-181.

Folkerts, et al., "Knowledge-based automatic treatment planning for prostate IMRT using 3-dimensional dose prediction and threshold-based optimization", Medical Physics, vol. 44, Jun. 2017.

Krizhevsky, et al., "ImageNet classification with deep convolutional neural networks", Advances in neural information processing systems, 2012, 9 pages.

Girshick, et al., "Rich feature hierarchies for accurate object detection and semantic segmentation", Proceedings of the IEEE conference on computer vision and pattern recognition, 2014, 8 pages.

Simonyan, et al., "Very deep convolutional networks for large-scale image recognition", ICLR, Apr. 10, 2015, 14 pages.

LeCun, et al., "Backpropagation applied to handwritten zip code recognition", Neural computation, 1989, pp. 541-551.

Nguyen, et al., "A feasibility study for predicting optimal radiation therapy dose distributions of prostate cancer patients from patient anatomy using deep learning", Scientific reports, Jan. 31, 2019, 10 pages.

Kearney, et al., "DoseNet: a volumetric dose prediction algorithm using 3D fully-convolutional neural networks", Physics in Medicine and Biology, IPEM, 2018, 12 pages.

Barragán-Montero, et al., "Three-Dimensional Dose Prediction for Lung IMRT Patients with Deep Neural Networks: Robust Learning from Heterogeneous Beam Configurations", Medical physics, 2019, 23 pages.

Fan, et al., "Automatic treatment planning based on three-dimensional dose distribution predicted from deep learning technique", Medical physics, vol. 46.1, Jan. 2019, pp. 370-381.

Babier, et al., "Knowledge-based automated planning with three-dimensional generative adversarial networks", arXiv preprint arXiv:1812.09309, Dec. 21, 2018, 15 pages.

PCT International Application No. PCT/US2019/049302, The International Search Report and the Written Opinion of the International Searching Authority, dated Nov. 20, 2019, 7 pages.

\* cited by examiner

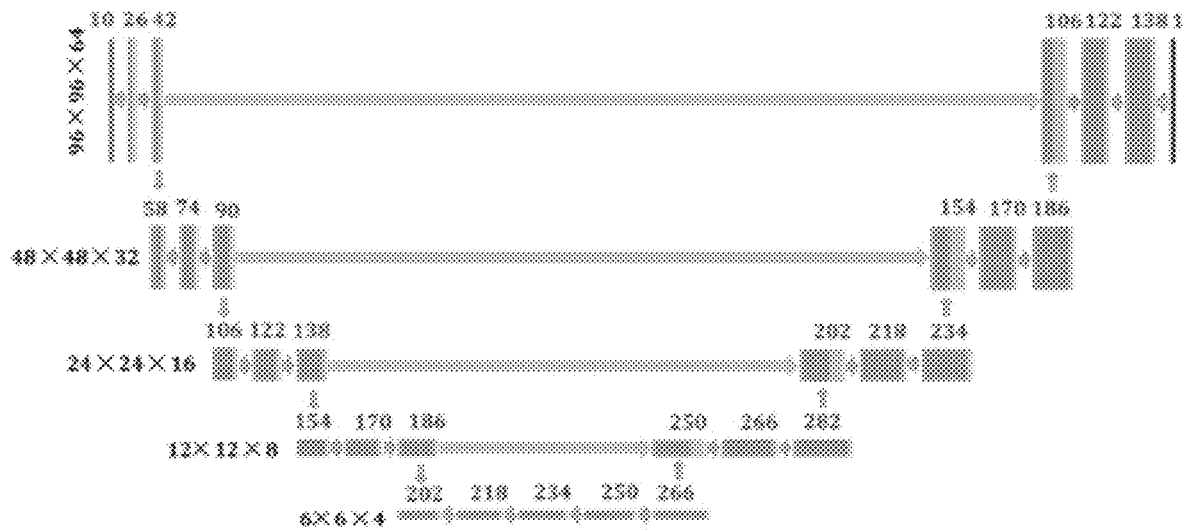
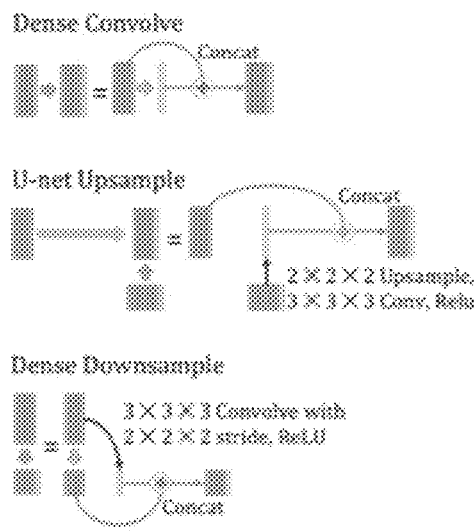
FIG. 18

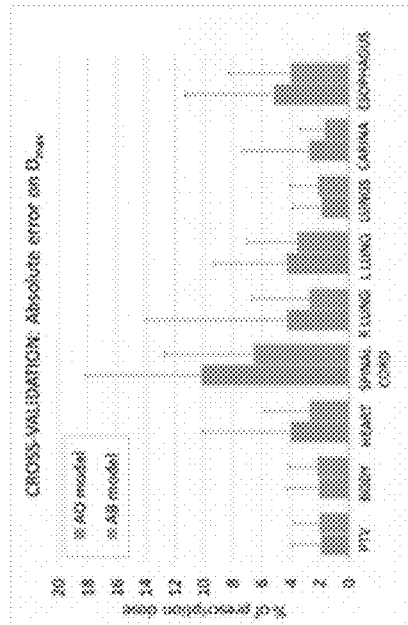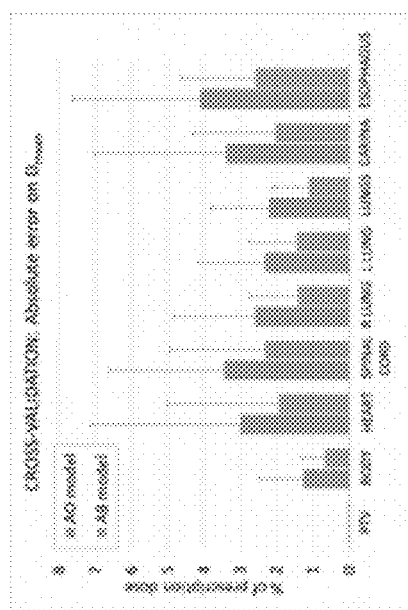
FIG. 21

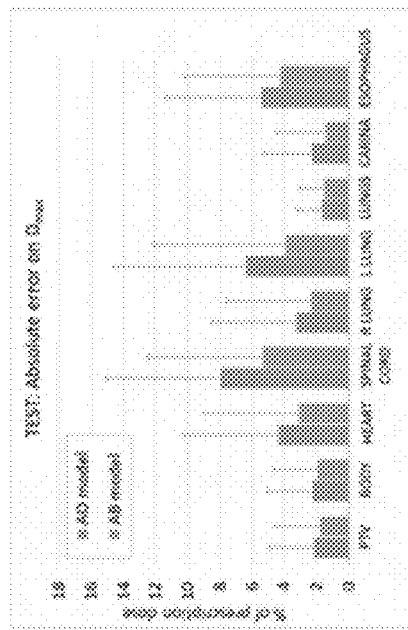
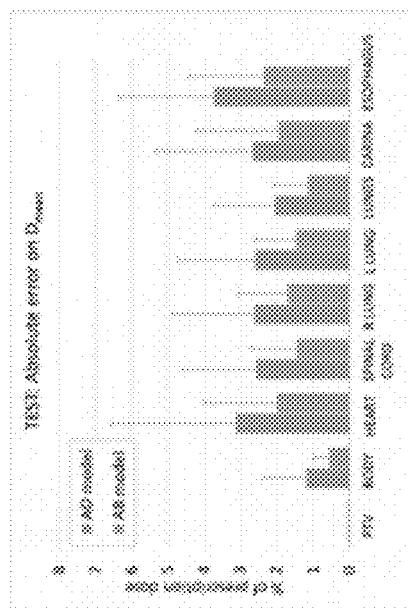
FIG. 22

DEEP LEARNING BASED DOSED PREDICTION FOR TREATMENT PLANNING AND QUALITY ASSURANCE IN RADIATION THERAPY

CROSS-REFERENCE TO RELATED APPLICATION

This application claims priority from U.S. Provisional Application Ser. No. 62/725,622, filed Aug. 31, 2018, which is hereby incorporated by reference in its entirety.

BACKGROUND

Radiation therapy is one of the major cancer therapy modalities. About two-thirds of cancer patients in the United States receive radiation therapy either alone or in conjunction with surgery, chemotherapy, immunotherapy, etc. Treatment planning, where an optimal treatment strategy is designed for each individual patient and executed for the whole treatment course, is analogous to the design of a blueprint for building construction. If a treatment plan is poorly designed, the desired treatment outcome cannot be achieved, no matter how well other components of radiation therapy are designed. In the current treatment planning workflow, a treatment planner works towards a good quality plan in a trial-and-error fashion using a commercial treatment planning system. In the meanwhile, many rounds of consultation between the planner and physician are often needed to reach a plan of physician's satisfaction for a particular patient, mainly due to the fact that medicine, to some degree, is still an art and physician's preferences for a particular patient can hardly be quantified and precisely conveyed to the planner. Consequently, planning time can take up to a week for complex cases and plan quality may be poor and can vary significantly due to the varying levels of physician and planner's skills and physician-planner cooperation.

Over the last a few years, artificial intelligence (AI) has made colossal advancements, particularly in the areas of imaging, vision, and decision making. AI technologies have great potential to revolutionize treatment planning and quality assurance (QA) for treatment delivery. Treatment planning, similar to many other health care issues, consists of two major aspects: 1) commonality (overall treatment strategies are similar for patients with similar medical conditions), and 2) individuality (population based overall treatment strategy needs to be fine-tuned for some patients). By exploiting the commonality through deep supervised learning, a system may develop a treatment plan as well as those for previously treated similar patients. The individuality could be actualized by the development of models that are capable of navigating the tradeoffs space between organs-at-risk and the target, which is known as the Pareto surface of treatment plans. This will allow for physicians to quickly tune the plan to one that is individualized to the patient. Treatment delivery also consists of two major goals: 1) accurate delivery and 2) patient safety. This process can be made more accurate and efficient through the use of deep learning technologies, by incorporating fast dose prediction-based deep learning computer systems. These AI technologies would revolutionize treatment planning process, leading to the efficient generation of consistently high quality treatment plans, irrespective of human skills, experiences, communications, etc.

SUMMARY

A computer system for use in the treatment planning and QA for treatment delivery is disclosed herein. For example, disclosed herein is a fast system that includes neural network architectures for the volumetric prediction of the distribution for patients of various cancer sites, including head-and-neck cancer, lung cancer, and prostate cancer. The output of these systems can then be utilized as either a guidance tool for the clinicians or as part of an automated system, to improve the planning efficiency, planning quality, and quality assurance efficiency and accuracy. For dose prediction, the computer system is capable of prediction dose distributions of two categories: 1) clinical dose prediction: the system can predict dose that is of clinically acceptable quality for the physician, and 2) Pareto optimal dose prediction: the system can navigate the tradeoff space between sparing dose to organs-at-risk and maintaining coverage of the prescription dose to the tumor or target. For clinical dose prediction, each cancer site posed different challenges that each model was trained to address. Head-and-neck cancer patients have the most complex geometry and relationship between the patient's organs-at-risk and the tumor for any cancer site. The system was trained to simultaneously incorporate the relationship of over 20 different structures. For lung cancer, the treatment beam geometry varies wildly among different patients. Here the system learned to incorporate any beam geometry and generate a clinically acceptable volumetric dose distribution to match. For the Pareto optimal dose prediction, the computing system was made to handle different use cases in the clinic workflow. One computing model is developed to take in the desired clinical constraints, in the form of a metric call dose volume histograms (DVH), and then predict the volumetric dose distribution to match the metric, while maintaining realistic radiation doses. The other model is developed for real-time navigation of the tradeoff space between sparing dose to organs-at-risk and maintaining coverage of the prescription dose to the tumor or target. This is done by allowing a clinician to tune the importance weighting of structures and receive real-time feedback in the form of a matching volumetric dose distribution. In addition, the computing system includes human and learned domain knowledge, for improved accuracy and precision in the dose prediction computing system. Human domain knowledge are metrics that developed and used from human experts, such as physicians. Learned domain knowledge is allowing for the AI computing system to learn its own metrics and reasoning for improving its own performance. The system applies this concept in the form of reforming the DVH metric as an objective (human component) and combining this with a deep learning technique called adversarial learning (AI component).

In some embodiments, a method for generating a treatment plan is disclosed herein. The computing system receives a plurality of dose volume histograms for a plurality of patients and a plurality of volumetric dose distributions corresponding to the plurality of dose volume histograms. The computing system generates a volumetric dose prediction model using a neural network by learning, by the neural network, a relationship between a plurality of dose volume histograms for the plurality of patients and the corresponding plurality of volumetric dose distributions. The computing system receives a candidate dose volume histogram for a target patient. The computing system infers, via the volumetric dose prediction module, a volumetric dose prediction distribution matching the candidate dose volume histogram. The computing system generates a recommendation based on the inferred volumetric dose prediction distribution.

In some embodiments, a system is disclosed herein. The system includes a processor and a memory. The memory has programming instructions stored thereon, which, when executed by the processor, performs one or more operations. The one or more operations include receiving a plurality of dose volume histograms for a plurality of patients and a plurality of volumetric dose distributions corresponding to the plurality of dose volume histograms. The one or more operations further include generating a volumetric dose prediction model using a neural network by learning, by the neural network, a relationship between a plurality of dose volume histograms for the plurality of patients and the corresponding plurality of volumetric dose distributions. The one or more operations further include receiving a candidate dose volume histogram for a target patient. The one or more operations further include inferring, by the volumetric dose prediction module, a volumetric dose prediction distribution matching the candidate dose volume histogram. The one or more operations further include generating a recommendation based on the inferred volumetric dose prediction distribution.

In some embodiments, a non-transitory computer readable medium is disclosed herein. The non-transitory computer readable medium has instructions stored thereon, which, when executed by a processor, cause the processor to perform an operation. The operation includes receiving, by a computing system, a plurality of dose volume histograms for a plurality of patients and a plurality of volumetric dose distributions corresponding to the plurality of dose volume histograms. The operation further includes generating, by the computing system, a volumetric dose prediction model using a neural network by learning, by the neural network, a relationship between a plurality of dose volume histograms for the plurality of patients and the corresponding plurality of volumetric dose distributions. The operation further includes receiving, by the computing system, a candidate dose volume histogram for a target patient. The operation further includes inferring, by the computing system via the volumetric dose prediction module, a volumetric dose prediction distribution matching the candidate dose volume histogram. The operation further includes generating, by the computing system, a recommendation based on the inferred volumetric dose prediction distribution.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Various objectives, features, and advantages of the disclosed subject matter can be more fully appreciated with reference to the following detailed description of the disclosed subject matter when considered in connection with the following drawings, in which like reference numerals identify like elements.

FIG. 18 is a block diagram illustrating architecture of HD U-net, according to example embodiments.

FIG. 21 are charts illustrating average absolute error on the mean (left) an maximum dose (right) for the predictions versus the clinical dose, according to example embodiments.

FIG. 22 are charts illustrating average absolute error on the mean (left) an maximum dose (right) for the predictions versus the clinical dose, according to example embodiments.

Figure 1:
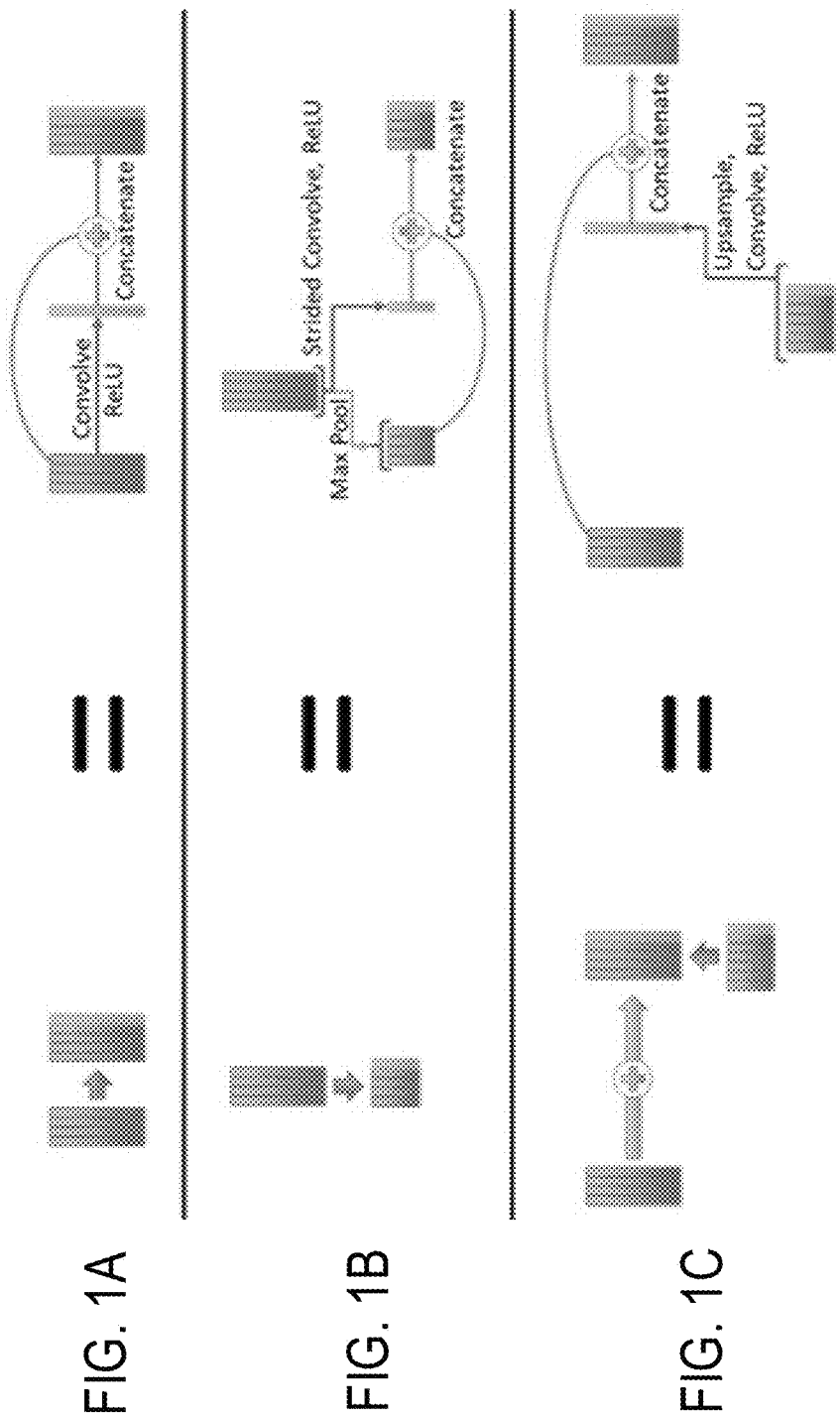
FIG. 1A is a block diagram illustrating a dense convolution in a neural network, according to example embodiments.
FIG. 1B is a block diagram illustrating dense downsampling in a neural network, according to example embodiments.
FIG. 1C is a block diagram illustrating u-net up-sampling in neural network, according to example embodiments.

The drawings are not necessarily to scale, or inclusive of all elements of a system, emphasis instead generally being placed upon illustrating the concepts, structures, and techniques sought to be protected herein.

DETAILED DESCRIPTION

Section I: HEAD AND NECK CANCER PATIENTS The treatment planning process for patients with head and neck (H&N) cancer is regarded as one of the most complicated due to large target volume, multiple prescription dose levels, and many radiation-sensitive critical structures near the target. Treatment planning for this site requires a high level of human expertise and a tremendous amount of effort to produce personalized high quality plans, taking as long as a week, which deteriorates the chances of tumor control and patient survival. To solve this problem, a deep learning-based dose prediction model is disclosed herein. For example, a deep learning-based dose prediction model—Hierarchically Densely Connected U-net—may be based on two network architectures: U-net and DenseNet. This new architecture is able to accurately and efficiently predict the dose distribution, outperforming the other two models (i.e., the Standard U-net and DenseNet) in homogeneity, dose conformity, and dose coverage on the test data. Averaging across all organs at risk, the disclosed model is capable of predicting the organ-at-risk max dose within about 6.3% and mean dose within about 5.1% of the prescription dose on the test data. In comparison, the other models (i.e., the Standard U-net and DenseNet) performed worse, having an averaged organ-at-risk max dose prediction error of about 8.2% and about 9.3%, respectively, and averaged mean dose prediction error of about 6.4% and about 6.8%, respectively. In addition, the disclosed model used about 12 times less trainable parameters than the Standard U-net, and predicted the patient dose about 4 times faster than DenseNet.

I.1: Introduction

Patients with head and neck (H&N) cancer undergoing radiotherapy have typically been treated with intensity modulated radiation therapy (IMRT) (Brahme, 1988; Bortfeld et al., 1990; Bortfeld et al., 1994; Webb, 1989; Convery and Rosenbloom, 1992; Xia and Verhey, 1998; Keller-Reichenbecher et al., 1999) and volume modulated arc therapy (VMAT) (Yu, 1995; Otto, 2008; Palma et al., 2008; Shaffer et al., 2009; Shaffer et al., 2010; Xing, 2003; Earl et al., 2003; Daliang Cao and Muhammad, 2009), which has significantly reduced toxicity (Marta et al., 2014; Toledano et al., 2012; Gupta et al., 2012) and improved quality of life (Rathod et al., 2013; Tribius and Bergelt, 2011), as compared to more conventional methods such as 3D conformal radiotherapy. However, treatment planning for this site is regarded as one of the most complicated due to several aspects, including large planning target volume (PTV) size (Paulino et al., 2005), multiple prescription dose levels that are simultaneously integrated boosted (Studer et al., 2006; Wu et al., 2003), and many radiation-sensitive organs-at-risk (OAR) that are in close proximity to the PTV (Mayo et al.; Kirkpatrick et al.; Deasy et al.; Rancati et al.). Consequently, treatment planning for this site requires a tremendous level of human expertise and effort to produce personalized high quality plans.

In the typical current treatment planning workflow, a treatment planner solves an inverse optimization problem (Oelfke and Bortfeld, 2001), where they adjust a set of hyper-parameters and weightings to control the tradeoffs between clinical objectives. Since the physician preferred plan is largely unknown, the planner meticulously tunes these parameters in a trial-and-error fashion in an attempt to reach an appropriate solution. Many rounds of consultation between the planner and physician occur regarding the plan quality and tradeoffs are discussed. Ultimately, this trial-and-error process in parameter tuning results in hours for a plan to be generated (Craft et al., 2012; Schreiner, 2011; Van Dye et al., 2013), and the iterations of consultation between the physician and planner may extend the treatment planning time up to one week. For aggressive H&N tumors, where tumor volume can double in approximately 30 days, which account for 50% of patients (Jensen et al., 2007), an extended planning time can greatly decrease local tumor control and patient survival (Bese et al.; González Ferreira et al., 2015; Fowler and Lindstrom, 1992; Fein et al., 1996).

In recent years, the field of artificial intelligence (AI) and deep learning has made amazing progress, particularly in the field of computer vision and decision making In 2015, Ronneberger et al. proposed a deep learning architecture for semantic segmentation, known as U-net (Ronneberger et al., 2015). This neural network architecture, a type of convolutional neural network (CNN) (LeCun et al., 1989) that falls under the class fully convolutional networks (FCN) (Long et al., 2015), was capable of incorporating both local and global features to make a pixel-wise prediction. These predictions are commonly done slice-by-slice in 2D. For dose prediction, this 2D-based prediction can inherently cause some errors, particularly in slices at the superior and inferior edges of the PTV, thus leading towards 3D volumetric deep learning models. However, when creating a 3D variant of U-net, the computational expense grows with the dimensionality Tradeoffs have to be made with the 3D version, such as less filters per convolution or max pooling layers. Attempts to combat this for 3D architectures focused on modifying portions of the architecture to be more efficient at propagating information, such as having a ResNet flavor of including skip connections during each block (Milletari et al., 2016; He et al., 2016). With the currently available GPU technologies and memory, the network's performance is sacrificed.

A publication in 2017 by Huang et al. proposed a Densely Connected Convolutional Neural Network, also known as DenseNet (Huang et al., 2017). The publication proposed the novel idea of densely connecting its convolutional maps together to promote feature propagation and reuse, reduce the vanishing gradient issue, and decrease the number of trainable parameters needed. While the term "densely connected" was historically used to described fully connected neural network layers, this publication by Huang et al. had adopted this terminology to describe how the convolutional layers were connected. While requiring more memory to use, the DenseNet was capable of achieving a better performance while having far less parameters in the neural network. For example, accuracy comparable with ResNet was achieved, which had 10 million parameters, using the DenseNet, which had 0.8M parameters. This indicates that DenseNet is far more efficient in feature calculation than existing network architectures. DenseNet, however, while efficient in parameter usage, actually utilizes considerably more GPU RAM, rendering a 3D U-net with fully densely connected convolutional connections infeasible for today's current GPU technologies.

Motivated by a 3D densely connected U-net, but requiring less memory usage, a neural network architecture that combines the essence of these two influential neural network architectures into a network while maintaining a respectable RAM usage (i.e., Hierarchically Densely Connected U-net (HD U-net)) is disclosed herein. The term "hierarchically" is used herein to describe the different levels of resolution in the U-net between each max pooling or upsampling operation. The convolutional layers are densely connected along each hierarchy, but not between hierarchies of the U-net during the upsampling operation. In particular, to the disclosed system and method utilize the global and local information capabilities of U-net and the more efficient feature propagation and reuse of DenseNet. DenseNet alone is not expected to perform well for this task because accurate prediction of dose distribution requires both global and local information. While the feature maps of DenseNet are connected throughout the network, which allows for an efficient feature propagation, the lack of pooling followed by subsequent upsampling procedure, that is found in U-net, limits the network's capability to capture global information. The below assesses the proposed deep learning architecture on its capability to volumetrically predict the dose distribution for patients with H&N cancer, and compare its performance against the two deep learning models from which it was inspired from: U-net and DenseNet. The HD U-net and the 3D variants of U-net and DenseNet can all fit on a 11 GB 1080 Ti GPU for unbiased comparison.

I.2: Methods

I.2(a): Hierarchically Dense U-Net Deep Learning Architecture

In order to give every operation a 'densely connected' flavor, the following were defined.

FIG. 1A is a block diagram illustrating a "dense convolution", according to example embodiments. A dense convolution includes a standard convolution and Rectified Linear Unit (ReLU) operation to calculate a feature set, followed by a concatenation of the previous feature set. Performing this operation back-to-back is equivalent to the densely connected computation in the DenseNet publication.

FIG. 1B is a block diagram illustrating "dense downsampling", according to example embodiments. The "dense downsampling" operation in FIG. 1B may be performed by a strided convolution and ReLU to calculate a new feature set that has half the resolution. The previous feature set is then max pooled and concatenated to the new feature set.

FIG. 1C is a block diagram illustrating "u-net upsampling", according to example embodiments. The "u-net upsampling" operation may include up-sampling, convolution, and ReLU, followed by a concatenation of the feature set on the other side of the "U". This "u-net upsampling" is the same operation used in the standard U-net, with the upsample/convolve combination sometimes replaced with the transposed convolution. For each dense operation, a growth rate can be defined as the number of features added after each dense operation.

Figure 2:
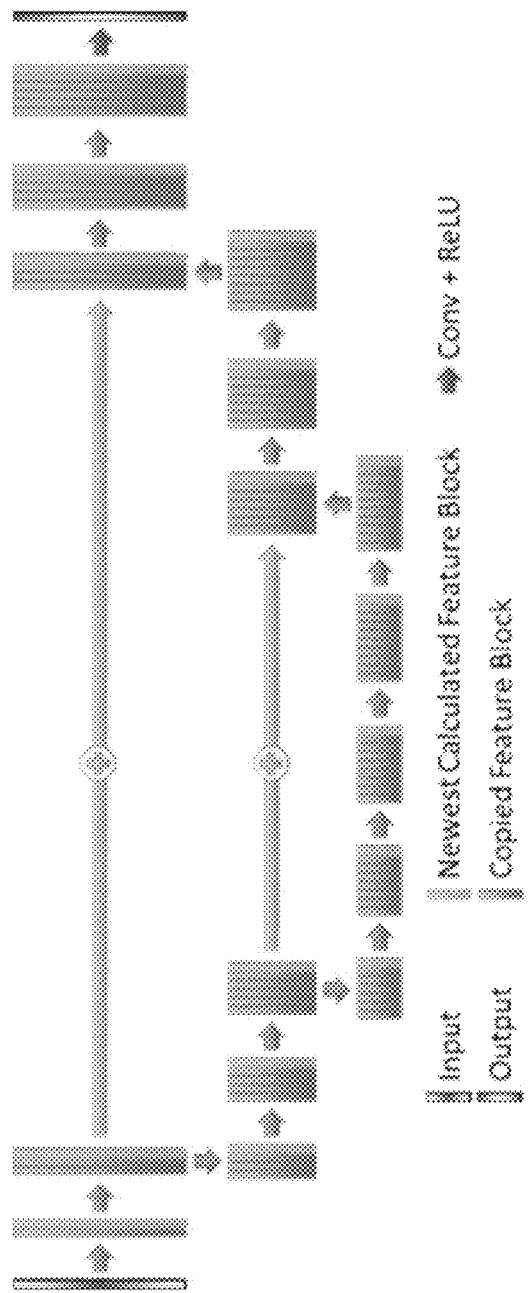
FIG. 2 is a block diagram illustrating an architecture defined by various operations, according to example embodiments.

FIG. 2 is a block diagram illustrating an architecture defined by various operations, according to example embodiments. For example, the various operations may include the dense convolution of FIG. 1A, the dense downsampling of FIG. 1B, and the u-net upsampling of FIG. 1C. In some examples, a growth rate of 16 (16 new features added after each "dense" operation) may be utilized, four dense downsampling operations, and 64 features returned during the upsampling operation. To assess the performance, Hierarchically Dense (HD) U-net may be compared to the two models which had inspired its design: U-net and DenseNet. The U-net, (which will now be referred to as the "Standard U-net") was constructed to match the HD U-net in terms of the number of downsampling operations used, and followed the conventional build of U-net (e.g., double the number of filters after each max pooling operation). DenseNet was constructed as outlined in the DenseNet publication, with dense-blocks followed by compression layers. In some embodiments, DenseNet may include seven dense blocks, five dense convolutions per dense block, and a compression factor of 0.5. All networks may be constructed to use 3D operations to handle the volumetric H&N data. Exact details of each network is summarized below in the appendix.

I.2(b): H&N Patient Data

The above system was tested using 120 H&N patients. The information for each patient, may include structure contours and the clinically delivered VMAT dose, calculated on the Eclipse Treatment Planning System. The voxel resolution of both the contours and dose were set to 5 mm³. As input, each OAR was set as separate binary masks in their own channel. The PTVs were included as their own channel, but instead of a binary mask, the mask was set to have a value equal the prescribed radiation dose. Each patient had 1-5 PTVs, with prescription doses ranging from 42.5 Gy to 72 Gy. In total, the input data used 23 channels to represent the OARs, PTVs, and prescription doses. The 22 OARs used in this study are the body, left and right brachial plexus, brain, brainstem, left and right cerebellum, left and right cochlea, constrictors, esophagus, larynx, mandible, left and right masseter, oral cavity, post arytenoid & cricoid space (PACS), left and right parotid, left and right submandibular gland (SMG), and spinal cord. In the case that the patient was missing one of the 22 OARs, the corresponding channel was set to 0 for the input.

I.2(c): Training and Evaluation

Of the 120 H&N patients, twenty patients were set aside as testing data to evaluate at the end. To assess the performance and stability of each model—HD U-net, Standard U-net, and DenseNet—a 5-fold cross validation procedure was performed on the remaining 100 patients, where, for each fold, the patients were divided into 80 training patients and 20 validation patients. During each fold, the model would have its weights randomly initialized, and then update its weights based on the training set. The validation loss is used to determine the iteration that had the best model weights. This instance of the model is then used to evaluate the validation data. After all models from every fold was trained, the models then evaluated the testing data.

Mean squared error between the predicted dose and the clinically delivered dose was used as the loss function for training each neural network model. The learning rate of each model was adjusted to maximize the validation loss as a function of epochs. The patch size used for neural training was 96×96×64. Instead of subdividing the patient contours and their corresponding dose volumes into set patches, each iteration of the model training process randomly selected a patch from the patient volume on-the-fly. This random patch selection helped "augment the data" to reduce overfitting.

To equally compare across the patients, all plans were normalized such that the PTV with the highest corresponding prescription dose had 95% of its volume receiving the prescription dose (D95). All dose statistics will also be reported relative to the prescription dose (i.e. the errors are reported as a percent of the prescription dose). As evaluation criteria PTV coverage (D98, D99), PTV max dose, homogeneity $$\left(\frac{D2-D98}{D50}\right),$$

van't Riet conformation number (Van't Riet, et al., *International Journal of Radiation Oncology\*Biology\*Physics* B37:731-736 (1997))

$$\left(\frac{(V_{PTV} \cap V_{100\% \ Iso})^2}{V_{PTV} \times V_{100\% \ Iso}}\right),$$

and the structure max and mean doses ($D_{max}$ and $D_{mean}$) were evaluated.

To maintain consistency in performance, all neural network models were trained and evaluated on an NVIDIA GTX 1080 Ti GPU with 11 GB dedicated RAM.

Figure 3:
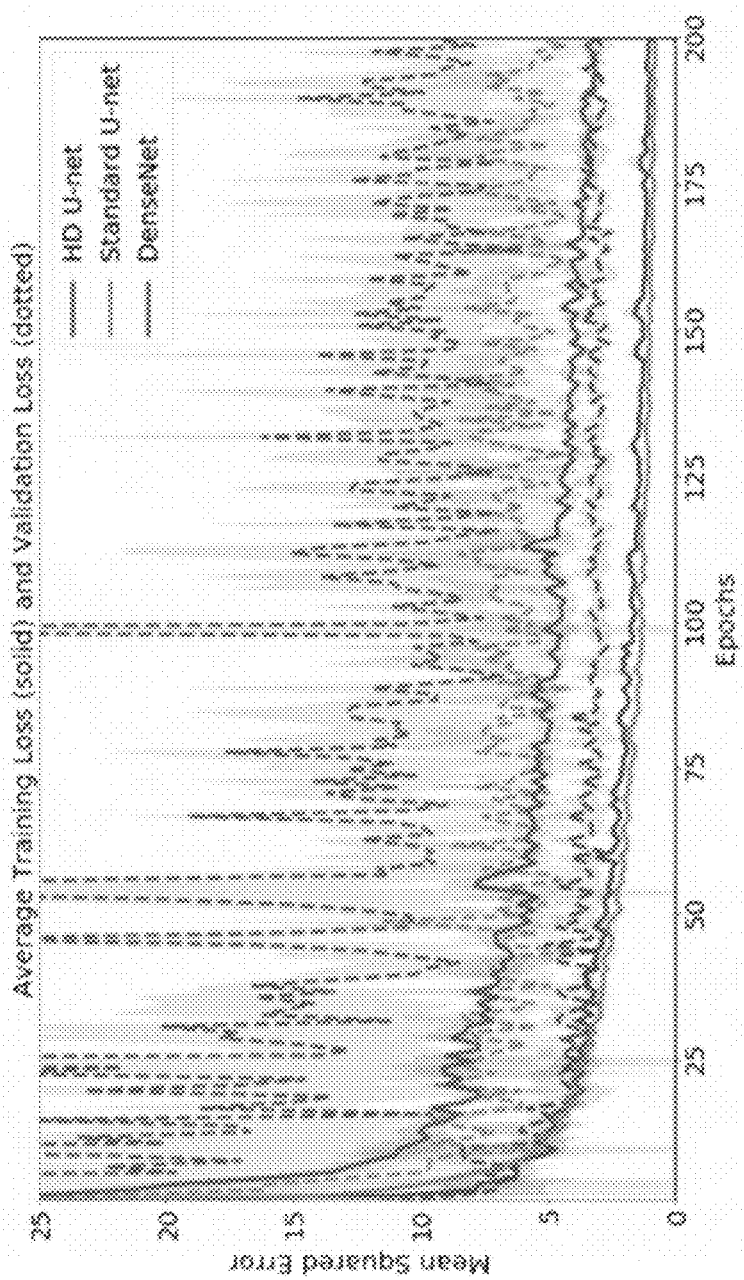
FIG. 3 is a block diagram illustrating the mean training and validation loss for the HD U-net, Standard U-net, and DenseNet, according to example embodiments.
Figure 4A:
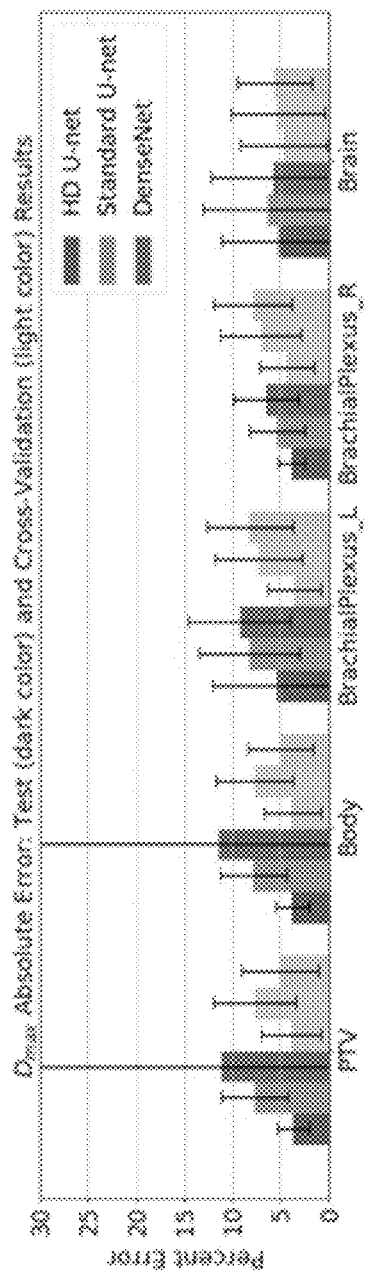
FIG. 4A is a chart illustrating $D_{max}$ absolute error, according to example embodiments.
Figure 4B:
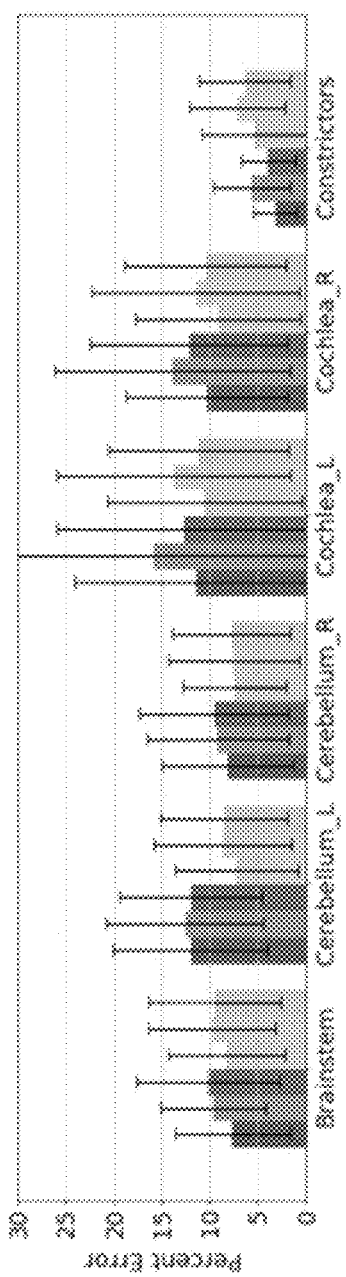
FIG. 4B is a chart illustrating $D_{max}$ absolute error, according to example embodiments.
Figure 4C:
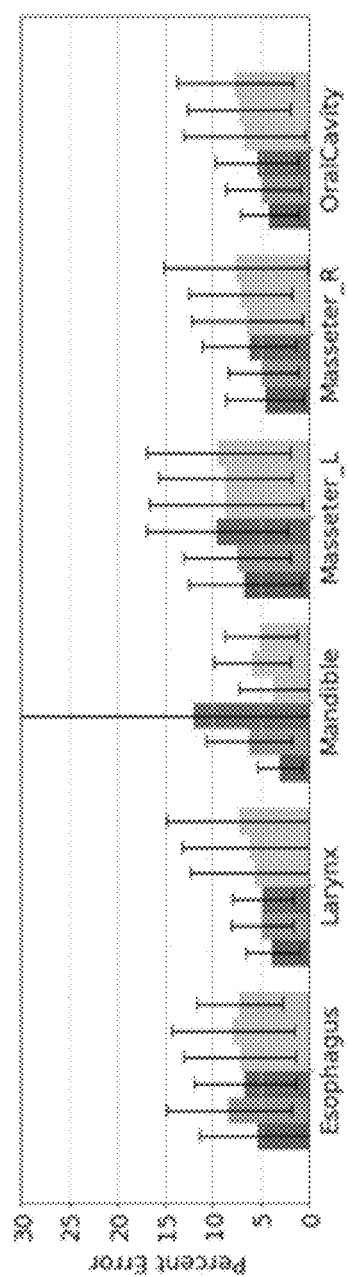
FIG. 4C is a chart illustrating $D_{max}$ absolute error, according to example embodiments.
Figure 4D:
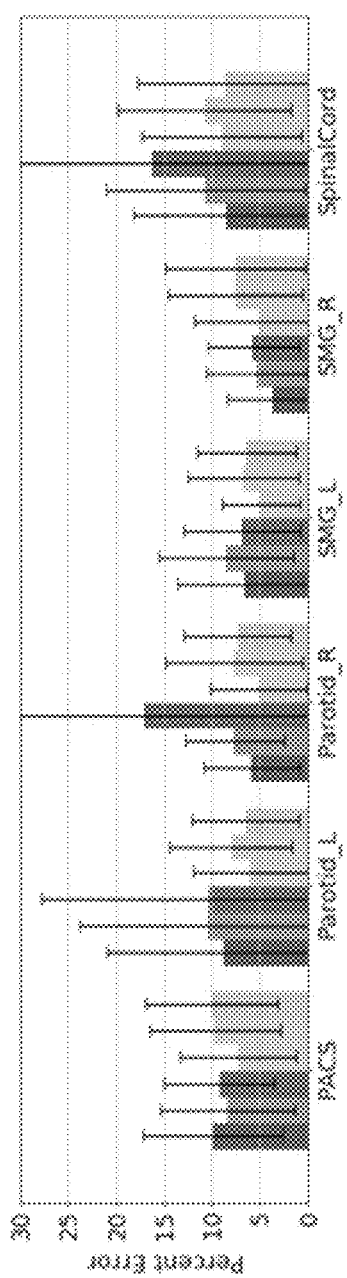
FIG. 4D is a chart illustrating $D_{max}$ absolute error, according to example embodiments.
Figure 5A:
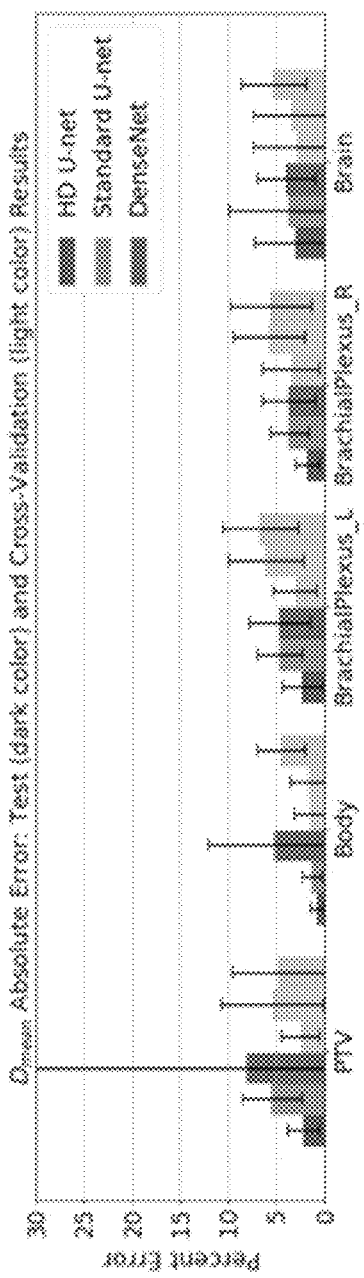
FIG. 5A is a chart illustrating $D_{mean}$ absolute error, according to example embodiments.
Figure 5B:
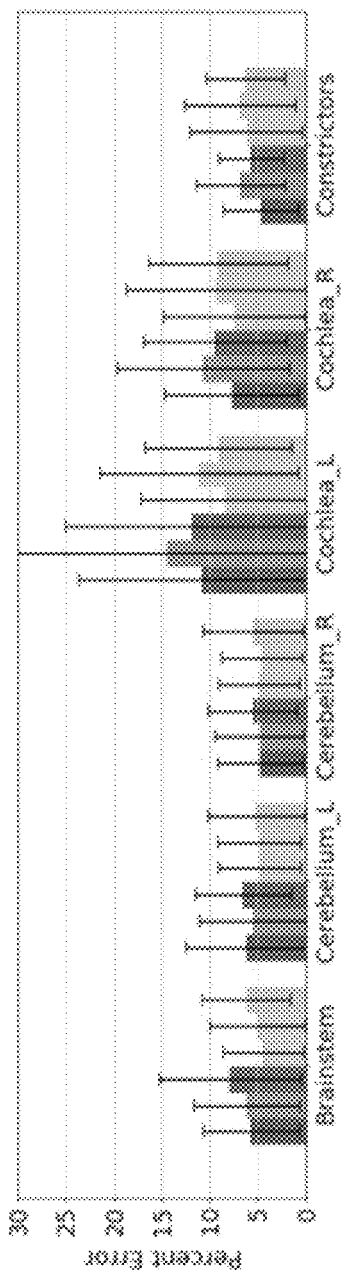
FIG. 5B is a chart illustrating $D_{mean}$ absolute error, according to example embodiments.
Figure 5C:
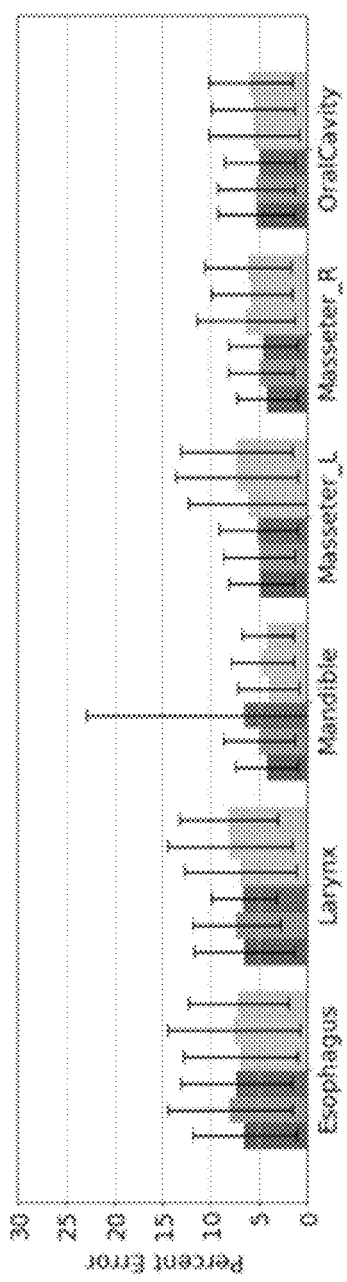
FIG. 5C is a chart illustrating $D_{mean}$ absolute error, according to example embodiments.
Figure 5D:
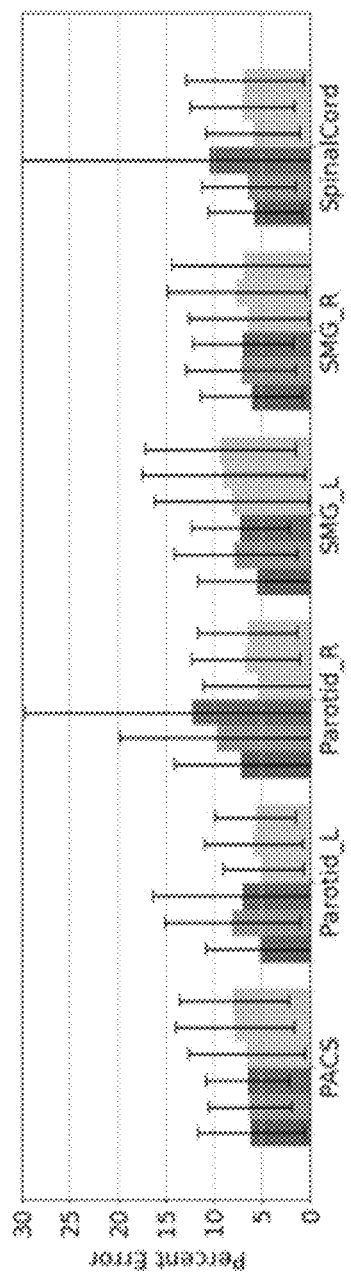
FIG. 5D is a chart illustrating $D_{mean}$ absolute error, according to example embodiments.

FIG. 3 is a block diagram illustrating the mean training and validation loss for the HD U-net, Standard U-net, and DenseNet, according to example embodiments. The HD and Standard U-net have a similar training loss as a function of epochs. However, the validation loss of the HD U-net is much lower and has less variation between the folds of the cross validation than that of the Standard U-net. This indicates that HD U-net is better at generalizing the modeling contours-to-dose, and is overfitting less to the training data. The DenseNet performed the worst for both the mean training and validation loss, as well as having the largest variation in the validation loss.

TABLE 1

Trainable parameters and prediction time for each model.

| | | Prediction time (s) Mean ± SD | |
|---|---|---|---|
| | Trainable parameters | Test | Cross-Val |
| HD U-net | 3,289,006 | 5.42 ± 1.99 | 5.39 ± 2.39 |
| Standard U-net | 40,068,385 | 4.48 ± 1.67 | 4.60 ± 2.01 |
| DenseNet | 3,361,708 | 17.12 ± 6.42 | 18.05 ± 7.97 |

Table 1 shows the number of trainable parameters and the prediction time for each model used in the study. The HD U-net and DenseNet have approximately 12 times less trainable parameters than the Standard U-net. The prediction time of the HD U-net is approximately 1 second longer for a full patient prediction, using patches of 96×96×64 and stride of 48×48×32. DenseNet had the longest prediction time of about 4 times longer than either of the U-nets.

TABLE 2

PTV coverage and max dose prediction errors for each model. Average is taken over all PTVs from all patients

| | | PTV dose coverage and max dose Prediction Error (Percent of Prescription Dose) Mean ± SD | | | |
|---|---|---|---|---|---|
| | | D95 | D98 | D99 | $D_{max}$ |
| Test Results | HD U-net | 0.02 ± 0.05 | 1.18 ± 1.82 | 1.96 ± 2.14 | 3.75 ± 1.60 |
| | Standard U-net | 0.03 ± 0.06 | 1.77 ± 2.35 | 2.65 ± 2.95 | 7.42 ± 3.26 |
| | DenseNet | 1.01 ± 9.93 | 2.45 ± 10.13 | 3.42 ± 10.39 | 7.26 ± 15.37 |
| Cross-Validation Results | HD U-net | 0.02 ± 0.05 | 2.69 ± 6.13 | 6.02 ± 12.94 | 3.84 ± 3.13 |
| | Standard U-net | 0.03 ± 0.06 | 2.86 ± 6.50 | 5.50 ± 9.69 | 7.64 ± 4.33 |
| | DensetNet | 0.03 ± 0.06 | 2.82 ± 6.32 | 6.41 ± 13.59 | 5.02 ± 3.98 |

TABLE 3

Homogeneity and Van't Riet Conformation Numbers for the ground truth and the prediction models.

| | Homogeneity$\left(\frac{D2 - D98}{D50}\right)$ | | van't Riet Conformation Number | |
|---|---|---|---|---|
| | Mean ± SD | | | |
| | Test | Cross-Val | Test | Cross-Val |
| Ground Truth | 0.06 ± 0.04 | 0.09 ± 0.09 | 0.78 ± 0.06 | 0.74 ± 0.09 |
| HD U-net | 0.08 ± 0.02 | 0.10 ± 0.05 | 0.76 ± 0.06 | 0.73 ± 0.08 |
| Standard U-net | 0.13 ± 0.04 | 0.14 ± 0.04 | 0.74 ± 0.07 | 0.73 ± 0.08 |
| DenseNet | 0.12 ± 0.18 | 0.10 ± 0.04 | 0.74 ± 0.12 | 0.74 ± 0.07 |

Table 2 shows the errors in the models' prediction on PTV coverage and max dose. While the models had similar performance in D98 and D99 for the cross-validation data, the HD U-net had better performance in predicting the dose coverage on the test set, indicating a more stable model for generalizing predictions outside of the validation and training sets used for manually tuning the hyperparameters and updating the model weights, respectively. DenseNet is inferior to the other two models in predicting the D95 of the test set. The HD U-net outperformed the other two networks in predicting the maximum dose to the PTV. Table 3 reports the homogeneity indices and the van't Riet conformation numbers for the clinical dose and the predicted dose from the networks. For the conformation number, the HD U-net performs similarly to the other models on the cross-validation data, and performs better on the test data than the other models. In terms of homogeneity, the HD U-net predicts similarly to ground truth compared to DenseNet, which are better both than that of the Standard U-net on the cross-validation data. On the test data, the HD U-net has better prediction performance on the homogeneity than the other two models.

FIGS. 4A-4D and FIGS. 5A-5D show the $D_{max}$ and $D_{mean}$ absolute errors, respectively, on all of the 22 structures and PTV. Due to the large variability in number of PTVs and prescription doses, percent errors are reported as a percent of the highest prescription dose for the patient, and the PTV $D_{mean}$ and $D_{max}$ calculation for FIGS. 4A-4D and FIGS. 5A-5D used the union of all the plan's PTVs as the region of interest. It can be easily seen that the HD U-net, shown in blue, has an overall lower prediction error on the $D_{max}$ and $D_{mean}$ than the other two networks in this study. For the cross-validation data, the HD U-net, Standard U-net, and DenseNet predicted, on average, the $D_{max}$ within 6.23±1.94%, 8.11±1.87%, and 7.65±1.67%, respectively, and the $D_{mean}$ within 5.30±1.79%, 6.38±2.01%, and 6.49±1.43%, respectively, of the prescription dose. For the test data, the models predicted $D_{max}$ within 6.30±2.70%, 8.21±2.87%, and 9.30±3.44%, respectively, and $D_{mean}$ within 5.05±2.13%, 6.40±2.63%, and 6.83±2.27%, respectively, or the prescription dose. Overall, the HD U-net had the best performance on both the cross-validation and test data. DenseNet had the largest discrepancy between its performance on the cross-validation data and test data, indicating its prediction volatility on data outside of its training and validation set.

Figure 6A:
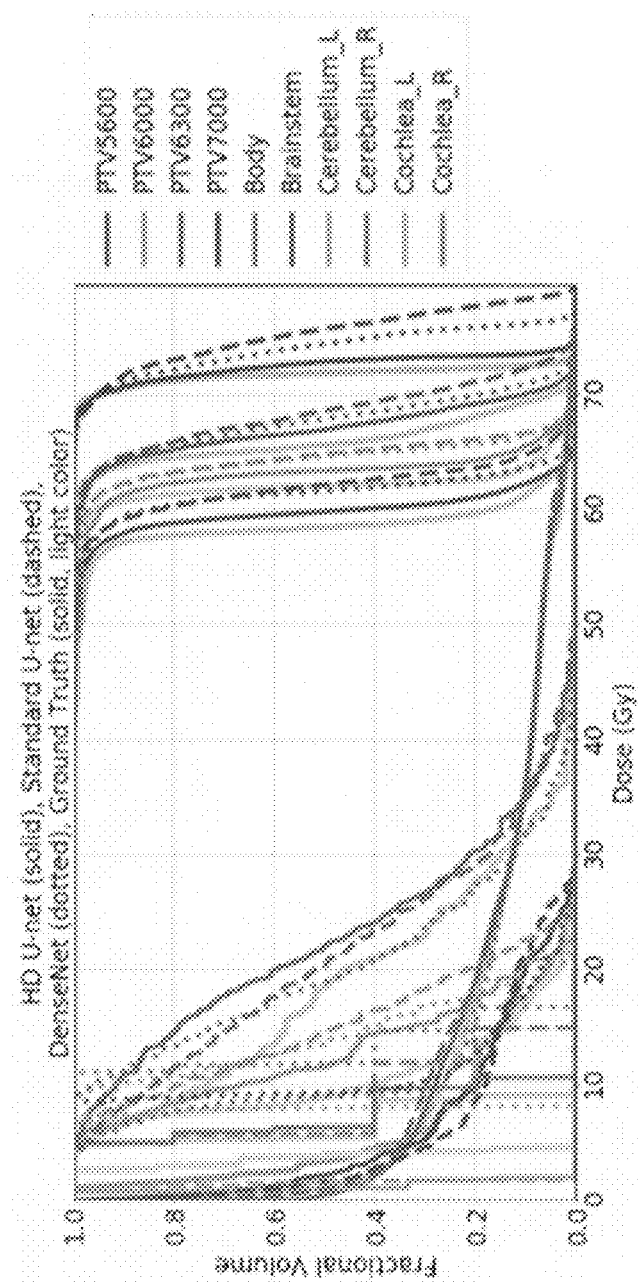
FIG. 6A is a chart illustrating an example dose volume histogram (DVH) from a patient from the test data, according to example embodiments.
Figure 6B:
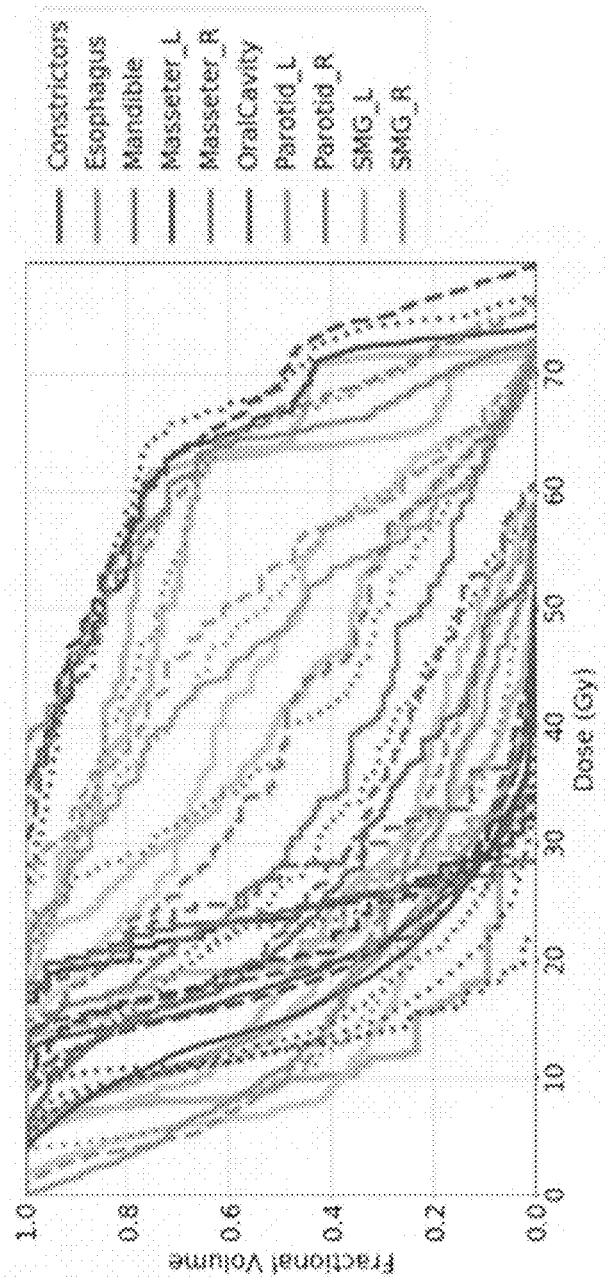
FIG. 6B is a chart illustrating an example dose volume histogram (DVH) from a patient from the test data, according to example embodiments.

FIGS. 6A-6B show an example DVH from a patients from the test data. The solid line with the lighter color variant represents the clinical ground truth dose, while the darker color variants represent the predicted dose from HD Unet (solid), Standard U-net (dashed), and DenseNet (dotted). For this example patient, the HD Unet is superior to the other models in predicting the dose to the PTVs. Prediction of OAR dose are more variable between the models. This is also reflected in FIGS. 4A-4D and FIGS. 5A-5D, where the standard deviation in prediction is small for the PTVs using the HD U-net, and larger on the OAR $D_{max}$ and $D_{mean}$ prediction.

Figure 7:
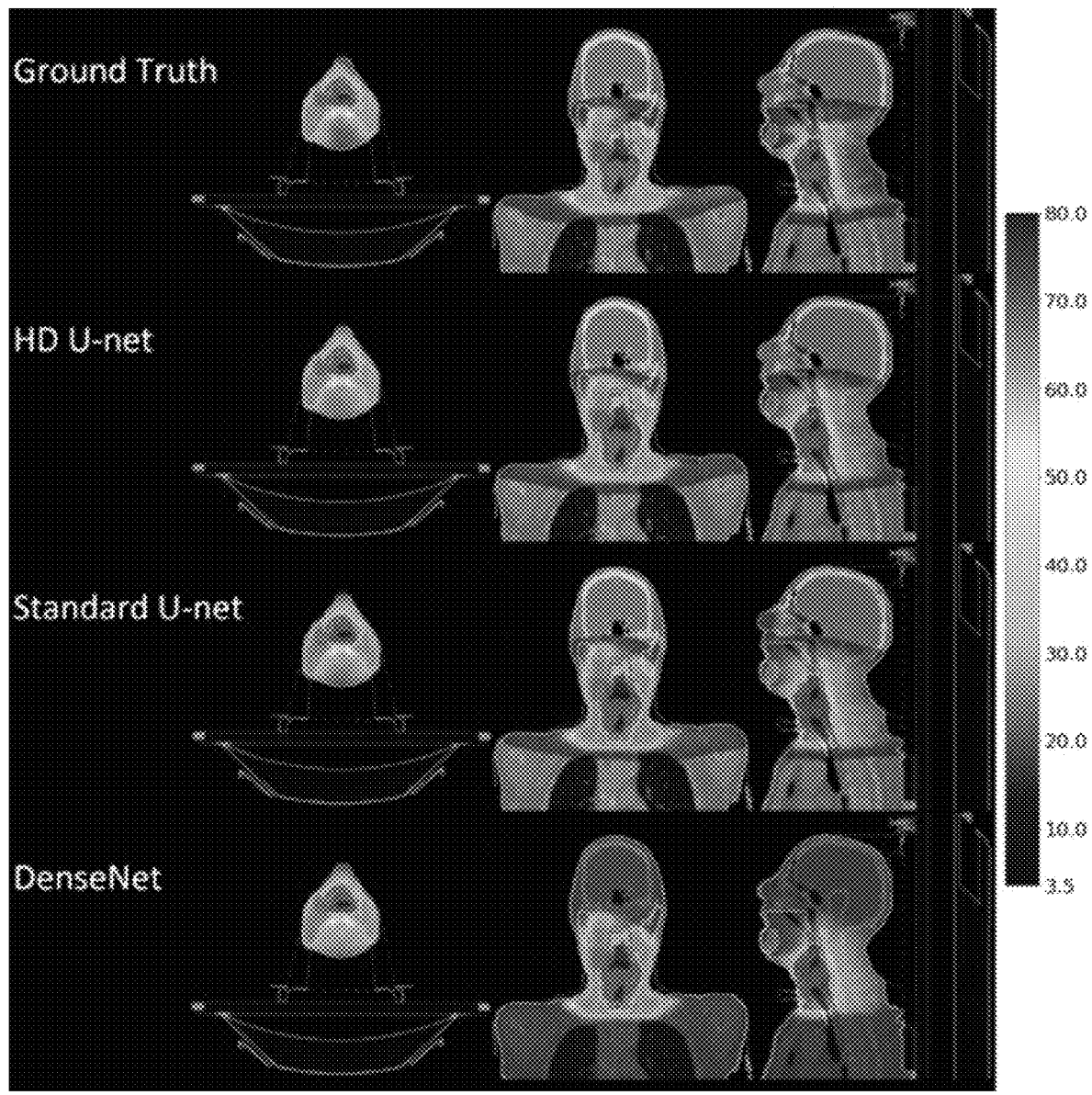
FIG. 7 is a block diagram illustrating dose color wash for the patient in FIGS. 6A-6B, according to example embodiments.

FIG. 7 shows the dose color wash for the same patient in FIGS. 6A-6B. Visually, the dose prediction models have comparable dose to the PTVs, with the Standard U-net and DenseNet slightly hotter than the HD U-net. The DenseNet also predicts dose above 3.5 Gy everywhere in the body, which is also reflected in the DVH in FIGS. 6A-6B (purple dotted line). The back of the neck is predicted to have more dose by all of the models, as compared to ground truth, which may represent a lack of data representation in the training data, or a lack of information being fed into the deep learning model itself.

I.3: Discussion

This is the first instance of an accurate volumetric dose prediction for H&N cancer patients treated with VMAT. Existing plan prediction models are largely based around Knowledge Based Planning (KBP) (Zhu, X. et al., *Medical physics* 38:719-726 (2011); Appenzoller, et al. *Medical physics* 39:7446-7461 (2012); Wu, et al. *Radiotherapy and Oncology* 112:221-226 (2014); Shiraishi, et al., *Medical physics* 42:908-917 (2015); Moore, et al., *International Journal of Radiation Oncology*Biology*Physics* 81:545-551 (2011); Shiraishi, et al., *Medical physics* 43:378-387 (2016); Wu, et al., *Medical Physics* 36:5497-5505 (2009); Wu, et al., *International Journal of Radiation Oncology*Biology*Physics* 79:1241-1247 (2011); Wu, et al., *Medical Physics* 40: 021714-n/a (2013); Tran, et al.,

*Radiation Oncology* 12:70 (2017); Yuan, et al., *Medical Physics* 39:6868-6878 (2012); Lian, et al., *Medical Physics* 40:121704-n/a (2013); Folkerts, et al., *Medical Physics* 43; 3653-3654 (2016); Folkerts, et al., *American Association of Physicists in Medicine*. (Medical Physics)), with clinical/commercial implementations available known as Varian RapidPlan (Varian Medical Systems, Palo Alto, Calif.) and Pinnacle Auto-Planning Software (Philips Radiation Oncology Systems). These KBP methods have historically been designed to predict the DVH of a given patient, instead of the full volumetric dose prediction. The only exception is the study by Shiraishi and Moore (Shiraishi, S. & Moore, K. L. Knowledge-based prediction of three-dimensional dose distributions for external beam radiotherapy. Medical physics 43, 378-387 (2016)) in 2016, where they perform 3D dose prediction. However, their study is currently only evaluated on prostate patients, and thus the results are not comparable to the results for H&N patients. A study by Tol et al. (Tol, et al., *International Journal of Radiation Oncology Biology•Physics* 91:612-620 (2015)) that evaluated Rapid-Plan on H&N cancer patients, had found that, in one of their evaluation groups, RapidPlan, had a mean prediction error of as large as 5.5 Gy on the submandibular gland, with the highest error on a single patient's OAR as high as 21.7 Gy on the lower larynx. Since their patients were clinically treated from 54.25 to 58.15 Gy, this translates to roughly 10% and 40% error, respectively in predictive performance Another study by Krayenbuehl et al. (Krayenbuehl, et al. *Radiation Oncology* 10:226 (2015)) had used Pinnacle Auto-Planning Software. However, in this study, the plan prediction aspect of the software was hidden from the user, and simply used as part of the auto-planning software itself, making this study's methodology not directly comparable to ours.

AIt is currently a challenge to directly compare against other non-commercial prediction models, particularly since they are developed in-house and are proprietary to the institution that developed it. It is typically infeasible to obtain a copy or to faithfully replicate it to the exact specifications that were used by the originators. In addition, training and evaluation of the model is usually performed using the institution's own data, and is often unavailable to the public to replicate the results or to train their own model for an unbiased comparison.

Although the DenseNet had the poorest performance of the 3 models, it is due to the fact that the DenseNet is incapable of capturing global information into its prediction as the U-nets do. This should not be seen as an oversight of DenseNet, as the authors of the paper proposed the concept of densely connected convolutional neural networks as a module, implying that this concept can be applied to more complex models. Their proposed DenseNet was used to illustrate the efficient feature propagation and reuse, alleviate the vanishing gradient, and reduce the number of parameters to moderate the overfitting issue.

This dose prediction tool can currently be used as a clinical guidance tool, where the final tradeoff decisions and deliverable plan will still be made by the physician and dosimetrist.

I.4: Conclusion

Discussed above is a hierarchically densely connected U-net architecture, HD U-net, and applied the model to volumetric dose prediction for patients with H&N cancer. Using the proposed implementation, the system is capable of accurately predicting the dose distribution from the PTV and OAR contours, and the prescription dose. On average, the proposed model is capable of predicting the OAR max dose within 6.3% and mean dose within 5.1% of the prescription dose on the test data. The other models, the Standard U-net and DenseNet, performed worse, having an OAR max dose prediction error of 8.2% and 9.3%, respectively, and mean dose prediction error of 6.4% and 6.8%, respectively. HD U-net also outperformed the other two models in homogeneity, dose conformity, and dose coverage on the test data. In addition, the model is capable of using 12 times less trainable parameters than the Standard U-net, and predicted the patient dose 4 times faster than DenseNet. A.1. Exemplary details on deep learning architectures:

TABLE 4

Details of deep learning architectures. Dense Conv and U-net Upsample follow the notation outlined in FIG. 1. All convolutions mentioned in this table use 3 × 3 × 3 kernels and are followed by the ReLU non-linear activation.

| Layer number | HD U-net | | Standard U-net | | DenseNet | |
|---|---|---|---|---|---|---|
| | Layer type | Number features/channels | Layer type | Number features/channels | Layer type | Number features/channels |
| 1 | Input | 23 | Input | 23 | Input | 23 |
| 2 | Dense Conv | 39 | Conv | 32 | Dense Conv | 47 |
| 3 | Dense Conv | 55 | Conv | 32 | Dense Conv | 71 |
| 4 | Dense Downsample | 71 | Max Pooling | 32 | Dense Conv | 95 |
| 5 | Dense Conv | 87 | Conv | 64 | Dense Conv | 119 |
| 6 | Dense Conv | 103 | Conv | 64 | Dense Conv | 143 |
| 7 | Dense Downsample | 119 | Max Pooling | 64 | Conv | 72 |
| 8 | Dense Conv | 135 | Conv | 128 | Dense Conv | 96 |
| 9 | Dense Conv | 151 | Conv | 128 | Dense Conv | 120 |
| 10 | Dense Downsample | 167 | Max Pooling | 128 | Dense Conv | 144 |
| 11 | Dense Conv | 183 | Conv | 256 | Dense Conv | 168 |
| 12 | Dense Conv | 199 | Conv | 256 | Dense Conv | 192 |
| 13 | Dense Downsample | 215 | Max Pooling | 256 | Conv | 96 |
| 14 | Dense Conv | 231 | Conv | 512 | Dense Conv | 120 |
| 15 | Dense Conv | 247 | Conv | 512 | Dense Conv | 144 |
| 16 | Dense Conv | 263 | Conv | 512 | Dense Conv | 168 |

TABLE 4-continued

Details of deep learning architectures. Dense Conv and U-net Upsample follow the notation outlined in FIG. 1. All convolutions mentioned in this table use 3 × 3 × 3 kernels and are followed by the ReLU non-linear activation.

| Layer number | HD U-net Layer type | Number features/ channels | Standard U-net Layer type | Number features/ channels | DenseNet Layer type | Number features/ channels |
|---|---|---|---|---|---|---|
| 17 | Dense Conv | 279 | Conv | 512 | Dense Conv | 192 |
| 18 | U-net Upsample | 263 | U-net Upsample | 512 | Dense Conv | 216 |
| 19 | Dense Conv | 279 | Conv | 256 | Conv | 108 |
| 20 | Dense Conv | 295 | Conv | 256 | Dense Conv | 132 |
| 21 | U-net Upsample | 215 | U-net Upsample | 256 | Dense Conv | 156 |
| 22 | Dense Conv | 231 | Conv | 128 | Dense Conv | 180 |
| 23 | Dense Conv | 247 | Conv | 128 | Dense Conv | 204 |
| 24 | U-net Upsample | 167 | U-net Upsample | 128 | Dense Conv | 228 |
| 25 | Dense Conv | 183 | Conv | 64 | Conv | 114 |
| 26 | Dense Conv | 199 | Conv | 64 | Dense Conv | 138 |
| 27 | U-net Upsample | 119 | U-net Upsample | 64 | Dense Conv | 162 |
| 28 | Dense Conv | 135 | Conv | 32 | Dense Conv | 186 |
| 29 | Dense Conv | 151 | Conv | 32 | Dense Conv | 210 |
| 30 | Conv | 1 | Conv | 1 | Dense Conv | 234 |
| 31 | | | | | Conv | 117 |
| 32 | | | | | Dense Conv | 141 |
| 33 | | | | | Dense Conv | 165 |
| 34 | | | | | Dense Conv | 189 |
| 35 | | | | | Dense Conv | 213 |
| 36 | | | | | Dense Conv | 237 |
| 37 | | | | | Conv | 119 |
| 38 | | | | | Dense Conv | 143 |
| 39 | | | | | Dense Conv | 167 |
| 40 | | | | | Dense Conv | 191 |
| 41 | | | | | Dense Conv | 215 |
| 42 | | | | | Dense Conv | 239 |
| 43 | | | | | Conv | 120 |
| 44 | | | | | Conv | 1 |

Section II: Prostate IMRT Patients

With the advancement of treatment modalities in radiation therapy for cancer patients, outcomes have improved, but at the cost of increased treatment plan complexity and planning time. The accurate prediction of dose distributions would alleviate this issue by guiding clinical plan optimization to save time and maintain high quality plans. Described herein is a modified convolutional deep network model, U-net (originally designed for segmentation purposes), for predicting dose from patient image contours. Using the modified convolutional deep network model, the system is able to accurately predict the dose of intensity-modulated radiation therapy (IMRT) for prostate cancer patients, where the average dice similarity coefficient is 0.91 when comparing the predicted vs. true isodose volumes between 0% and 100% of the prescription dose. The average value of the absolute differences in [max, mean] dose is found to be under 5% of the prescription dose, specifically for each structure is [1.80%, 1.03%](PTV), [1.94%, 4.22%](Bladder), [1.80%, 0.48%](Body), [3.87%, 1.79%](L Femoral Head), [5.07%, 2.55%](R Femoral Head), and [1.26%, 1.62%](Rectum) of the prescription dose.

II.1: Introduction

Radiation therapy has been one of the leading treatment methods for cancer patients, and with the advent and advancements of innovative modalities, such as intensity modulated radiation therapy (IMRT) (A. Brahme, *Radiotherapy and Oncology* 1988; 12(2):129-140; Bortfeld, et al., *Physics in Medicine and Biology*, 1990; 35(10):1423; Bortfeld, et al., *International Journal of Radiation Oncology\*Biology\* Physics*, 1994; 28(3):723-730; S. Webb, *Physics in Medicine and Biology,* 1989; 34(10):1349; Convery, et al., *Physics in Medicine and Biology,* 1992; 37(6): 1359; Xia, et al., *Medical Physics,* 1998; 25(8):1424-1434; Keller-Reichenbecher, et al., *International Journal of Radiation Oncology\* Biology\* Physics,* 1999; 45(5):1315-1324) and volume modulated arc therapy (VMAT) (C. X. Yu, *Physics in Medicine and Biology,* 1995; 40(9):1435; K. Otto, *Medical physics,* 2008; 35(1):310-317; Palma, et al., *International Journal of Radiation Oncology\*Biology\*Physics,* 2008; 72(4):996-1001; Shaffer, et al., *Clinical Oncology,* 2009; 21(5):401-407; Shaffer, et al., *International Journal of Radiation Oncology\*Biology\*Physics,* 2010; 76(4):1177-1184; Xing, *Physics in Medicine & Biology,* 2003; 48(10): 1333; Earl, et al., *Physics in medicine and biology,* 2003; 48(8):1075; Daliang, et al., *Physics in Medicine & Biology,* 2009; 54(21):6725), plan quality has drastically improved over the last few decades. However, such a development comes at the cost of treatment planning complexity. While this complexity has given rise to better plan quality, it can be double-edged sword that increases the planning time and obscures the tighter standards that these new treatment modalities are capable of meeting. This has resulted in greatly increased clinical treatment planning time, where the dosimetrist goes through many iterations to adjust and tune treatment planning parameters, as well as receiving feedback from the physician many times before the plan is approved. The prediction of dose distributions and constraints has become an active field of research, with the goal of creating consistent plans that are informed by the ever-growing body of treatment planning knowledge, as well guiding clinical plan optimization to save time and to maintain high quality treatment plans across planners of different experiences and skill levels.

Figure 8A:
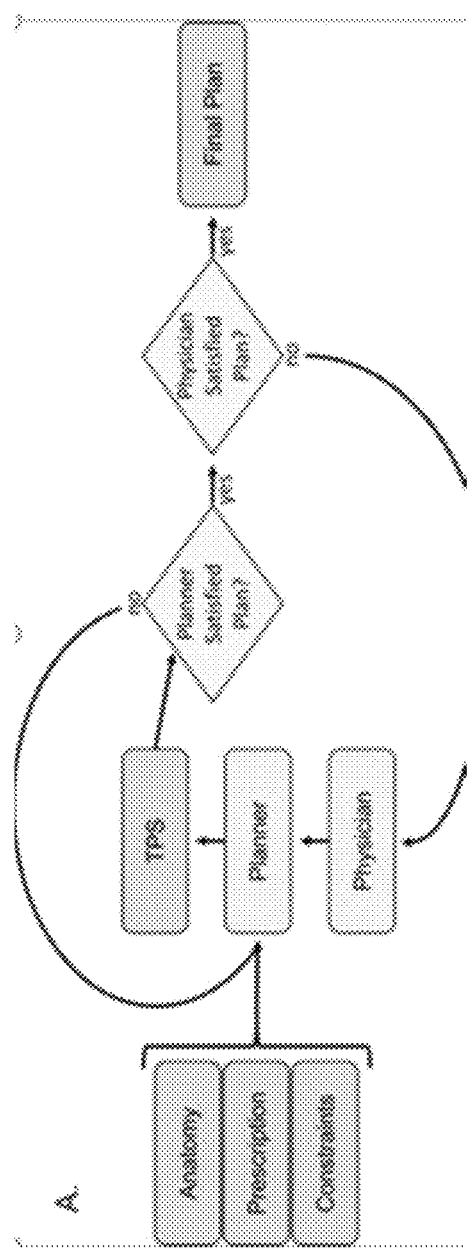
FIG. 8A is a block diagram illustrating current treatment planning workflow, according to example embodiments.

FIG. 8A is a block diagram illustrating a treatment planning workflow, according to example embodiments. The treatment planning workflow of FIG. 8A may include many iterations for the dosimetrist and physician.

Figure 8B:
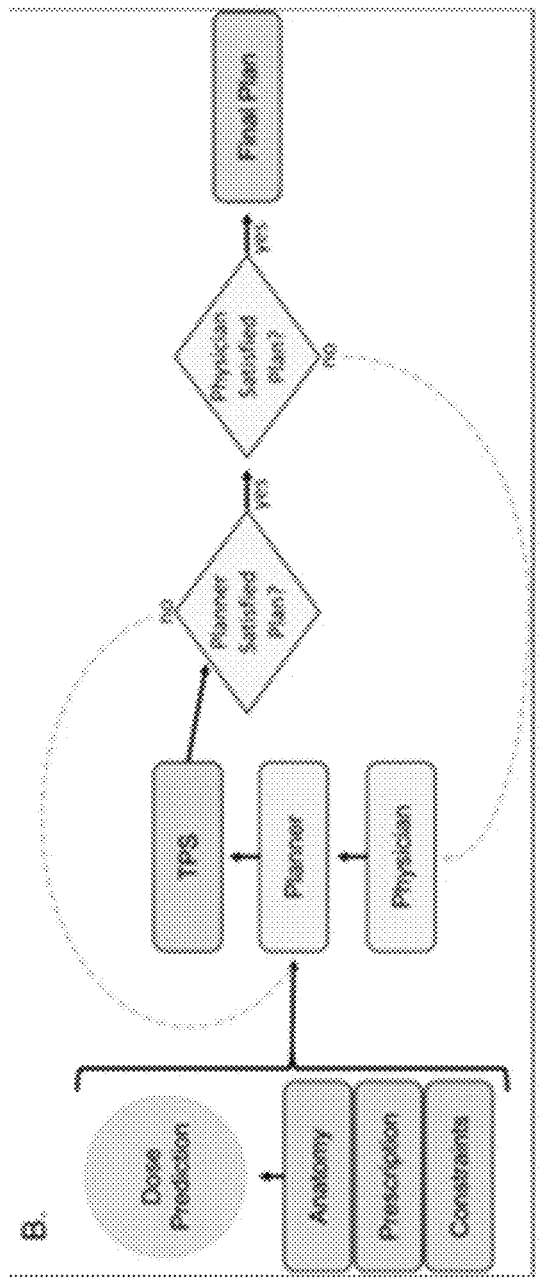
FIG. 8B is block diagram illustrating a workflow associated with artificial intelligence-based dose prediction, according to example embodiments.

FIG. 8B is a block diagram illustrating a workflow with a dose prediction model in place, according to example embodiments. As illustrated, although the overall workflow does not change, the number of iterations decreases considerably.

Much of the work for dose prediction in radiotherapy has been revolving around a paradigm known as knowledge-based planning (KBP) (Zhu, et al., *Medical physics,* 2011; 38(2):719-726; Appenzoller, et al., *Medical physics,* 2012; 39(12):7446-7461; Wu, et al., *Radiotherapy and Oncology,* 2014; 112(2):221-226; Shiraishi, et al., *Medical physics,* 2015; 42(2):908-917; Moore, et al., *International Journal of Radiation Oncology\*Biology\*Physics,* 2011; 81 (2):545-551; Shiraishi, et al., *Medical physics,* 2016; 43(1):378-387; Wu, et al., *Medical Physics,* 2009; 36(12):5497-5505; Wu, et al., *International Journal of Radiation Oncology\*Biology\*Physics,* 2011; 79(4):1241-1247; Wu, et al., *Medical Physics,* 2013; 40(2):021714-n/a; Tran, et al., *Radiation Oncology,* 2017; 12(1):70; Yuan, et al., *Medical Physics,* 2012; 39(11):6868-6878; Lian, et al., *Medical Physics,* 2013; 40(12):121704-n/a; Folkerts, et al., *Medical Physics,* 2016; 43(6Part26):3653-3654; Folkerts, et al., Paper presented at: *American Association of Physicists in Medicine,* 2017; Denver, Colo.), which has been focused on the prediction of a patient's dose volume histogram (DVH) and dose constraints, using historical patient plans and information. While KBP has seen large successes and advancements that have improved the reliability of its predictions, these methods require the enumeration of parameters/features in order to feed into a model for dose and DVH prediction. Although much time and effort has been spent in selecting handcrafted features—such spatial information of organs at risk (OAR) and planning target volumes (PTV), distance-to-target histograms (DTH), overlapping volume histograms (OVH), structure shapes, number of delivery fields, etc. (Shiraishi, et al., *Medical physics,* 2016; 43(1):378-387; Wu, et al., *Medical Physics,* 2009; 36(12): 5497-5505; Wu, et al., *International Journal of Radiation Oncology\*Biology\*Physics,* 2011; 79(4):1241-1247; Wu, et al., *Medical Physics,* 2013; 40(2):021714-n/a; Tran, et al., *Radiation Oncology,* 2017; 12(1):70; Yuan, et al., *Medical Physics,* 2012; 39(11):6868-6878; Lian, et al., *Medical Physics,* 2013; 40(12):121704-n/a; Folkerts, et al., *Medical Physics,* 2016; 43(6Part26):3653-3654; Folkerts, et al., Paper presented at: *American Association of Physicists in Medicine,* 2017; Denver, Colo.)—it is still deliberated as to which features have the greatest impact and what other features would considerably improve the dose prediction. Artificial neural networks have been applied to learn more complex relationships between the handcrafted data (Shiraishi, et al., *Medical physics,* 2016; 43(1):378-387), but it is still limited by the inherent information present in that data.

In the last few years, deep learning has made a quantum leap in the advancement of many areas. One particular area was the progression of convolutional neural network (CNN) (LeCun, et al., *Neural computation,* 1989; 1(4):541-551) architectures for imaging and vision purposes (Krizhevsky, et al., Paper presented at: *Advances in neural information processing systems* 2012; Girshick, et al., Paper presented at: *Proceedings of the IEEE conference on computer vision and pattern recognition,* 2014; Simonyan, et al., *arXiv preprint arXiv:*14091556, 2014). In 2015, fully convolutional networks (FCN) (Long, et al., *Paper presented at: Proceedings of the IEEE Conference on Computer Vision and Pattern Recognition,* 2015) were proposed, and outperformed state-of-the-art techniques of its time at semantic segmentation. Shortly after, more complex models were built around the FCN concept in order to solve some of its shortcomings. One particular architecture that was proposed was a model called U-net (Ronneberger, et al., *Paper presented at: International Conference on Medical Image Computing and Computer-Assisted Intervention,* 2015), which focused on the semantic segmentation on biomedical images. There were three central ideas in the U-net's architecture design: 1) a large number of max pooling operations to allow for the convolution filters to find global, non-local features, 2) transposed convolution operations—also known as deconvolution (Noh, et al., *Paper presented at: Proceedings of the IEEE International Conference on Computer Vision,* 2015) or up-convolution (Ronneberger, et al., *Paper presented at: International Conference on Medical Image Computing and Computer-Assisted Intervention,* 2015)—to return the image to its original size, and 3) copying the maps from the first half of the U-net in order to preserve the lower-level, local features. While inserting some domain knowledge into the problem may be helpful due to a limited amount of data, deep learning may be used to reduce dependence on handcrafted features, and allow the deep network to learn its own features for prediction. Even though the U-net and other FCN architectures were designed for the task of image segmentation, with some innovative modifications, the U-net architecture will be able to accurately predict a voxel-level dose distribution simply from patient contours, by learning to abstract its own high-level local and broad features. This motivation is two-fold: 1) (short term motivation) to provide guidance for the dosimetrist during clinical plan optimization in order to improve the plan quality and uniformity and, to reduce the total planning time by decreasing the number of iterations the dosimetrist has to go through with the physician and treatment planning optimization, and 2) (long term motivation) to eventually develop an artificial intelligent treatment planning tool, capable of creating entire clinically acceptable plans.

II.2: U-Net Architecture for Dose Prediction

Figure 9:
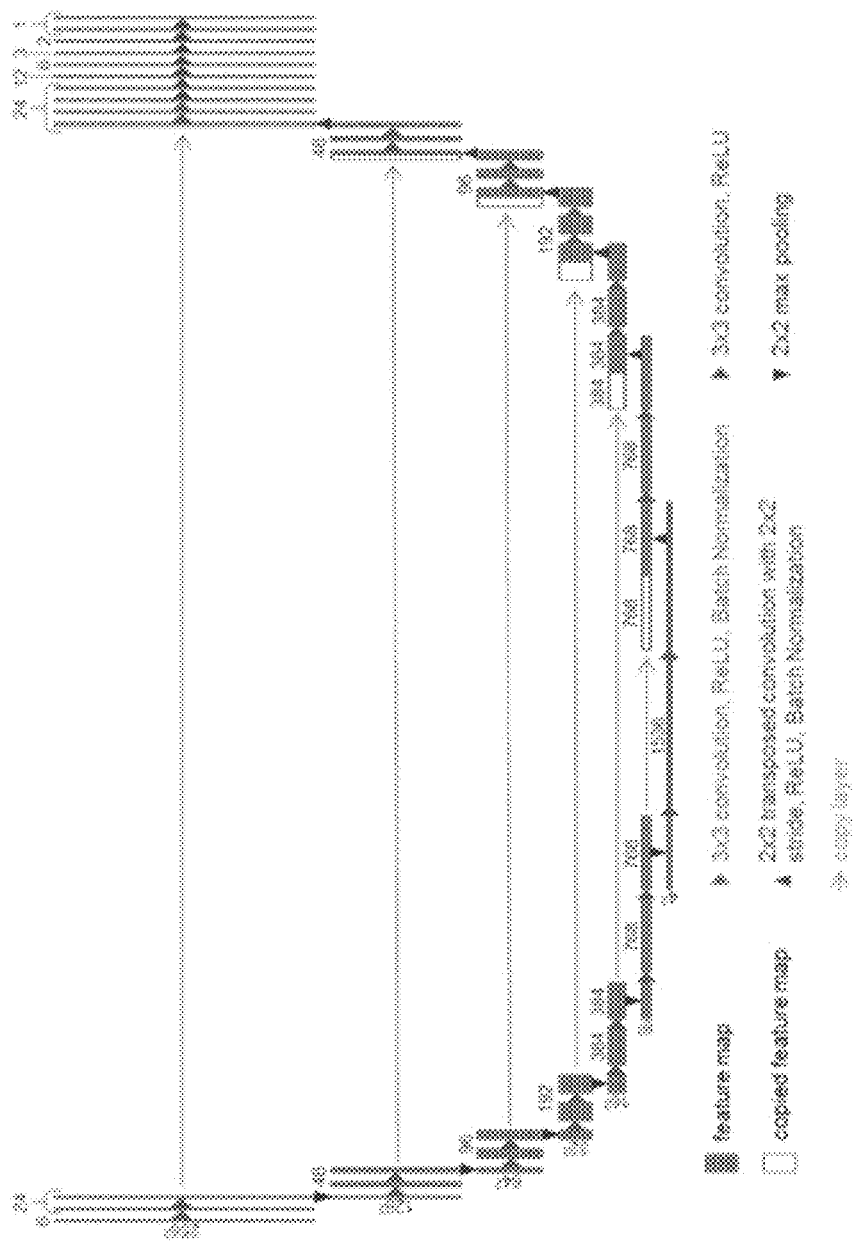
FIG. 9 is a block diagram illustrating a seven-level hierarchy U-net, according to example embodiments.

FIG. 9 is a block diagram illustrating a seven-level hierarchy U-net, according to example embodiments. The seven-level hierarchy U-net may include some innovative modifications made on the original design to achieve the goal of contour-to-dose mapping. In a particular example, the choice for 7 levels with 6 max pooling operations was made to reduce the feature size from 256×256 pixels down to 4×4 pixels, allowing for the 3×3 convolution operation to connect the center of the tumor to the edge of the body for all of the patient cases. Zero padding was added to the convolution process so that the feature size is maintained. Seven CNN layers, denoted with the purple arrows in FIG. 9, were added after the U-net in order to smoothly reduce the number of filters to one, allowing for high precision prediction. Batch normalization (Ioffe, et al., *Paper presented at: International Conference on Machine Learning,* 2015) (BN) was added after the convolution and rectified linear unit (ReLU) operations in the U-net, which allows for a more equal updating of the weights throughout the U-net, leading to faster convergence. It should be noted that the original BN publication suggests performing the normalization process before the non-linearity operation; however, during testing, it was found that better performance was had using normalization after the ReLU operation—the validation's mean squared error after 10 epochs was 0.3528 for using BN before ReLU and 0.0141 for using BN after ReLU. The input starts with 6 channels of 256×256 pixel images, with each channel representing a binary mask for 1 of the 6 contours used in this study.

Figure 10:
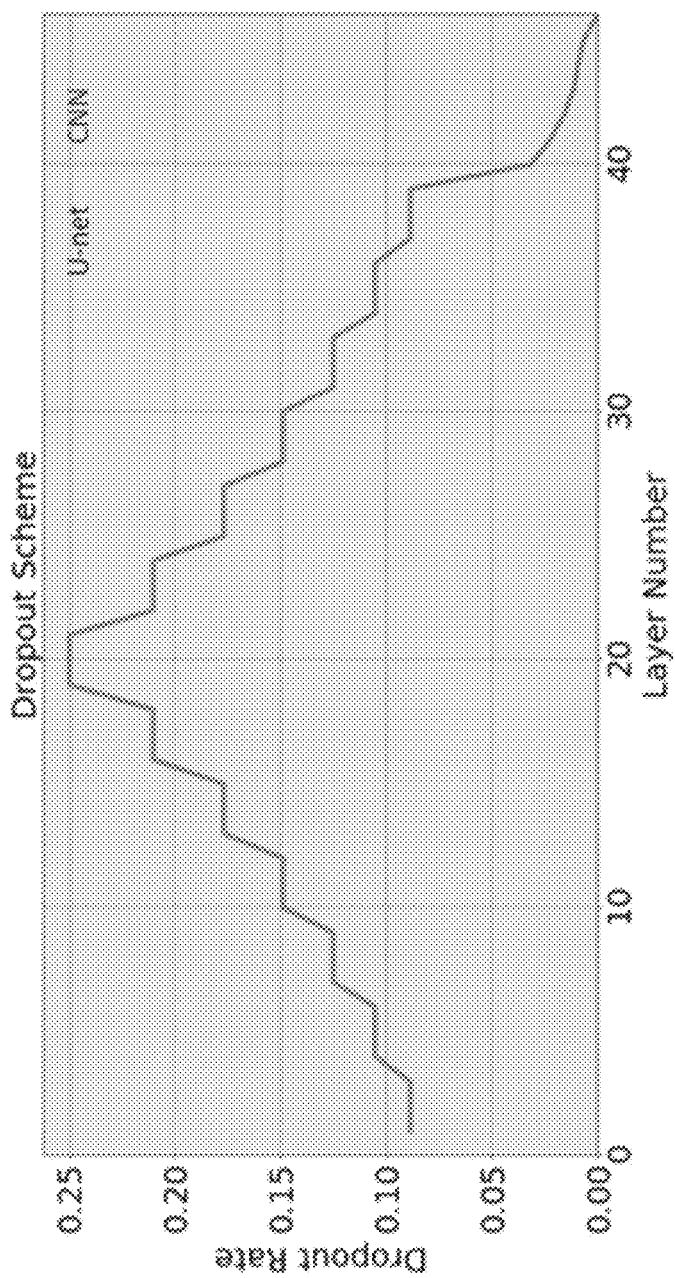
FIG. 10 is a block diagram illustrating a dropout scheme implemented for the U-net and CNN layers, according to example embodiments.

To prevent the model from over-fitting, dropout (Srivastava, et al., *Journal of machine learning research*, 2014; 15(1):1929-1958) regularization was implemented according to the scheme shown in FIG. 10, which is represented by the equation:

$$dropout_{rate} = rate_{max} \times \left(\frac{\text{current number of filters}}{\text{max number of filters}}\right)^{1/n}.$$

For the present setup, $rate_{max}=0.25$ and the max number of filters=1536 was chosen. For the U-net layers, n=4; for the added CNN layers, n=2. The choice for the dropout parameters was determined empirically, until the gap between the validation loss and training loss did not tend to increase during training.

The Adam algorithm (Kingma, et al., *arXiv preprint arXiv*:14126980, 2014) was chosen as the optimizer to minimize the loss function. In total, the network consisted of 46 layers. The deep network architecture was implemented in Keras (Chollet, et al., In. *https://github.com/fchollet/keras: Github*, 2015) with Tensorflow (Abadi, et al., *arXiv preprint arXiv*:160304467, 2016) as the backend.

II.3: Training and Evaluation

To test the feasibility of this model, treatment plans of 88 clinical coplanar IMRT prostate patients, each planned with 7 IMRT fields at 15 MV, were used. The 7 IMRT beam angles were similar across the 88 patients. Each patient had 6 contours: planning target volume (PTV), bladder, body, left femoral head, right femoral head, and rectum. The volume dimensions were reduced to 256×256×64 voxels, with resolutions of 2×2×2.5 mm³. For training, all patient doses were normalized such that the mean dose delivered to the PTV was equal to 1.

The U-net model was trained on single slices of the patient. As input, the 6 contours were each treated as their own channel in the image (analogous to how RGB images are treated as 3 separate channels in an image). The output is the U-net's prediction of the dose for that patient slice. The loss function was chosen to be the mean squared error between the predicted dose and the true dose delivered to the patient.

Since the central slices containing the PTV were far more important than the edge slices for dose prediction, a Gaussian sampling scheme was implemented—the center slice would more likely be chosen when the training function queried for another batch of random samples. The distance from the center slice to the edge slice was chosen to equal 3 standard deviations for the Gaussian sampling.

Figure 11:
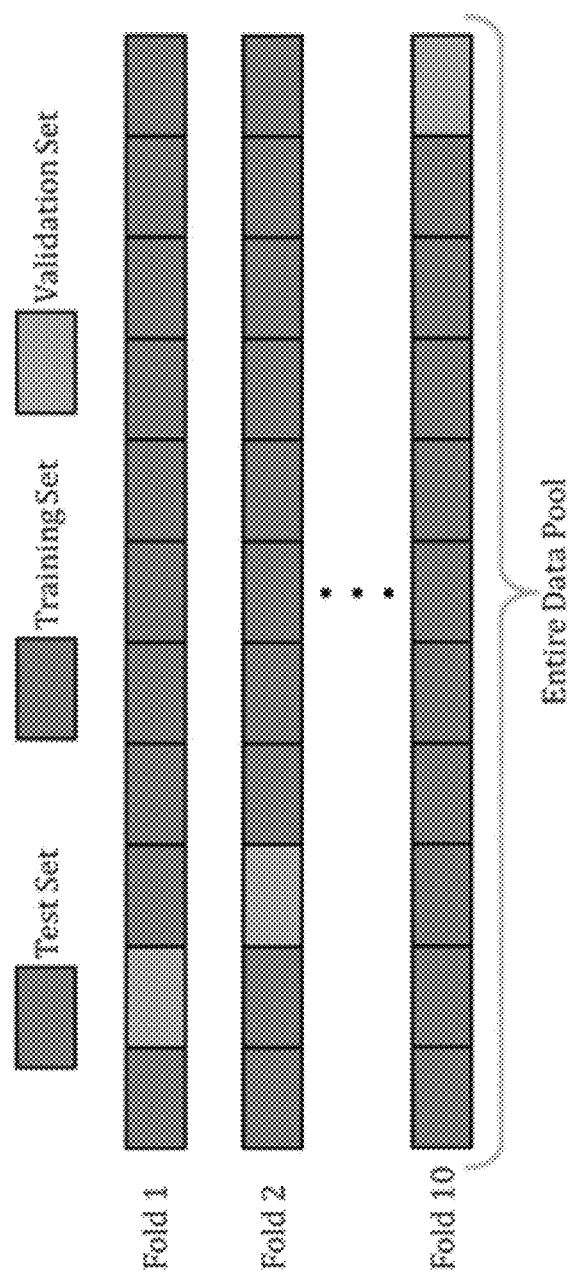
FIG. 11 is a block diagram illustrating 10-fold cross-validation, according to example embodiments.

To assess the overall performance of the model, 8 patients were selected as a test set, and then 10-fold cross-validation procedure was performed on the remaining 80 patients, as shown in FIG. 11. Each of the 10 folds divides the remaining 80 patients into 72 training patients and 8 validation patients. Ten separate U-net models are initialized, trained, and validated on a unique training and validation combination. Each fold produces a model that can predict a dose distribution from contours. From these 10 trained models, the system then take the best performance model, based on its validation loss, and evaluate this model on the test set.

For the remainder of the manuscript, some common notation will be used. D # is the dose that #% of the volume of a structure of interest is at least receiving. $V_{ROI}$ is the volume of the region of interest. For example, D95 is the dose that 95% of the volume of the structure of interest is at least receiving. $V_{PTV}$ is the volume of the PTV and $V_{\#\% \ ISO}$ is the volume of the #% isodose region.

To equally compare across the patients, all plans were normalized such that 95% of the PTV volume was receiving the prescription dose (D95). It should be noted that this is normalized differently than for training the model, which had normalized the plans by PTV mean dose. Normalizing by PTV mean dose creates a uniform dataset which is more likely to be stable for training, but plans normalized by D95 have more clinical relevance and value for assessment. All dose statistics will also be reported relative to the prescription dose (i.e. the prescription dose is set to 1). As evaluation criteria, dice similarity coefficients $$\left(\frac{2(A \cap B)}{A + B}\right)$$

of isodose volumes, structure mean and max doses, PTV D98, D99, $D_{max}$, PTV homogeneity $$\left(\frac{D2 - D98}{D50}\right),$$

van't Riet conformation number[42]

$$\left(\frac{(V_{PTV} \cap V_{100\% \ Iso})^2}{V_{PTV} \times V_{100\% \ Iso}}\right),$$

and the dose spillage R50

$$\left(\frac{V_{50\% \ Iso}}{V_{PTV}}\right),$$

were evaluated.

Five NVIDIA Tesla K80 dual-GPU graphics cards (10 GPU chips total) were used in this study. One GPU was used for training each fold of the 10-fold cross-validation. Training batch size was chosen to be 24 slices.

II.4: Results

Figure 12:
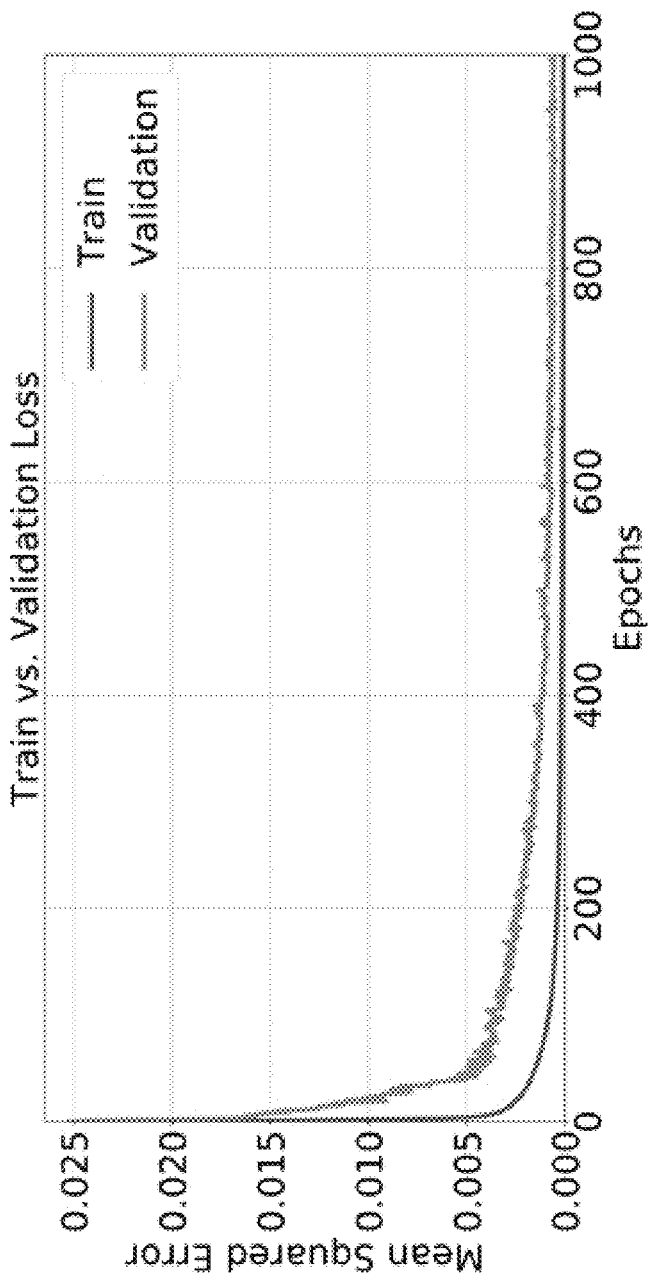
FIG. 12 is a chart plotting training versus validation loss as a function of epochs, according to example embodiments.

In total, models from all folds trained for 1000 epochs each, which took approximately 6 days on the 10 GPUs. A plot of training and validation loss from one of the folds is shown in FIG. 12 as an example The final average loss±standard deviation between all the folds is $(1.02\pm0.05)\times10^{-4}$ (training loss) and $(6.26\pm1.34)\times10^{-4}$ (validation loss). Of the 10 folds, the model from the $5^{th}$ fold performed the best with the lowest validation loss of $4.47\times10^{-4}$. This model was used to evaluate the dosimetric performance on the test set of patients.

TABLE 1

Average differences in mean and max dose with standard deviations.

$$\text{Average Absolute Dose Difference} \left| \frac{D_{True} - D_{Prediction}}{D_{Prescription}} \right| \times 100$$

mean value ± standard deviation

|  | Cross-Validation Results | | Test Results | |
|---|---|---|---|---|
|  | $D_{max}$ | $D_{mean}$ | $D_{max}$ | $D_{mean}$ |
| PTV | 1.41 ± 1.13 | 0.77 ± 0.58 | 1.80 ± 1.09 | 1.03 ± 0.62 |
| Bladder | 1.38 ± 1.17 | 2.38 ± 2.26 | 1.94 ± 1.31 | 4.22 ± 3.63 |
| Body | 1.45 ± 1.21 | 0.86 ± 0.42 | 1.80 ± 1.09 | 0.48 ± 0.35 |
| L Fem Head | 2.46 ± 2.56 | 1.16 ± 0.74 | 3.87 ± 3.26 | 1.79 ± 1.58 |
| R Fem Head | 2.42 ± 2.45 | 1.17 ± 0.88 | 5.07 ± 4.99 | 2.55 ± 2.38 |
| Rectum | 1.34 ± 1.02 | 1.39 ± 1.03 | 1.26 ± 0.62 | 1.62 ± 1.07 |

TABLE 2

True and predicted values for PTV statistics, homogeneity, van't Riet conformation number, and the high dose spillage, R50.

PTV Statistics, van't Riet Conformation Number, and Dose Spillage
mean value ± standard deviation

|  | Cross-Validation Results | | | Test Results | | |
|---|---|---|---|---|---|---|
|  | True Values | Pred Values | True − Pred | True Values | Pred Values | True − Pred |
| PTV D98 | 0.98 ± 0.01 | 0.98 ± 0.01 | −0.00 ± 0.01 | 0.98 ± 0.01 | 0.98 ± 0.01 | 0.00 ± 0.00 |
| PTV D99 | 0.97 ± 0.01 | 0.97 ± 0.04 | 0.00 ± 0.04 | 0.96 ± 0.01 | 0.97 ± 0.01 | 0.00 ± 0.01 |
| PTV $D_{max}$ | 1.08 ± 0.02 | 1.08 ± 0.02 | 0.01 ± 0.02 | 1.08 ± 0.01 | 1.07 ± 0.02 | 0.01 ± 0.02 |
| PTV Homogeneity | 0.09 ± 0.02 | 0.08 ± 0.03 | 0.01 ± 0.02 | 0.09 ± 0.01 | 0.07 ± 0.02 | 0.01 ± 0.02 |
| van't Riet Conformation Number | 0.88 ± 0.08 | 0.92 ± 0.04 | −0.04 ± 0.05 | 0.91 ± 0.02 | 0.90 ± 0.03 | 0.00 ± 0.02 |
| R50 | 4.45 ± 1.23 | 4.10 ± 1.14 | 0.35 ± 0.23 | 4.00 ± 0.37 | 3.98 ± 0.32 | 0.02 ± 0.21 |

Figure 13:
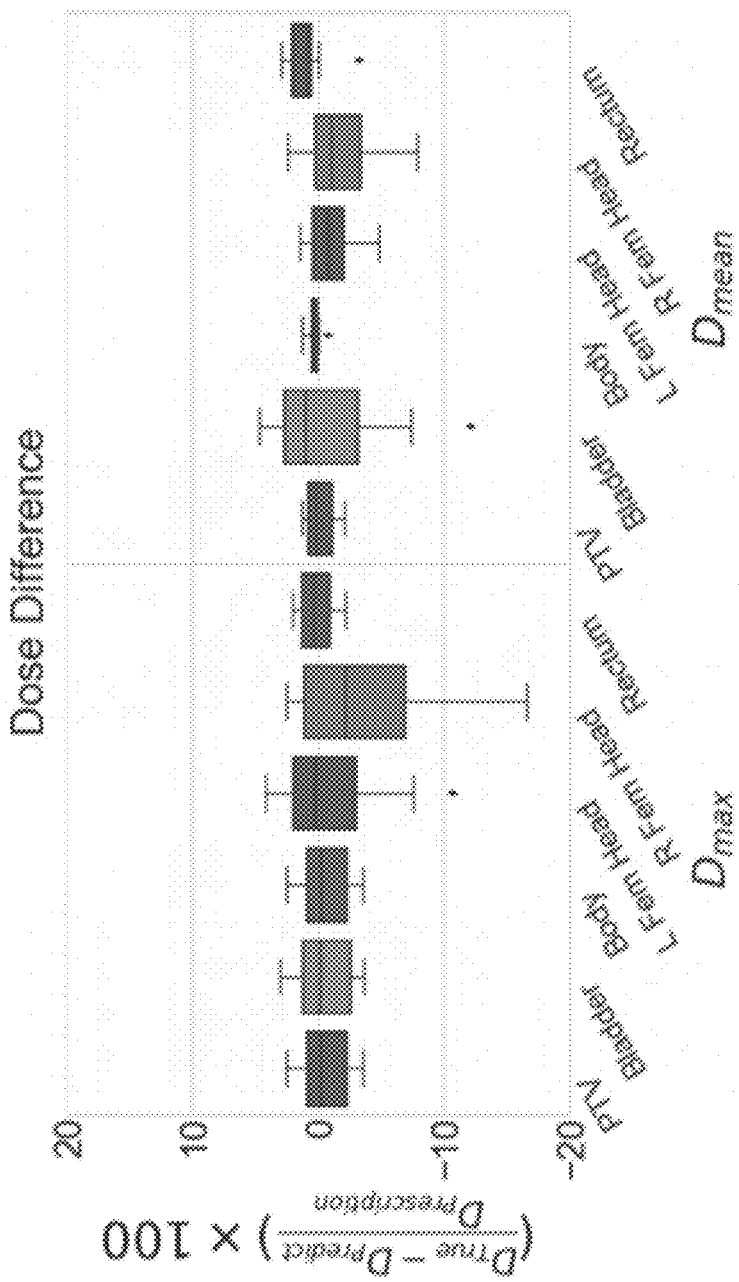
FIG. 13 is a box plot illustrating dose difference statistics, according to example embodiments.

A box plot of max and mean dose differences (True—Prediction) for the PTV and OARs for the test patient cases are shown in FIG. 13. On average, the U-net model is biased to slightly over-predict the mean and max doses. A full list of average absolute differences for both the cross validation and test data can be found in Table 1. Overall, the cross validation error is slightly less than the test error. For the test data, the PTV, body and rectum maintain a prediction accuracy of within 3% error. The bladder has a low max dose error of 1.9% but a larger error in the mean dose of 4.2%. The femoral heads have higher max dose errors but reduced mean dose errors of under 3%. Overall, the model is capable of accurately predicting $D_{max}$ and $D_{mean}$ within 5.1% of the prescription dose. In addition all of the PTV related dosimetric statistics, dose conformity, and the dose spillage, R50, are very well predicted by the network as shown in Table 2. The PTV coverage, PTV $D_{max}$, conformation number, and R50 have less than 1% error (calculated as $$\left| \frac{\text{True} - \text{Predicted}}{\text{True}} \right| * 100 \right).$$

Figure 14:
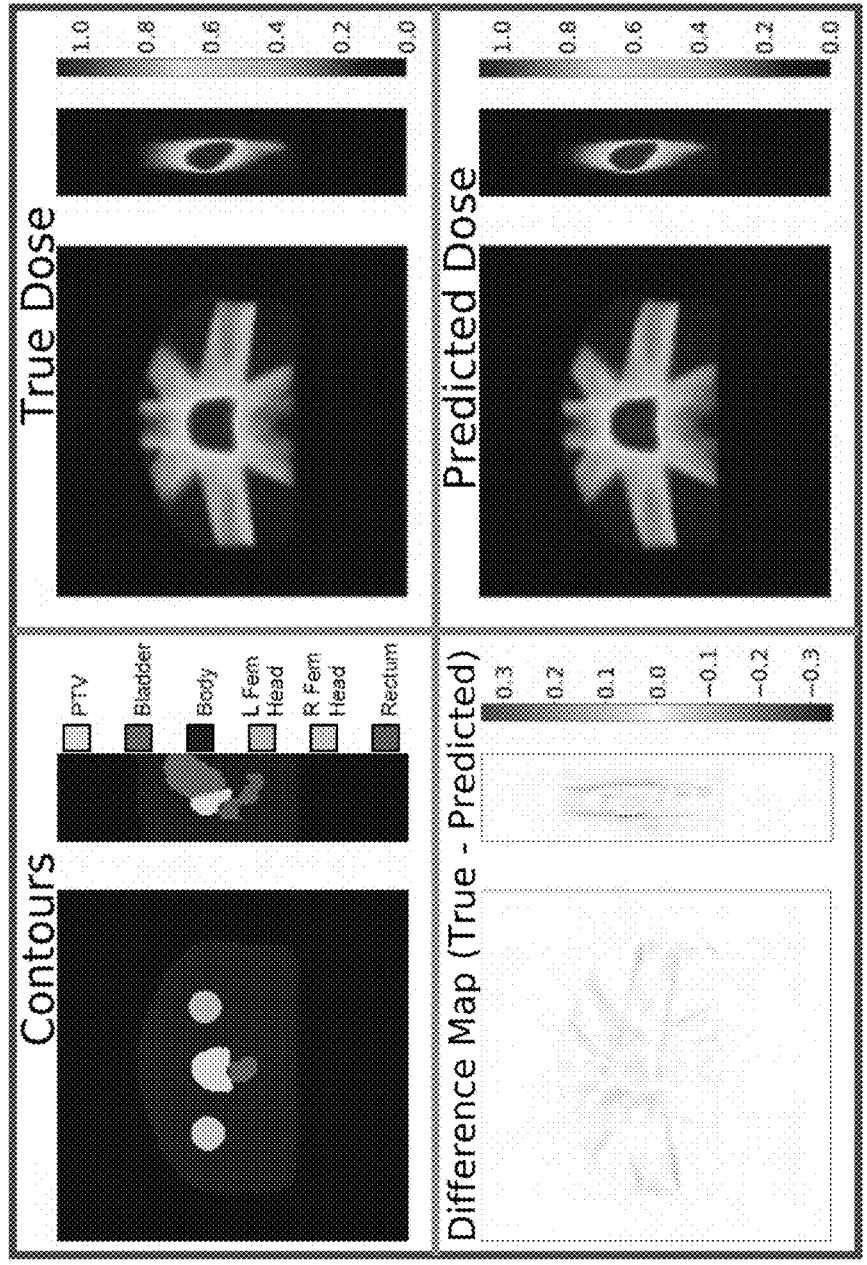
FIG. 14 is a block diagram illustrating contours of the planning target volume (PTV) and organs at risk (OAR), true dose wash, predicted dose wash, and difference map of an example patient, according to example embodiments.
Figure 15:
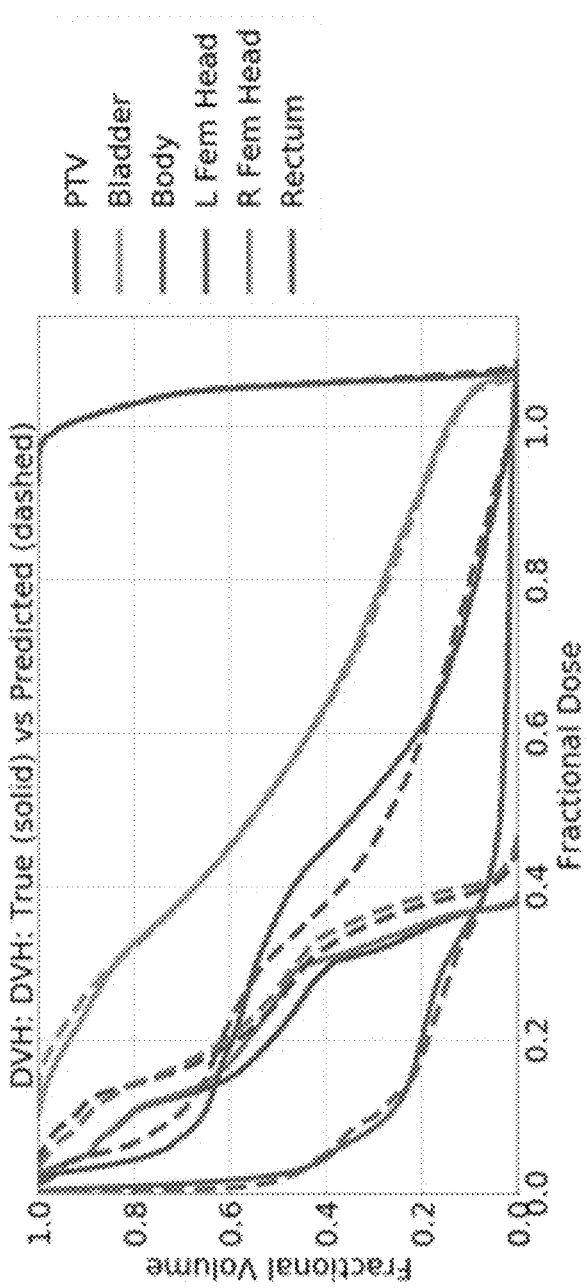
FIG. 15 is a block diagram illustrating a dose volume histogram comparing true dose and predicted dose, according to example embodiments.

As a typical prediction example from the U-net model, FIG. 14 shows the input contours, true and predicted dose washes, and a difference map of the two doses for one patient. On average, the dose difference inside the body was less than 1% of the prescription dose, shown in Table 1. FIG. 15 shows the DVH of one of the example test patients. Visually on the DVH, one can see that the U-net tends to predict a similar PTV dose coverage with minimal errors in the dose prediction to the OARs.

Figure 16:
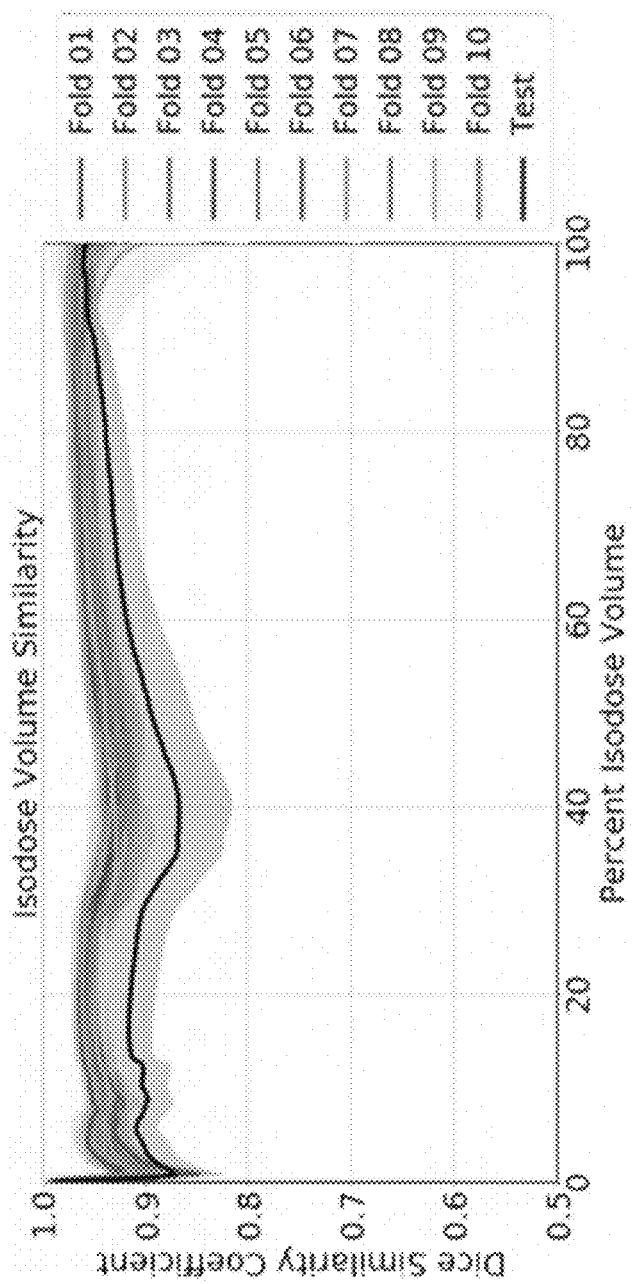
FIG. 16 is a chart comparing isodose volumes between a true dose and a predicted dose, according to example embodiments.

The plot of dice similarity coefficients of isodoses is shown in FIG. 16. Dice similarity coefficients range from 0 to 1, where 1 is considered a perfect match. The average dice similarity coefficient for the test data is 0.91 and for the cross-validation data is 0.95, a 4% difference. The isodose volume similarity expresses slight decreases in the dice coefficient near the 40% isodose volume. The loss in predictability at 40% is associated to the complicated details in the dose distribution along the beam paths in the normal tissue, which is generated during the fluence map optimization process.

Figure 17:
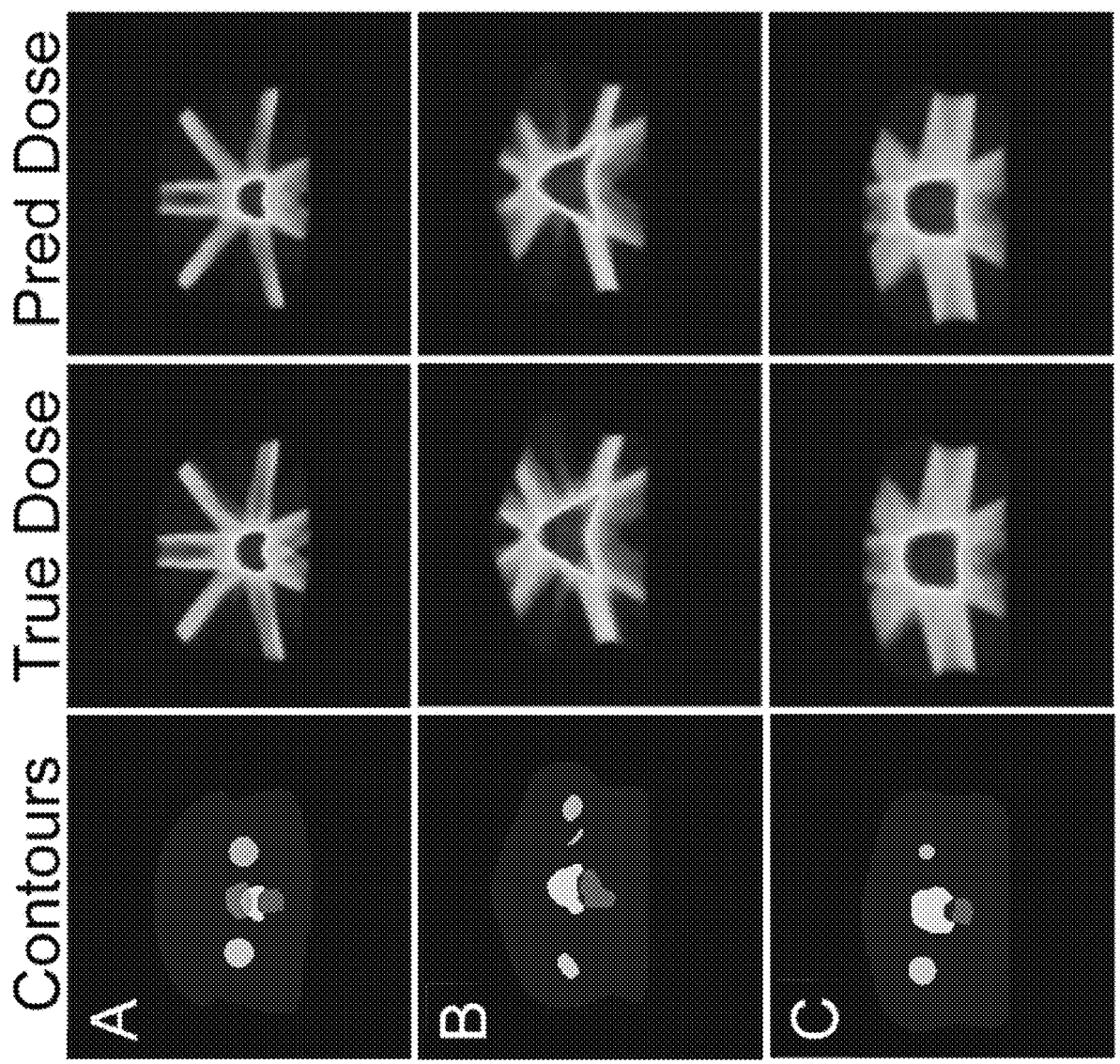
FIG. 17 is a block diagram illustrating exemplary dose predictions, according to example embodiments.

FIG. 17 shows some examples of dose prediction from the U-net on patients that have very diverse geometries. It can be visually seen that the U-net has learned to shape the dose based on the PTV and OARs sizes, locations, and shapes. The finer details of the dose distributions further away from the PTV have been predicted by the deep network model with relative high accuracy.

II.5: Discussion

This is the first fully 3D dose distribution prediction for prostate IMRT plans, thus making direct comparison to existing models difficult. The latest study by Shiraishi and Moore (Shiraishi, et al., *Medical physics*, 2016; 43(1):378-387) on knowledge based planning did investigate 3D dose prediction, but for prostate patients treated with VMAT. In addition, another cutting edge study by McIntosh and Purdie (McIntosh, et al., *IEEE Transactions on Medical Imaging*, 2016; 35(4):1000-1012) investigated 3D dose prediction using atlas regression forests. Because of the differing patient data base and treatment modalities/protocols, the results cannot be directly compared. It should be noted that Shiraishi and Moore's average prediction error was less than 8% using their method on their patients, and McIntosh and Purdie's study found the average dice coefficient to be 0.88 (range is from 0.82 to 0.93).

The 88 clinical prostate patients acquired in this study used a similar set of 7 beam angles and criteria for treatment, giving rise to some uniformity to the data that made it ideal as a test bed to investigate the feasibility for dose prediction using a deep learning model.

II.6: Conclusion

The above section described a novel application of the fully convolutional deep network model, U-net, for dose prediction. The model is able to take a prostate patient's contours and then predict a dose distribution by abstracting the contours into local and global features. Using the recited implementation of U-net, the system is able to accurately predict the dose of a patient, with average mean and max dose differences of all structures within 5.1% of the prescription dose. Isodose similarity evaluation reveals that the predicted dose isodose volumes match the true isodose volumes with the average dice coefficient of 0.91. In some embodiments, the model may further include in dose prediction for non-coplanar beam arrangements and accounting for physician preference. The immediate application of the dose prediction model is to guide clinical plan optimization to reduce treatment planning time and to maintain high quality plans. The long-term objective is to incorporate the learning dose prediction model into an artificially intelligent radiation therapy treatment planner Section III: Lung IMRT Patients The use of neural networks to directly predict three-dimensional dose distributions for automatic planning is becoming popular. However, the existing methods use only patient anatomy as input and assume consistent beam configuration for all patients in the training database. The purpose of this work is to develop a more general model that considers variable beam configurations in addition to patient anatomy to achieve more comprehensive automatic planning with a potentially easier clinical implementation, without the need to train specific models for different beam settings.

The proposed anatomy and beam (AB) model is based on newly developed deep learning architecture, hierarchically densely connected U-Net (HD U-Net), which combines U-Net and DenseNet. In some embodiments, the AB model contains 10 input channels, one for beam setup and the other 9 for anatomical information (PTV and organs). The beam setup information is represented by a 3D matrix of the non-modulated beam's eye view ray-tracing dose distribution. A set of images from 129 patients with lung cancer treated with IMRT with heterogeneous beam configurations (4 to 9 beams of various orientations) may be used for training/validation (100 patients) and testing (29 patients). Mean squared error was used as the loss function. The model's accuracy may be evaluated by comparing the mean dose, maximum dose, and other relevant dose-volume metrics for the predicted dose distribution against those of the clinically delivered dose distribution. Dice similarity coefficients were computed to address the spatial correspondence of the isodose volumes between the predicted and clinically delivered doses. The model was also compared with the anatomy only (AO) model, which does not consider beam setup information and uses only 9 channels for anatomical information.

The AB model outperformed the AO model, especially in the low and medium dose regions. In terms of dose volume metrics, AB outperformed AO is about 1-2%. The largest improvement was found to be about 5% in lung volume receiving a dose of 5 Gy or more ($V_5$). The improvement for spinal cord maximum dose was also important, i.e., 3.6% for cross-validation and 2.6% for testing. The AB model achieved Dice scores for isodose volumes as much as 10% higher than the AO model in low and medium dose regions and about 2% to 5% higher in high dose regions.

The AO model, which does not use beam configuration as input, can still predict dose distributions with reasonable accuracy in high dose regions but introduces large errors in low and medium dose regions for IMRT cases with variable beam numbers and orientations. The proposed AB model outperforms the AO model substantially in low and medium dose regions and slightly in high dose regions by considering beam setup information through a cumulative non-modulated beam's eye view ray-tracing dose distribution. This new model represents a major step forward towards predicting 3D dose distributions in real clinical practice, where beam configuration could vary from patient to patient, from planner to planner, and from institution to institution.

III.1: Introduction

Current treatment planning systems for radiation therapy use advanced software to solve an inverse optimization problem,' which aims to determine the optimal treatment and machine parameters from an a priori specified set of dose objectives for the target and organs at risk (OARs). The fastest software can provide a solution to this problem within seconds. However, the medical physicist or dosimetrist still fine tunes the dose objectives manually until the desired dose distribution is achieved. This results in a heuristic and time-consuming process (from several hours to days), which entails a variability in plan quality that depends on factors such as the time available to generate the plan, the institution guidelines, or the planner's skills. This variability may lead to suboptimal plans that can compromise the final treatment outcome. Furthermore, the extended treatment planning time greatly hinders the implementation of adaptive strategies[8,9] and may delay treatment delivery, both of which have a negative impact on tumor control and patients' quality of life.

To overcome these problems, the research community has concentrated its efforts on reducing this manual component by automating the treatment planning process. Several groups have come up with powerful solutions that can be classified into two branches. The first branch, here referred to as objective-based planning (OBP), relies on optimization algorithms that adjust pre-set objectives to achieve the established clinical goals, with well-known implementations including the in-house software Erasmus-iCycle[14] or the Auto-Planning Engine[15] commercialized by Pinnacle (Philips Radiation Oncology, Fitchburg, Wis.), among others.[16-19] The second branch, what is called knowledge-based planning (KBP), uses a library of plans from previous patients to predict dose volume objectives for the new patient[20-23] and is best exemplified by the popular commercial solution RapidPlan (Varian Medical Systems, Palo Alto, Calif.). All these alternatives for automatic planning have been tested in different patient populations and anatomical sites, and they have sped up the planning process considerably (time reduction of 70-90%) for both intensity modulated radiation therapy (IMRT) and volumetric arc therapy (VMAT)[24-26] while generating high-quality plans with less human intervention.[27-31]

Even with these advancements, the OBP and KBP methods still suffer from two main drawbacks. First, they use dose volume objectives, either zero-dimensional (dose volume points) or one-dimensional (dose volume histogram, DVH), for the delineated structures. These dose volume objectives are insensitive to spatial variations of the dose within the structures delineated and blind to those structures that are not delineated. This could lead to suboptimal plans, in terms of the spatial distribution of the dose, and may require post-processing steps in which the user manually adds planning-aid structures and re-optimizes to control these spatial features. Second, both OBP and KBP strategies still require substantial human intervention to define certain parameters needed to create the model, such as the target and OAR optimization goals for OBP[14, 29, 32] or handcrafted features that serve to match the actual patient to those in the library of patients for KBP.[20, 32, 33] Including spatial dose information[34-42] and completely removing manually extracted features are necessary to achieve a more individualized and comprehensive automatic planning The recent evolution of deep learning methods has motivated the use of convolutional neural networks (CNN) to predict patient-specific voxel-wise dose distributions from anatomical information (i.e., contours and/or CT), either in a slice-by-slice manner (2D)[39-41, 43] or directly as a 3D matrix.[38, 42, 44] The predicted dose distribution can later be used as an objective to automatically generate a treatment plan.[37, 45] These methods completely eliminate dependence on handcrafted features by allowing the deep network to learn its own features for preclicion,[38-42] and the results reported so far are very promising. However, the performance of these deep learning methods for voxel-wise dose prediction strongly depends on the database used for training, requiring users to carefully choose patients with consistent beam configurations, such as VMAT[38] or IMRT, with fixed and equally spaced beams.[39-41] This ensures an accurate dose prediction for cases with similar beam settings, but it impedes the generalization of the model to more heterogeneous beam configurations, which is crucial for IMRT treatments where the beam number and orientations could vary greatly from patient to patient and from institution to institution. As a result, the clinical implementation of automatic planning based on this type of model appears to be unfeasible, since it would require generating specific models for each individual beam arrangement.

The current models[38-42] use only anatomical information as inputs to the CNN. In this work, the value of including both anatomical and beam setup information in the network, to build a single model that is robust to variable beam configurations is investigated. This general model can realize the full potential of deep neural networks for dose prediction, bringing closer the clinical implementation of automatic planning based on this type of method.

III.2: Materials and Methods
III.3(a): Model Architecture

The model used for dose prediction was developed in-house, and its architecture is based on the popular U-Net, published by Ronneberger et al. in 2015.[46] The U-Net is a type of CNN that belongs to the class of fully convolutional networks,[47] and it can include both local and global features from the input images to generate a pixel-wise (two-dimensional, 2D) prediction. The group has previously used this architecture to generate 2D dose predictions for prostate patients in a slice-by-slice manner.[39] However, to avoid errors in the superior and inferior borders of the planning target volume (PTV) and OARs inherent to this 2D strategy, the system implements a three-dimensional (3D) variant of the classical 2D U-Net. Since the computational load increases with the dimensionality, the group created different models to achieve an accurate and efficient 3D dose prediction. These models are described in detail elsewhere[38] and have been tested for head and neck patients. The best performance was achieved by a model that combined two recently proposed architectures: DenseNet by Huang et al. in 2017[48] and V-Net by Milletari et al. in 2016.[49] The DenseNet densely connects its convolutional layers in a feed-forward fashion, using the feature-maps of all preceding layers as inputs for the current layer. This reduces the vanishing-gradient problem, enhances feature propagation and reuse, and decreases the number of trainable parameters. The drawback of this approach is its increased memory usage, a consequence of the dense connection between layers. To maintain a reasonable RAM usage, the DenseNet is modified to skip some connections between groups of layers, following the work of Milletari et al. In addition, Huang et al.[48] found that DenseNet architectures could utilize considerably fewer trainable parameters than non-densely connected architectures, yielding better RAM usage and better generalization of the model that outweighs the greater RAM consumption of the dense connections themselves. In particular, the convolutional layers in the model are densely connected within levels of the same resolution in the U-Net, between each max pooling and up-sampling operation. Each of these levels may be referred to as a "hierarchy." Accordingly, the name of this network is "Hierarchically Densely Connected U-Net" ("HD U-Net"[38]). This HD U-Net combines DenseNet's efficient feature propagation and reuse with U-Net's ability to infer the global and local image information, while maintaining a reasonable memory usage. The detailed architecture of the HD U-Net used in this study is presented in FIG. 18, and the technical elements regarding the operations between layers have been previously described elsewhere.[38, 44] The HD U-Net uses the Adam optimization algorithm to minimize the mean squared error (MSE) between the predicted dose ($D_{pred}$) and the clinically delivered dose ($D_c$) during training, i.e., $$MSE = \frac{1}{n}\sum_{i=1}^{n}(D_{pred}^i - D_c^i)^2,$$

where i is the index of the voxel and n is the total number of voxels. The network combines the three operations in the legend: dense convolution, dense downsampling, and U-Net upsampling. The dense convolution uses a standard convolution with the well-known Rectified Linear Unit (ReLU[50]) as its activation function, followed by a concatenation of the previous feature map. The dense downsampling uses a strided convolution and ReLU to compute a new feature map with half of the former resolution. Max pooling is applied to the previous feature map, which is then concatenated to the new feature map. The U-Net upsampling consists of upsampling, convolution, and ReLU, followed by a concatenation of the feature map on the other side of the "U." The activation function at the last output layer was also ReLU. No regularization method was applied during training, i.e. the dropout rate was set to zero, and there was no batch normalization.

The model proposed in this work, called the Anatomy and Beam (AB) model, considers both patient anatomy and beam setup information as inputs. Hence, it contains 10 input channels (FIG. 18): one channel for beam setup information and 9 channels for anatomical information. The beam setup information is represented by an approximate 3D cumulative dose distribution (ray-tracing style, beam's eye view, and non-modulated) from all involved beams (see Section 2.D). The anatomical information comprises 3D binary matrices or masks, i.e., the prescription dose (60 Gy) for voxels inside and 0 for voxels outside the PTV, and 1 for voxels inside and 0 for voxels outside each of the 8 relevant OARs for lung treatment planning: body, heart, esophagus, spinal cord, right and left lungs, both lungs minus the target, and carina. For some patients, certain organs are not delineated, and therefore, the corresponding channel receives an empty entry.

III.2(b): Patient Database

The database consisted of images from 129 patients with lung cancer treated with IMRT at UT Southwestern Medical Center, which involved four different treating physicians. The database was heterogeneous in terms of number of beams (4 to 9 beams, all coplanar), beam orientation (FIG. 19 and FIG. 20), and beam energy (6 and 10 MV). The clinically delivered dose and the contours for each patient were extracted from two different treatment planning systems: Pinnacle V8.0-V9.6 (Philips Radiation Oncology Systems, Fitchburg, Wis.) for patients treated before 2017 and Eclipse V13.7-V15.5 (Varian Medical Systems, Palo Alto, Calif.) for patients treated after 2017. All plans were created and calculated with heterogeneity correction. The target dose prescription for all patients was 60 Gy, delivered with two different fractionation protocols: 4 Gy×15 fractions and 2 Gy×30 fractions. The original IMRT dose and the contour masks for all patients were resampled to have a voxel resolution of 5×5×5 mm³.

III.2(c): Model Performance

Figure 19:
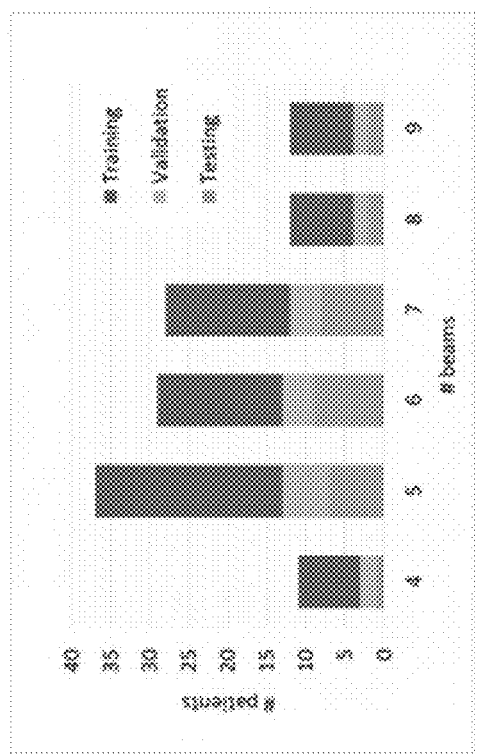
FIG. 19 is a chart illustrating beam orientation, according to example embodiments.
Figure 20:
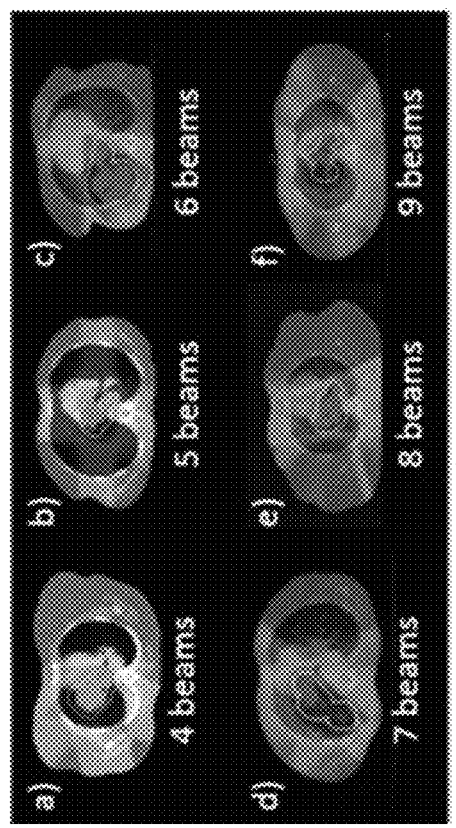
FIG. 20 is a block diagram illustrating beam orientation, according to example embodiments.

To evaluate the model's performance and stability, the database was divided into two sets: 1) 100 patients for training and cross-validation (FIG. 19, upper and middle bars), and 2) 29 patients for testing (FIG. 19, lower bars). A 5-fold cross-validation procedure was applied to the 100 patient set, which was itself split into 80 patients for training and 20 patients for validation (FIG. 19), alternating the latter along the 5 folds. When partitioning the dataset, the number of patients per beam configuration were balanced (or substantially balanced) in the three sets: training, validation, and testing (FIG. 19). The number of patients per beam configuration class was the same for each cross-validation fold. At every iteration, the network weights were updated based on the 80 training patients, and the loss function (MSE) was computed on the validation set. A different numbers of iterations (epochs), from 100 to 1000, were investigated to find the best trade-off between optimality and training time. Since different MSE values might not directly translate into the same dose distribution quality, relevant DVH metrics were also computed and analyzed to decide the optimal number of epochs to use. Once this optimal number of epochs was found (i.e., the clinical metrics did not improve with further training), the final model was selected as the one that corresponded to the iteration with the lowest validation loss, to avoid overfitting to the training data.[51] This process as repeated for each fold, generating 5 final models that were then evaluated in the testing dataset. All these operations were performed on an NVIDIA TESLA K80 GPU with 12 GB dedicated RAM.

The AB model was compared with previous work and the current state-of-the-art, the Anatomy Only (AO) model, which contains 9 input channels for the PTV and the organs, without the beam setup information. Accuracy of the two methods (AB and AO) were evaluated by computing the average error between the predicted ($D_p$,AB and $D_p$,AO) and clinically delivered (Dr) dose distributions on the mean and maximum dose values for different organs. The average error on relevant DVH metrics was analyzed, such as the lung volume receiving a dose of at least 20 Gy ($V_{20}$) or the dose delivered to 95% of the target volume ($D_{95}$). All these values are presented as a percentage of the prescribed target dose (60 Gy). For easier comparison among patients, all doses ($D_{p,AB}$, $D_{p,AO}$, and $D_c$) were normalized to have an average dose inside the PTV equal to the prescription dose, i.e., $D_{mean}$=60 Gy. This normalization point serves only as a fixed point for comparison, but the user can later shift the dose to any other convenient reference, such as the $D_{95}$ of PTV equal to the prescription dose, which is often used in the clinic. The target dose homogeneity was evaluated using the following equation for the homogeneity index: HI=($D_2$−$D_{98}$)/$D_{50}$. In addition, Dice similarity coefficients (DSC) of the isodose volumes from 5% to 95% of the prescription dose were computed for $D_{p,AB}$ and $p_{p,AO}$ and compared with those for $D_c$ to evaluate the accuracy of the spatial distribution of the doses predicted by the two models. For this purpose, three-dimensional binary masks were computed for each isodose volume containing all voxels with a dose greater than or equal to the N % of the prescription dose, in both the predicted dose (Y) and the clinically delivered doses (X). Once these three-dimensional binary masks (X and Y) were computed, the following operation was performed:

$$DSC = \frac{2|X \cap Y|}{|X|+|Y|}.$$

III.2(d): Beam Configuration Representation

The proposed architecture aims to improve the accuracy and robustness of dose prediction against a database that is heterogeneous with regard to beam arrangement. The key here is to best represent the beam configuration without greatly complicating the model architecture and, in the meantime, to provide valuable information for accurate dose distribution prediction. Ideally, a good representation should be in the dose domain and contain information about beam energy, beam aperture, and heterogeneity correction, while being computationally inexpensive. For this purpose, a cumulative dose distribution computed using a ray-tracing type of algorithm for all beams in the plan, without modulation, and with apertures conformal to the PTV in beam's eye view was used. A fluence-convolution broad-beam (FCBB) dose calculation method was used, which is a modified ray-tracing algorithm, involving a 2D convolution of a fluence map with a lateral spread function followed by ray-tracing based on the central axis of the beam. In some embodiments, a dummy homogeneous fluence map (i.e., all weights equal to 1) with the aperture of the PTV projection in beam's eye view plus an isotropic margin of 5 mm is generated for each beam angle. The FCBB dose engine then uses this dummy fluence map as input, together with percentage depth dose (PDD) profiles from the Golden Beam Data (GBD) provided by Varian Medical Systems, Inc. (Palo Alto, Calif.), to compute the non-modulated dose per beam. The algorithm can generate the dose per beam in fractions of a second. Since the final computed dose per beam is given in arbitrary units, a normalization is performed after summing up all beams to make the mean dose inside the PTV equal the prescription dose. After adding up the dose corresponding to every beam, all voxels inside the PTV are overwritten to have a dose equal to the prescription dose.

Note that this study assumes that the number of beams and their orientations have been previously determined by the planner, as is commonly done in clinical practice, or will eventually be given by any beam angle optimization algorithm.

III.2(e): Additional Testing

To further test the performance of the AB model for patients with beam configurations other than the ones included in the database (FIG. 19), three more patients were used with the following beam setups: patient #1) three coplanar beams, patient #2) eleven coplanar beams, and patient #3) ten non-coplanar beams. The system evaluated and compared the AB and AO models on these three patients, using the same criteria as listed in section 2.C., i.e. relevant DVH metrics, HI, and Dice coefficients for the isodose volumes.

III.3: Results

The results for the average absolute error and its standard deviation (SD) on the mean and maximum dose for the target and OARs are presented in FIG. 21 for cross-validation (average prediction on the validation set for all 5 folds) and in FIG. 22 for testing (average prediction on the test set for all 5 folds). In both cases, the error on the mean and maximum doses predicted by the AB model was (on average) around 1% lower than on the AO model. The mean dose error value for the test set, averaged across all organs, was 2.28±2.01% on the AO model and 1.39±1.27% on the AB model. Likewise, the mean error on the maximum dose for the test set, averaged across all organs, was 3.97±4.73% for the AO model and 2.85±3.06% for the AB model. The biggest difference was found for the spinal cord maximum dose, where the AB model's prediction error was up to 3.6% lower for cross-validation and 2.6% lower for testing than the AO model's. Table 1 reports some relevant DVH metrics commonly used in the clinic to evaluate lung IMRT treatments, predicted from the two models. Again, the AB model outperformed the AO model, with better prediction accuracy for all the DVH metrics considered. Although the difference in the mean average error for most metrics is rather low (around 1-1.5%), for other metrics such as the lung V20 or V5, the error was up to 2% and 5% lower, respectively. The spinal cord $D_2$ was also substantially lower (around 3%).

The two models predicted the dose distribution in the target volume with equivalent accuracy, with homogeneity index (HI, mean±SD) equal to 0.11±0.02 for the AO model and 0.08±0.02 for the AB model, versus 0.09±0.04 for the clinical doses, for cross-validation. Similar results were obtained for testing: HI equal to 0.10±0.03 for the AO model and 0.08±0.02 for the AB model, versus 0.09±0.03 for the clinical doses.

Figure 23:
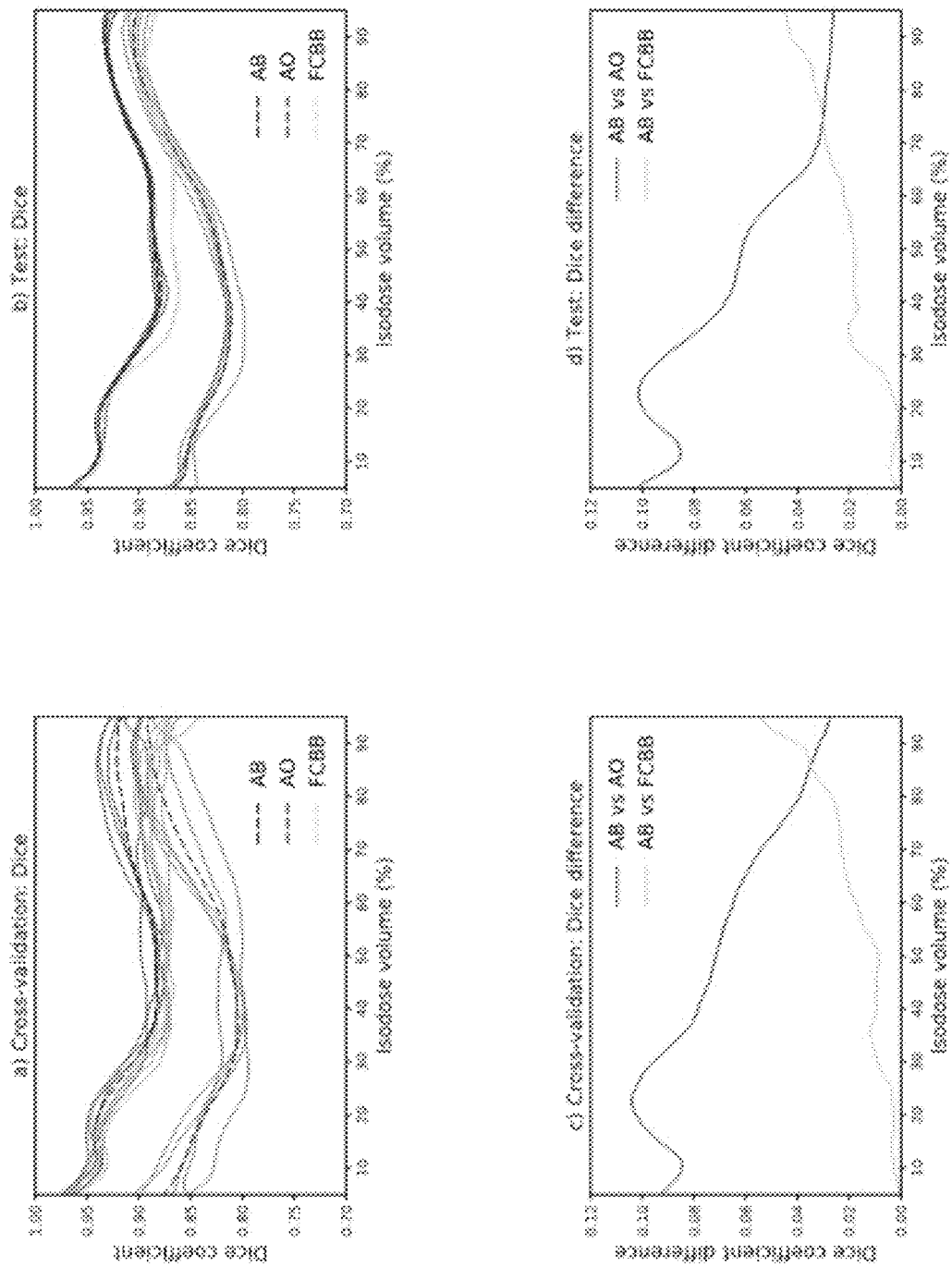
FIG. 23 are charts illustrating dice coefficient (upper) and dice coefficient difference (lower), according to example embodiments.

Dice similarity coefficients for the isodose volumes in $D_c$ versus $D_{p,AB}$ (blue) and $D_{p,AO}$ (red) are presented in FIG. 23. The AB model clearly outperformed the AO model, with most isodose volumes having a Dice coefficient equal to or greater than 0.9, for both cross-validation and testing. In particular, the AO model showed a poor accuracy for the isodose volumes in the medium to low dose region, i.e., Dice <0.9 for the isodose volumes up to 60-70% of the prescription dose, while the AB model achieves a Dice about 10% higher in the same region. In contrast, both models predicted the high dose region (from 80% isodose volume onwards) with comparable accuracy, though the AB model was still slightly superior, with Dice coefficients up to 2.5-5% higher than in the AO model. The lowest prediction accuracy occurs around the 40% isodose volume for both $D_{p,AB}$ and $D_{p,AO}$, but this effect appears to be much more pronounced in the AO model. In addition, the color-wash band representing the standard deviation of the Dice coefficient across all patients is narrower for the AB model for both cross-validation and testing, indicating a more stable model.

FIG. 23 also includes the Dice similarity coefficients for the isodose volumes in $D_c$ versus the input channel containing the beam representation for the AB model, i.e., the accumulated FCBB dose for all beams with the overwritten values inside the PTV equal to the prescription dose (Section 2.D). The FCBB dose alone seems to be an excellent approximation of $D_c$ in the low and medium dose regions, with a Dice value of about 0.9. The difference between the prediction from the AB model and its input channel is nearly zero up to the 20% isodose volume, at which point it starts to increase (FIG. 23.c and FIG. 23.d, yellow curve). This indicates that the AB model uses the input channel information as it is, without further modification, and learns how to include the modulation in the dose for each beam from the 20% isodose volume onwards.

Figure 24:
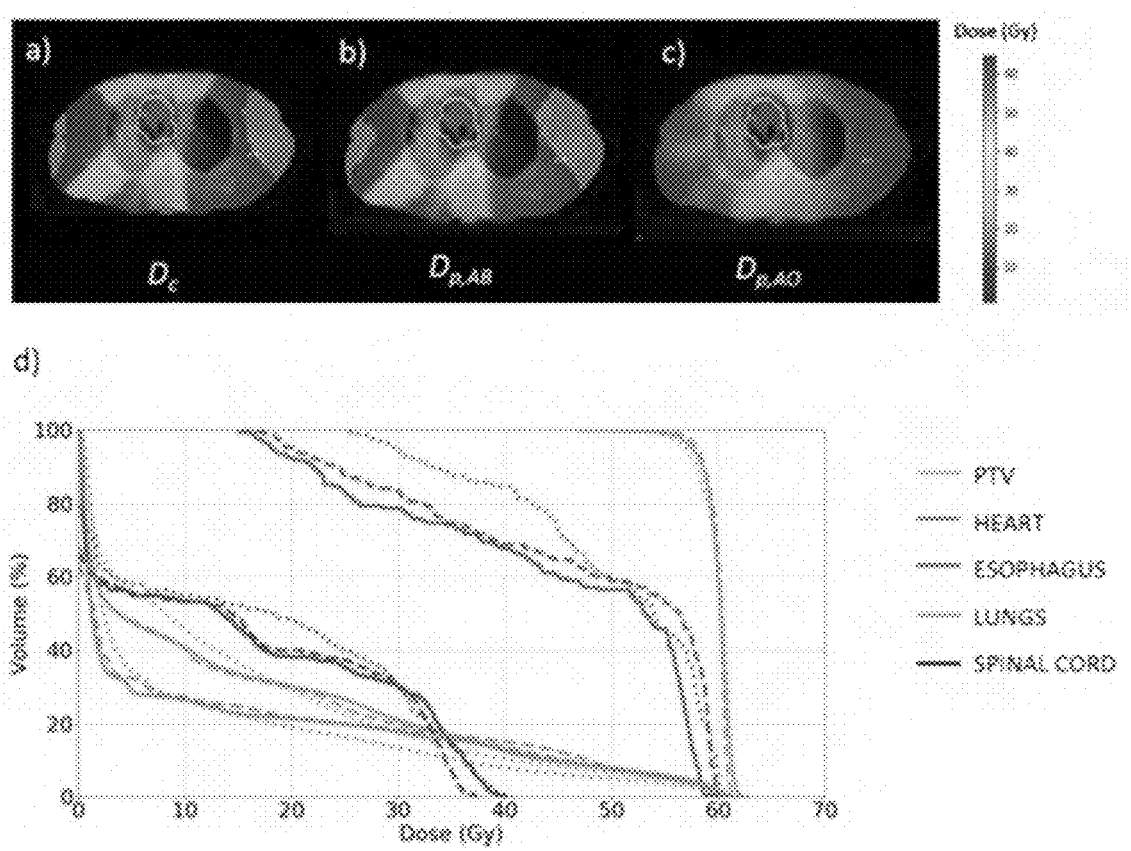
FIG. 24 is a block diagram illustrating an axial slice at the center of the target volume, according to example embodiments.

To illustrate the three-dimensional dose distribution predicted by the two models, the system generates and presents the results for one of the test patients in FIG. 24: an axial slice located at the center of the target, as well as the corresponding DVH for $D_c$, $D_{p,AB}$, and $D_{p,AO}$. The rest of the patients are not presented here due to limited space in the manuscript, but the behavior is similar for all of them: the AO model predictions show a very isotropic dose gradient that uniformly decreases from the target to the edge of the body, while the AB model is able to capture the dose features along the beam path due to the additional beam setup information.

Figure 25:
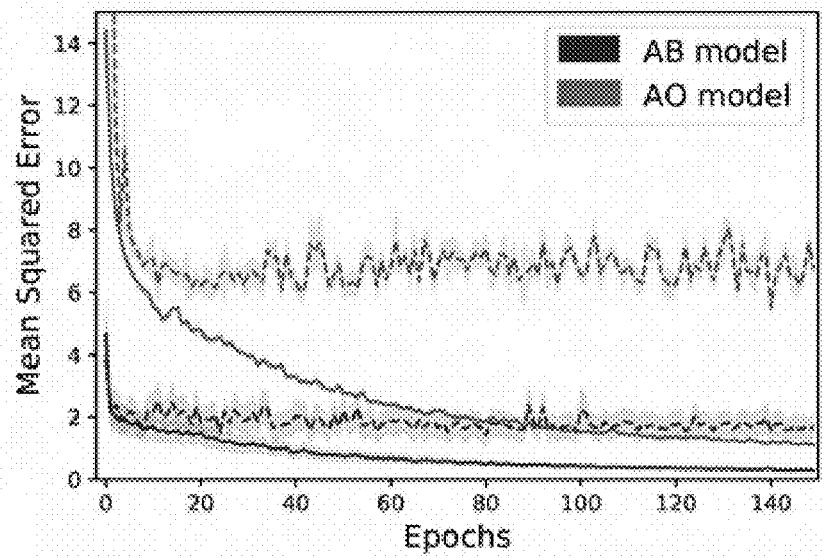
FIG. 25 is a chart illustrating a loss function evaluation for training and validation sets, according to example embodiments.

The two models were trained across 150 epochs, which took about 15 hours in both cases. Additional training for a larger number of epochs was investigated but did not result in any improvement of the clinical DVH metrics under evaluation. The average prediction times and their standard deviations were 11.42±0.12 s per patient for the AO model and 11.66±0.14 s for the AB model, using one NVIDIA Tesla K80 card. The convergence of the two models is presented in FIG. 25. The initial mean squared error for training and validation is much lower in the AB model (<5) than in the AO model (>14). This indicates that the prediction from the AB model is closer to the ground truth from the beginning, thanks to the extra input channel containing the beam setup information.

TABLE 1

Mean absolute error and its standard deviation (mean ± SD) for relevant DVH metrics on the target and on several organs for cross-validation (average prediction on the validation set for all 5 folds), and testing (average prediction on the test set for all 5 folds), for the AO and AB models. The values are expressed as percentage of the prescription dose ($D_{pre}$ = 60 Gy) for the metrics reporting the dose received by x % of volume ($D_x$), and as absolute difference for the metrics reporting the volume (in %) receiving a dose of y Gy ($V_y$).

Mean absolute error for DVH metrics

| | | Cross-validation (mean ± SD) | | Testing (mean ± SD) | |
| --- | --- | --- | --- | --- | --- |
| | | AO model | AB model | AO model | AB model |
| PTV | $D_{99}$ (% of $D_{pre}$) | 3.36 ± 3.24 | 2.70 ± 3.06 | 3.50 ± 2.96 | 2.54 ± 2.56 |
| | $D_{98}$ (% of $D_{pre}$) | 2.61 ± 2.15 | 1.95 ± 2.09 | 2.61 ± 2.20 | 1.71 ± 1.73 |

TABLE 1-continued

Mean absolute error and its standard deviation (mean ± SD) for relevant DVH metrics on the target and on several organs for cross-validation (average prediction on the validation set for all 5 folds), and testing (average prediction on the test set for all 5 folds), for the AO and AB models. The values are expressed as percentage of the prescription dose ($D_{pre}$ = 60 Gy) for the metrics reporting the dose received by x % of volume ($D_x$), and as absolute difference for the metrics reporting the volume (in %) receiving a dose of y Gy ($V_y$).

Mean absolute error for DVH metrics

|  |  | Cross-validation (mean ± SD) | | Testing (mean ± SD) | |
| --- | --- | --- | --- | --- | --- |
|  |  | AO model | AB model | AO model | AB model |
| Esophagus | $D_{95}$ (% of $D_{pre}$) | 1.80 ± 1.25 | 1.10 ± 0.86 | 1.92 ± 1.34 | 1.08 ± 0.96 |
|  | $D_5$ (% of $D_{pre}$) | 0.97 ± 0.83 | 0.81 ± 0.75 | 1.10 ± 1.50 | 0.94 ± 0.74 |
|  | $D_2$ (% of $D_{pre}$) | 5.39 ± 7.13 | 4.10 ± 4.61 | 6.04 ± 6.23 | 4.74 ± 4.85 |
|  | $V_{40}$ (% of volume) | 4.99 ± 5.57 | 3.25 ± 3.77 | 4.74 ± 5.09 | 3.58 ± 4.90 |
|  | $V_{50}$ (% of volume) | 4.94 ± 5.45 | 3.65 ± 4.31 | 4.14 ± 4.09 | 2.56 ± 2.94 |
| Heart | $V_{35}$ (% of volume) | 3.40 ± 7.78 | 2.48 ± 6.29 | 3.32 ± 5.41 | 2.57 ± 4.76 |
| Spinal cord | $D_2$ (% of $D_{pre}$) | 10.10 ± 7.82 | 6.74 ± 6.10 | 7.64 ± 7.12 | 5.05 ± 4.10 |
| Lungs | $D_{mean}$ (% of $D_{pre}$) | 2.21 ± 1.61 | 1.12 ± 1.00 | 2.04 ± 1.68 | 1.13 ± 0.94 |
|  | $V_5$ (% of volume) | 7.48 ± 6.14 | 2.60 ± 3.37 | 8.20 ± 7.06 | 2.67 ± 2.61 |
|  | $V_{20}$ (% of volume) | 3.96 ± 3.66 | 2.18 ± 2.42 | 4.66 ± 4.51 | 2.67 ± 2.87 |

Figure 26:
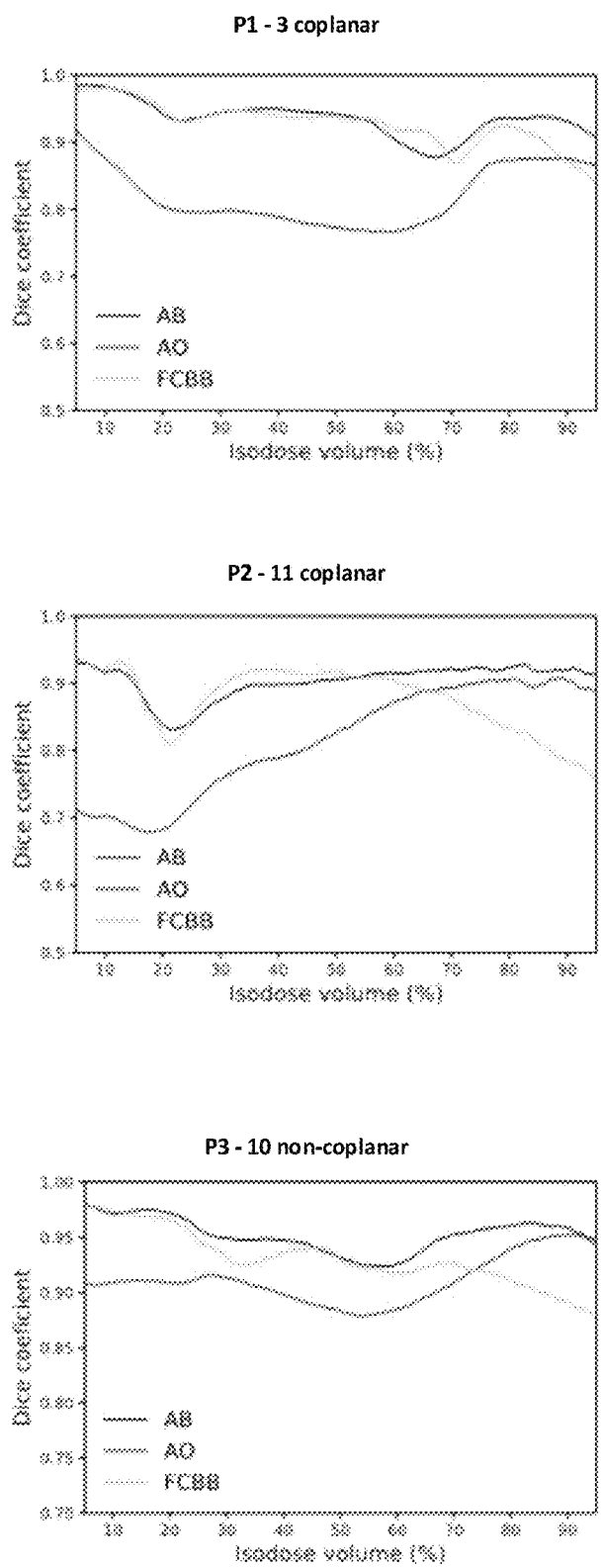
FIG. 26 are charts illustrating dice similarity coefficients of isodose volumes of the prescription dose, according to example embodiments.
Figure 27:
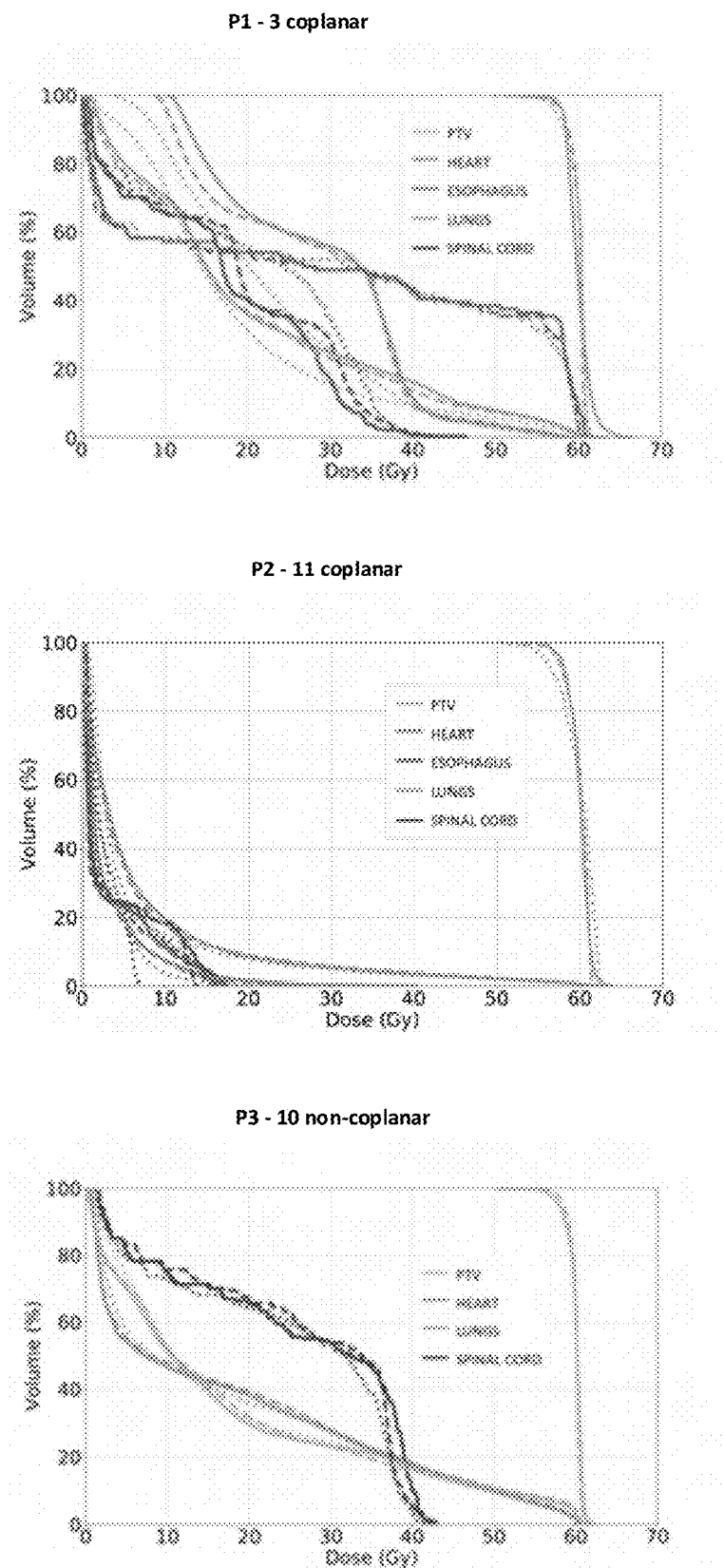
FIG. 27 are charts illustrating dose volume histograms for three patients, according to example embodiments.

The system also tested and analyzed the AB and AO models for three additional patients with beam configurations that had not been included in the initial database used for the study (129 patients, treated with 4 to 9 beams). The absolute mean error (over all 5 folds) on relevant DVH metrics for the doses predicted with the AB ($D_{p,AB}$) and AO models ($D_{p,AO}$) for these three patients are presented in Table 2. The AB model had lower prediction errors for most model still outperformed the AO model's prediction errors by 1% to 2% for most DVH metrics. These findings are confirmed by the Dice similarity coefficients on the isodose volumes, which are presented in FIG. 26. The AB model outperformed the AO model by up to 20% in patients #1 and #2 in the low and medium dose regions, and by about 8% in patient #3. The full DVH curves for the three patients are also presented in FIG. 27.

TABLE 2

Mean absolute error and its standard deviation (mean ± SD) for relevant DVH metrics on the target and on several organs for the three patients used for additional testing (average prediction for all 5 folds), for the AO and AB models. The values are expressed as percentage of the prescription dose ($D_{pre}$ = 60 Gy) for the metrics reporting the dose received by x % of volume ($D_x$), and as absolute difference for the metrics reporting the volume (in %) receiving a dose of y Gy ($V_y$).

|  |  | Mean absolute error for DVH metrics | | | | | |
| --- | --- | --- | --- | --- | --- | --- | --- |
|  |  | P1 - 3 coplanar (mean ± SD) | | P2 - 11 coplanar (mean ± SD) | | P3 - 10 non-coplanar (mean ± SD) | |
|  |  | AO model | AB model | AO model | AB model | AO model | AB model |
| PTV | $D_{99}$ (% of $D_{pre}$) | 4.00 ± 0.27 | 1.92 ± 0.94 | 6.15 ± 0.87 | 1.49 ± 1.00 | 0.92 ± 0.70 | 1.31 ± 0.58 |
|  | $D_{98}$ (% of $D_{pre}$) | 3.10 ± 0.44 | 1.27 ± 0.75 | 4.55 ± 0.81 | 1.24 ± 0.36 | 1.03 ± 0.76 | 0.90 ± 0.50 |
|  | $D_{95}$ (% of $D_{pre}$) | 1.95 ± 0.54 | 0.56 ± 0.56 | 4.05 ± 0.37 | 1.28 ± 0.77 | 1.07 ± 0.56 | 0.55 ± 0.40 |
|  | $D_5$ (% of $D_{pre}$) | 1.42 ± 0.45 | 1.94 ± 0.47 | 2.01 ± 0.47 | 0.72 ± 0.32 | 1.07 ± 0.53 | 0.18 ± 0.16 |
| Esophagus | $D_2$ (% of $D_{pre}$) | 0.73 ± 0.24 | 0.79 ± 0.46 | 2.54 ± 1.26 | 1.80 ± 1.62 | — | — |
|  | $V_{40}$ (% of volume) | 1.79 ± 1.44 | 2.50 ± 0.51 | 0.00 ± 0.00 | 0.00 ± 0.00 | — | — |
|  | $V_{50}$ (% of volume) | 1.67 ± 1.25 | 2.08 ± 0.93 | 0.00 ± 0.00 | 0.00 ± 0.00 | — | — |
| Heart | $V_{35}$ (% of volume) | 26.81 ± 1.39 | 7.37 ± 6.98 | 0.12 ± 0.00 | 0.03 ± 0.04 | 2.40 ± 1.70 | 0.76 ± 0.46 |
| Spinal cord | $D_2$ (% of $D_{pre}$) | 2.72 ± 1.36 | 3.64 ± 2.60 | 15.81 ± 2.33 | 3.60 ± 3.36 | 2.73 ± 2.41 | 3.13 ± 2.90 |
| Lungs | $D_{mean}$ (% of $D_{pre}$) | 3.05 ± 1.69 | 1.05 ± 0.51 | 1.83 ± 0.16 | 0.65 ± 0.65 | 2.26 ± 2.27 | 0.43 ± 0.35 |
|  | $V_5$ (% of volume) | 8.57 ± 2.52 | 2.42 ± 0.71 | 13.26 ± 3.60 | 2.63 ± 2.90 | 4.92 ± 2.55 | 1.28 ± 0.27 |
|  | $V_{20}$ (% of volume) | 5.97 ± 2.50 | 0.85 ± 0.86 | 0.65 ± 0.74 | 0.49 ± 0.48 | 4.69 ± 6.09 | 2.24 ± 0.59 | metrics and outperformed the AO model by more than 10% in some cases. For instance, the error on the heart $V_{35}$ in patient #1 (treated with 3 coplanar beams) was 27% for the AO model but only 7% for the AB model. Similarly, the prediction error for the spinal cord $D_2$ in patient #2 (treated with 11 coplanar beams) was 16% for the AO model but only 4% for the AB model; and the error for the lungs $V_5$ in the same patient was 13% for the AO model and 3% for the AB model. The differences were less pronounced in the case of patient #3 (treated with 10 non-coplanar beams), but the AB III.4: Discussion The AB model outperformed the AO model in all the evaluation criteria e.g., DVH metrics and Dice similarity coefficients for the isodose volumes. The difference in the prediction error between the two models was rather small in the high dose region (around 1% of the prescription dose, on average), but major differences were found for the medium to low dose regions (up to the 60-70% isodose volumes), where the beam information actually plays an important role. For these regions, the AB model presented a Dice coefficient 10% better than the AO model. Another example of the AB model's superior prediction accuracy for the low dose region is the lung volume receiving at least 5 Gy (V5), for which the prediction error was up to 5% lower than the AO model. Visual inspection of the predicted dose distributions from the two models also confirmed these results. The predictions from the AO model were unable to capture the dose features along the beam path, leading to a very uniform and isotropic dose fall-off. In contrast, the AB model accurately predicted the dose fingers corresponding to the different beam geometries.

To compare the generalization ability of the AO and AB models, the system also tested them in three additional patients from the clinic, with totally new beam configurations that were not included during training The results showed that the AB model achieved a prediction error more than 10% lower than the AO model in some cases. These findings confirm the superiority of the AB model to the AO model, even for cases where the beam configuration differs from the ones included during training.

The AB model was able to learn from a database that was heterogeneous in terms of beam configuration, by incorporating both anatomical and beam geometry information into the network. The results suggest that by representing the beam configuration in the dose domain, the system provides the model with valuable information about the dosimetric features that are not consistent through the database because of the variable beam arrangement. Thus, the model uses this elementary dosimetric information (FCBB) provided in the input channel and learns how to modulate it to achieve the optimal dose distribution for the given anatomy. The FCBB dose calculation used in this work is an improved ray-tracing type of algorithm, but it is believed that any other elementary dose calculation algorithm can be used for the same purpose. Thus, the AB model represents an important step forward towards an easier and more robust implementation of automatic planning techniques, since it reduces the model's dependence on consistent beam configuration characteristics through the training patient database. This is especially true for lung IMRT treatments, where tumors occur in different positions in the thorax, and their spatial relationships with other critical organs greatly vary from patient to patient, causing more variability in beam setup than in other tumor sites, such as prostate, where the beam configuration is relatively stable. Many other types of treatment could also benefit from this improved robustness against variable beam configuration, such as IMRT—4π treatments for brain or liver, among others.

Regarding previous studies from other groups, the results obtained from the AB model (average error for the mean dose equal to 1.39±1.27%) are consistent with the values reported by McIntosh and Purdie, who achieved a mean average difference of 1.33% for their lung test set using a homogeneous beam configuration (all patients treated with VMAT). They did not report the prediction error for the maximum dose, which is often more challenging to predict than the mean dose, but the system's model achieved excellent accuracy for this metric too, since the average for all organs was 2.85±3.06% for the test set. In addition, the prediction of the low dose region may be better thanks to the supplementary beam setup information, even for models that used the same beam configuration for all patients in the database. For instance, Moore et al., using a database where all patients (prostate and brain) were treated with VMAT, reported up to 20 Gy of difference between the predicted and real doses for regions that were far from the PTV.

In radiation therapy treatment planning, the sum of the square difference between the planned and the prescription dose is often used as the loss function. Accordingly, the system uses the MSE between the predicted and the clinically delivered doses as the loss function in the study. In addition, using MSE is computationally cheap and leads to a convex optimization problem with a stable gradient, which is easier to solve than non-convex problems. However, investigating the use of other metrics as loss functions, such as the inclusion of DVH metrics for target and organs, may be an interesting field of study.

The time needed to predict the three-dimensional dose distribution per patient was similar for the two models: AB model (11.66±0.14 s) and AO model (11.42±0.12 s). The time employed to compute the FCBB dose used as input to the model can be considered negligible since it was less than one second. In addition, the FCBB dose per beam can later be used to feed the optimizer in the treatment planning system employed to generate the plan. The predicted 3D dose matrix can then be used as a voxel-wise objective to create a treatment plan that mimics it. Since the most advanced optimizers can provide a solution within seconds, the total time required to generate a full plan may be kept under a minute, if the right hardware is used. This provides a good environment to implement online adaptive strategies, where the plan needs to be adapted while the patient is on the treatment couch, and every extra minute is of crucial importance. In addition, the presented model could be used as part of beam angle optimization strategies for IMRT, by generating 3D doses for different beam configurations and then selecting the optimal one according to DVH metrics or any other relevant criteria used in the clinic for plan evaluation. In this context, the generated doses could also serve as planning guidance for the dosimetrist or even as a decision support tool for the treating physician before going to treatment planning Eventually, the dose prediction model could be used in tumor board meetings for comparison with other suitable treatments and could assist in evaluating tumor control probability and possible secondary effects. However, as is the case with every deep learning application, one must be aware of the importance of the quality of the database used for training. If the ground truth doses are suboptimal, the predicted doses will be suboptimal too, i.e., the garbage in, garbage out paradigm. Therefore, the medical community should encourage the construction of high quality databases created by experienced planners, which can serve to improve and standardize future clinical practice. Meanwhile, the best solution might be the use of human-assisted and dynamic workflows, where the models are trained with the existing databases (heterogeneous plan quality) and used under the supervision of physicians. The physicians will then select the highest quality results, which will be used later to update and improve the current models.

Lastly, the dose prediction models in the existing literature have been applied so far to radiation therapy treatments with photons, i.e., IMRT or VMAT. However, extending these models to proton therapy represents an extra challenge, given the sensitivity of the dose distribution to heterogeneities in the tissue traversed. In this context, providing the model with basic beam setup information along the beam path is essential. The present system's model could be easily applied for that purpose.

III.5: Conclusion

The system uses deep neural networks to build a model that can learn from a database of previous patients treated with variable beam configuration and predict the three-dimensional dose distribution for a new patient. Two models were trained and compared: the first model (AO) only accounted for the anatomy of the patient, while the second model (AB) included both anatomical and beam setup information, the latter being represented in the dose domain The AB model showed greater accuracy and robustness against variable beam geometry than the AO model. This suggests that using a three-dimensional matrix containing elementary dose features along the beam paths as input to the model will help to achieve a more comprehensive automatic planning based on deep neural networks without the need to train specific models for every beam arrangement.

Section IV: Individualized 3D Dose Distribution Prediction Using Desired Dose Volume Histograms and Deep Learning In cancer radiotherapy, inverse treatment planning is a multi-objective optimization problem. There exists a set of plans with various trade-offs on Pareto surface which are referred as Pareto optimal plans. Currently exploring such trade-offs, i.e., physician preference is a trial and error process and often time-consuming. Therefore, it is desirable to predict desired Pareto optimal plans in an efficient way before treatment planning The predicted plans can be used as references for dosimetrists to rapidly achieve a clinically acceptable plan. Clinically the dose volume histogram (DVH) is a useful tool that can visually indicate the specific dose received by each certain volume percentage which is supposed to describe different trade-offs. Consequently, in some embodiments, one or more techniques disclosed herein are directed to a deep learning method based on patient's anatomy and DVH information to predict the individualized 3D dose distribution. Qualitative measurements have showed analogous dose distributions and DVH curves compared to the true dose distribution. Quantitative measurements have demonstrated that the presently disclosed model can precisely predict the dose distribution with various trade-offs for different patients, with the largest mean and max dose differences between true dose and predicted dose for all critical structures no more than 1.7% of the prescription dose.

IV.1: Introduction

With the rapid development of external beam therapy consisting of 3D conformal radiation therapy (3D-CRT), intensity modulated radiation therapy (IMRT), volume modulated arc therapy (VMAT), and so on, the treatment planning quality has been significantly improved while radiation therapy becomes one of the three most common approaches to clinical tumor treatment. Compared with surgery and chemotherapy, the radiation cannot only irradiate the tumor without affecting surrounding organs and tis-sues which leads to a conflicting goal in radiation therapy: irradiate planning target volumes (PTV) effectively while deliver the dose to organs at risk (OARs) as little as possible. Therefore, inverse IMRT treatment planning is a multi-objective optimization problem and mathematically can be expressed as the multi-objective weighted least squares function. Various organ weight combinations denoted by trade-offs would lead to a set of plans for a certain patient subject to Pareto surface which are referred as Pareto optimal plans. Currently exploring such trade-offs is a trial and error process and often time-consuming, so it is desirable to predict desired Pareto optimal plans in an efficient way before treatment planning The predicted plans can be used as references for dosimetrists to rapidly achieve a clinically acceptable plan. Although some approaches have been proposed to work on Pareto optimal plan prediction to guide clinical treatment planning, there are still some deficiencies. The weighted sum methods calculate the distance between inner and outer approximations of the Pareto surface to minimize the non-negative weighted sum of the objectives, however, they can only work on convex formulations. The epsilon constraint approaches [8-10] firstly apply a single minimization with some constraints to determine a point within a certain region of Pareto surface, and then duplicate the first step using different constraints to seek out a set of points on the Pareto surface. These constraint methods can handle non-convex objective function problem but call for much more time and effort.

In the past few years, deep learning technique has made a great progress and become a research hotspot benefiting from the advancement of graphics cards and theoretical algorithms Shiraishi et al. utilize previous treatment plans to train an artificial neural network (ANN) to predict a dose matrix, but this method requires many patient-specific geometric and planning parameters which limit the application of ANN. As a vital branch of deep learning, many novel convolutional neural networks (CNN) have achieved a dramatic performance in the field of computer vision and pattern recognition (CVPR). As the CVPR 2015 best paper, the fully convolutional network (FCN) adopts the convolutional layers to replace the last several fully-connected layers of traditional CNN for semantic segmentation, and firstly connect deep layers and shallow layers to preserve both global and local features. Furthermore, a stack of deconvolution operations is utilized in the FCN to keep the output the same size as the input. These innovative ideas make FCN exceed the state-of-the-art in many imaging tasks and many other modified networks are subsequently based on it. In particular, a model known as U-net is proposed for biomedical image segmentation. The U-net consist of two parts: the first part similar to the contracting path of the FCN is designed to extract global features while the second part aims to make a pixel-wise prediction by combining deconvolution output and high-resolution information from the first part; these two parts are more or less symmetric and the outputs at each level are concatenated in order to maintain global and local information simultaneously. In terms of above analysis, the U-net is desired to deal with the challenge of dose distribution prediction. Dan et al. firstly explores the feasibility of dose distribution prediction from contours utilizing a modified U-net model. Due to the powerful ability of learning features, they tend to make the model automatically abstract critical features from patient's anatomy without any handcrafted parameters to precisely predict the dose distribution and obtained a remarkable achievement. However, their model just can generate an average conformal dose distribution and cannot account for the physician preference, i.e., different trade-offs. In radiation therapy, the dose volume histogram (DVH) is a useful tool that can visually indicate the specific dose received by each certain volume percentage, the OARs and PTV are denoted by every curve which is supposed to describe different trade-offs for clinical requirements. Therefore, inspired by Dan's groundbreaking work, we'd like to construct a 3D model to focus on the different trade-offs based on patient's anatomy and DVH information. Qualitative and quantitative results demonstrate that the model is promising in individualized dose distribution prediction.

IV.2: Methods and Materials

Figure 28:
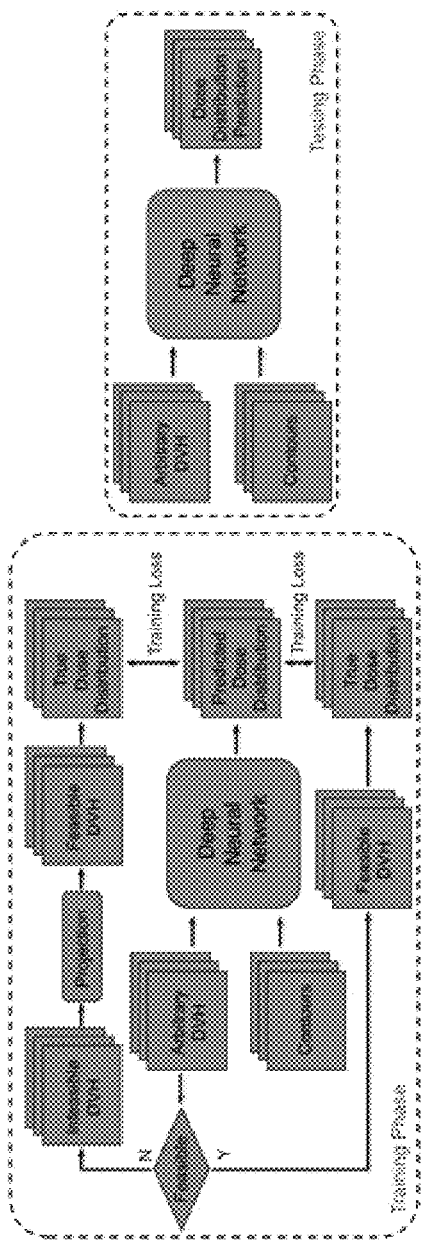
FIG. 28 is a block diagram illustrating an exemplary workflow for predicting individualized dose prediction, according to example embodiments.
Figure 29:
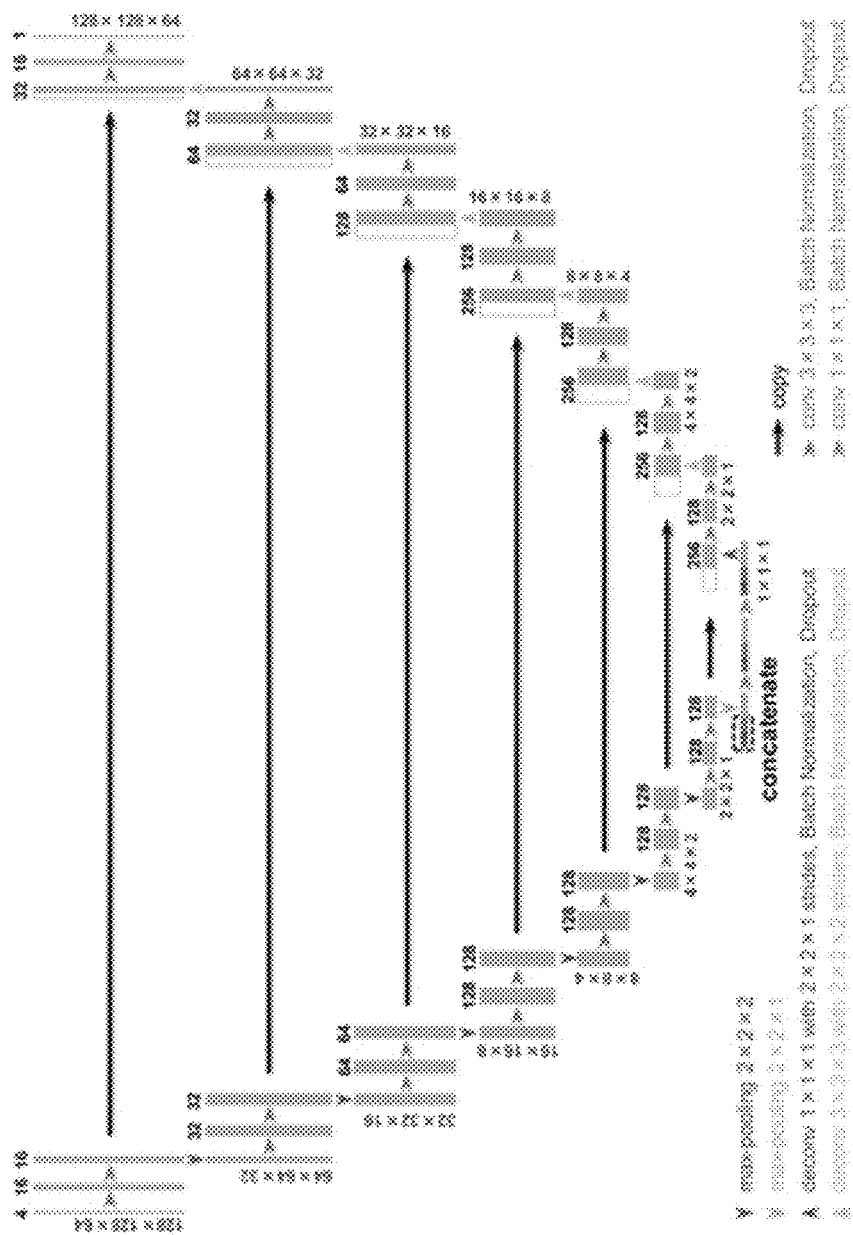
FIG. 29 is a block diagram illustrating a modified three-dimensional U-net architecture, according to example embodiments.

As shown in FIG. 28, the framework of the method consists of two stages: training phase and testing phase. For training dataset (data details seen in Section 2.2), each patient possesses multiple Pareto optimal dose distributions and corresponding DVHs which are called feasible DVHs, the DVHs from other patients are considered as infeasible DVHs. In training phase, the model takes arbitrary (infeasible or feasible) DVHs which are randomly chosen among all training patients and contours as inputs to predict dose distribution. When DVH is feasible, the corresponding dose distribution will be selected as ground truth for supervised learning. If DVH is infeasible, it will be firstly projected to a feasible DVH using a projection method, then the dose distribution corresponding to the feasible DVH is supposed to be true dose distribution as label. The projection method is a l1 norm which is used to measure the distance between infeasible and feasible DVHs to find most similar true dose distribution. In testing phase, any DVHs and contours will be fed into model for dose distribution prediction. The contour image including rectum, bladder, body, and PTV is divided into 4 separate contours which are considered as its own channel, respectively. In some embodiments, the system utilizes the vector to denote each DVH curve. As evident to those skilled in the art, the DVH possesses the properties of dose and corresponding cumulative volume, therefore the critical step is to employ which property of the DVH as the vector value. The system tests both two properties and found that the cumulative volume can represent DVH curve effectively. 4 contour images are encoded with convolution and max-pooling to obtain global feature maps and reduce the feature map size down to the size which can match DVH vector size properly. Meanwhile each DVH curve is converted into a vector whose value is cumulative volume and index represents dose, given that each element in vector indicates a specific dose volume point which can express clinical dose volume constraint, the system treats each vector element as a channel Then DVH vectors and feature maps from contours are concatenated along channel-axis. Finally, the feature fusion maps containing both contour information and DVH information is decoded with deconvolution and convolution to acquire dose distribution. The detailed architecture of encoding and decoding is shown in FIG. 29.

IV.2(a): Architecture p In this study, the modified 3D U-net architecture with encoding (left half) and decoding (right half) is illustrated in FIG. 29. As Simonyan et al. mentioned, stacking more convolutional layer with smaller kernel size can get fewer weight parameters and the same receptive field compared to bigger kernels, so a 3×3×3 convolutional kernel is applied except for the last two level convolutional layers which use 1×1×1 kernel instead due to the limitation of the feature map size. Zero padding is applied to keep feature size invariant in the convolution process. 6 max-pooling operations with 2×2×2 pooling size are employed to reduce the input size from 256×256×64 to 2×2×1, and then 1 max-pooling with 2×2×1 pooling size is utilized to obtain the feature maps with 1×1×1 size which is equal to the element size in DVH vector. The black dashed rectangle consisting of 4 different color blocks which denote 4 corresponding DVH vectors are concatenated with feature maps from contours along channel-axis. The channel numbers of feature maps from contours and DVHs are equivalent to make them possess same contribution to the final results. Batch normalization is a very efficient way to prevent the gradient from disappearing and accelerate convergence, thus the system may perform batch normalization after the rectified linear unit (ReLU) activated in all layers. Besides, dropout is applied at each convolutional layer to reduce overfitting with randomly deactivating nodes from the network with a certain probability.

IV.2(b): Data

Figure 30:
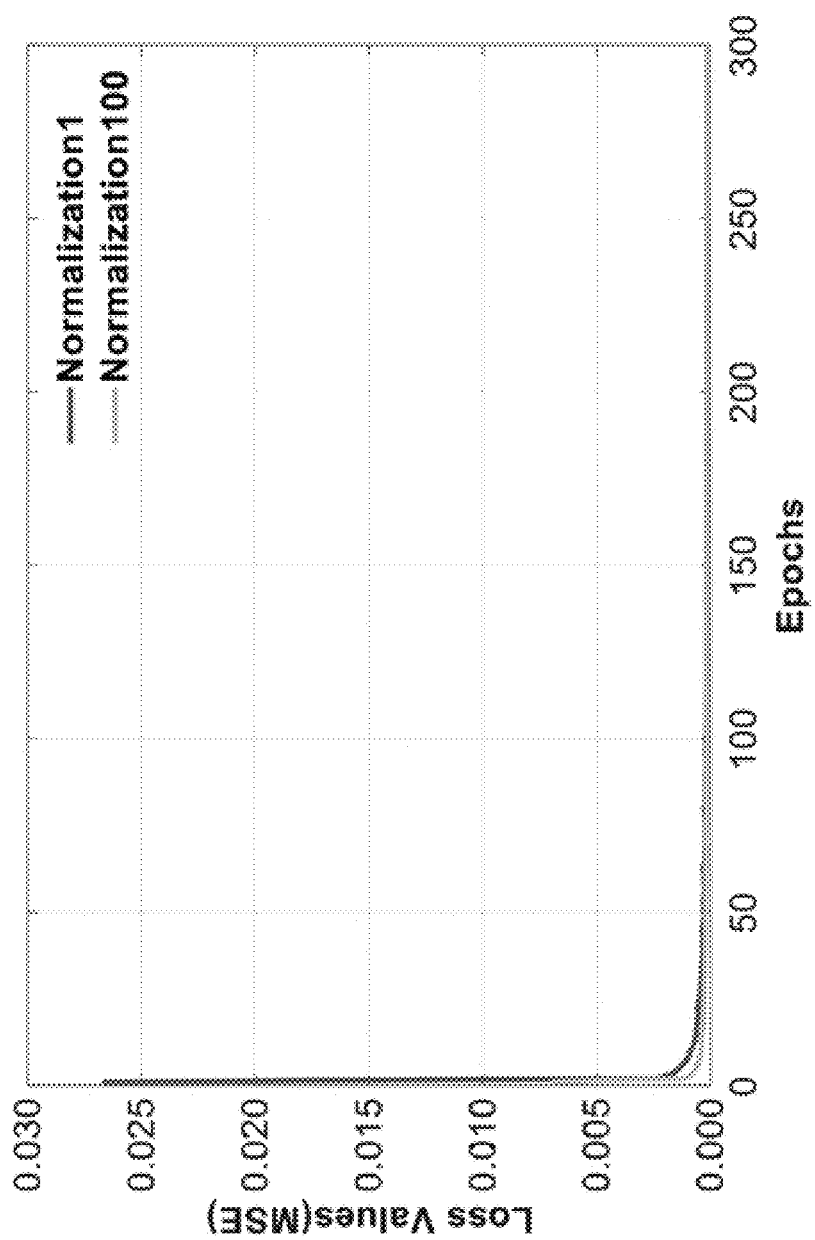
FIG. 30 is a chart illustrating loss values as a function of epochs in a training phase, according to example embodiments.

To validate the performance of the model, 97 clinical prostate patients are used here. 10 optimal treatment plans for each patient are generated via a shape-based dose calculation tool which can produce full dose for a given set of fluence maps or calculate a dose matrix for many modalities, thus the case amount is 970. Each patient with 4 critical structures comprising rectum, bladder, body, and PTV is subject to a standard 7 beam protocol. The training data contains 77 patients while 20 patients are chosen as testing data. The dimension of contour and dose distribution is 128×128×64, and each DVH vector contains 32 elements so that the total number of DVH elements is 128 which is also the channel number of contours at the bottom of the network. That is, the input channel of contours is 4 while DVH has 128 input channels. All dose distributions are normalized by PTV mean dose to generate a uniform dataset to benefit training robustness. As illustrated in FIG. 30, a method for dose normalization to speed up convergence is provided herein. Normalization 1 refers to that the mean dose delivered to PTV is normalized to 1 while Normalization 100 is the product of Normalization 1 and 100 such that the mean dose in PTV is equal to 100. In this way, the mean square error between true dose and predicted dose is artificially zoomed in. However, these two lines converge together after ~100 epochs which imply that this trick cannot lead to a final improved result.

IV.2(c): Training

As is known to all, the parameters of different networks for various purposes need to be determined manually and empirically. With trial-and-error and fine-tuning, the parameters for the architecture are set as follows.

$$\text{dropout} = rate_{initial} \times \left(\frac{layer_{current}}{layer_{max}}\right)$$

is the dropout function where the initial rate is set to 0.2 and the max layer is equal to 7. In this way, the dropout rate would increase with the layer becoming deeper where more weights could result in overfitting easily. In the system's architecture, the channel number is doubled with the level increasing to capture more global feature information and set the maximum of channels as 128 to speed up training. The mean square error (MSE) expressed as Equation (1) is employed as the loss function to describe the gap between the true dose and the predicted dose.

$$MSE = \frac{1}{N}\sum_{i=1}^{N}(D_{true}(i) - D_{pred}(i))^2$$

where i is the ith voxel in the 3D dose distribution with the total number of voxels N. Dtrue denotes true dose and Dpred represents predicted dose. The system adopts the Adam optimization algorithm to minimize the loss function while the initial learning rate is 1×10−3. Considering that big batch size can lead to out of memory error and make the network fall into the local minima, the system sets the batch size to 3 while it is generally 64 or 128 in the field of image classification and recognition. In this work, the system utilizes 6 NVIDIA Tesla K80 GPUs to implement the network in Keras library with TensorFlow backend. As shown in FIG. 30, the training loss value can be reduced down to ~1.1618×10−4 after 300 epochs at the cost of approximately 4 days, more epochs consume much time but achieve very little improvement meanwhile.

IV.3: Results

Figure 31:
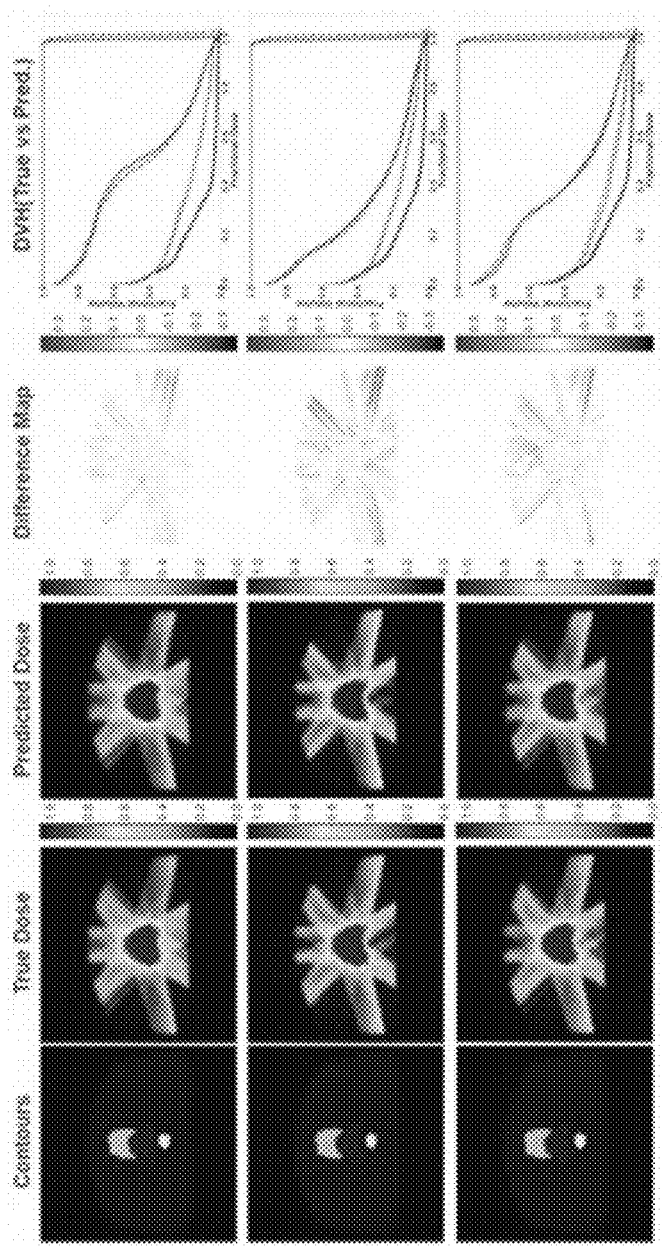
FIG. 31 is a block diagram illustrating individualized dose distribution prediction within one patient, according to example embodiments.
Figure 32:
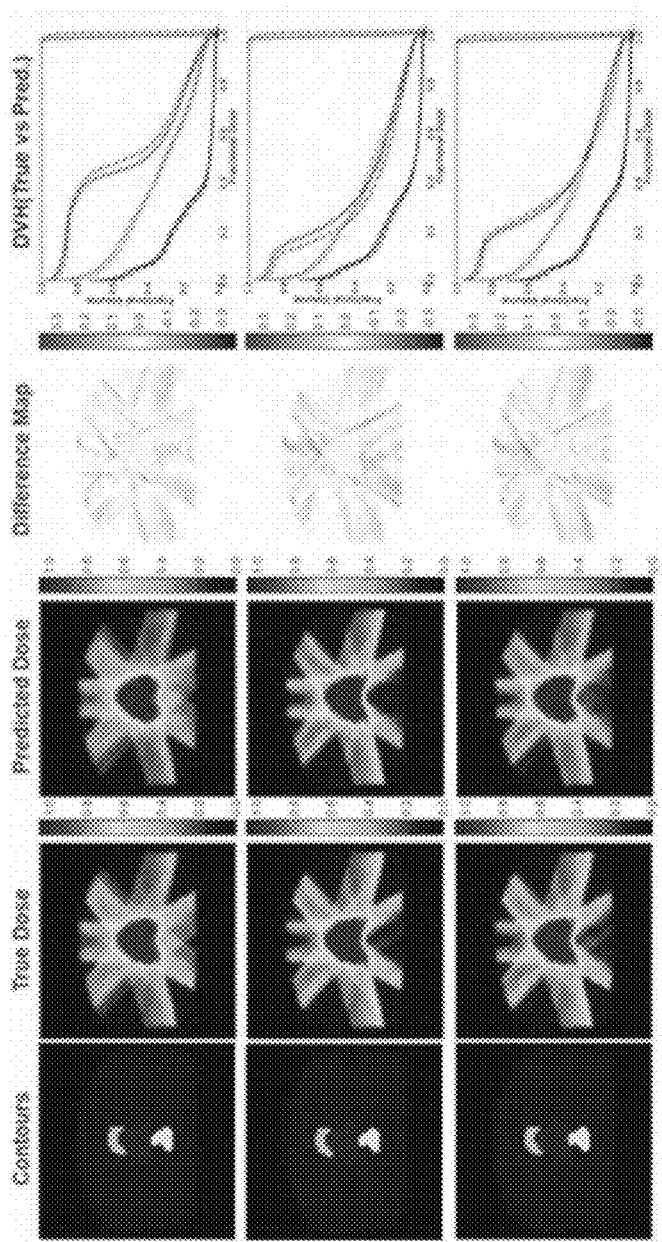
FIG. 32 is a block diagram illustrating individualized dose distribution prediction within one patient, according to example embodiments.

FIG. 31 shows the individualized dose distribution prediction for one patient where each row represents one plan within the same patient. As illustrated in the third column, the results predicted a similar dose distribution compared to the true dose, which demonstrated that the model has been capable of characterizing a conformal dose based on patient's anatomy including the shape, size, and location of critical structures. The difference maps between predicted dose and true dose for different plans showed an insignificant gap which meant the model can predict an accurate result. The DVH was generated from the true dose (solid line) and predicted dose distribution (dashed line) where different colors denote different OARs and PTV. Although different DVHs had different trade-offs, the predicted results can still generate a similar trend that covered the curves from true dose well. FIG. 32 is another example of predicted results for another patient. Similar to FIG. 31, the system's model can predict the desired results with maintaining the details of dose distribution far away from the PTV even for different trade-off plans.

To clinically evaluate the results, the prescription dose referring to the dose that 95% PTV volumes receive is introduced in the dose difference equation which can be expressed as follows:

$$dose_{difference} = \frac{dose_{true} - dose_{pred}}{dose_{prescription}} \times 100$$

where $dose_{true}$ denotes the dose of the true dose and $dose_{pred}$ is the predicted dose. The dose difference refers to mean or max dose difference corresponding to $dose_{true}$ and $dose_{pred}$ are denoted by mean dose value or max dose value.

Figure 33:
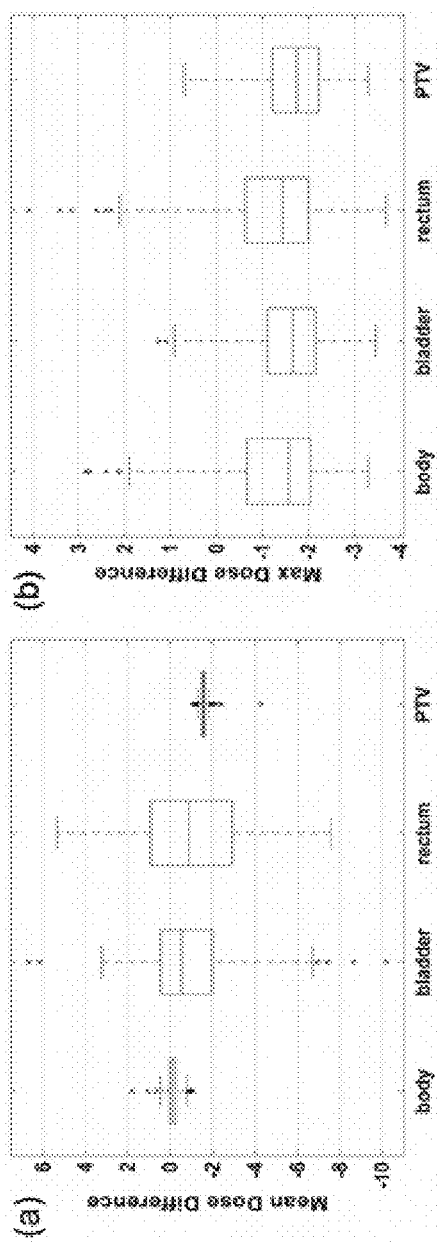
FIG. 33 is a chart illustrating a boxplot of mean dose difference (a) and mean dose difference (b) for testing patients, according to example embodiments.

As illustrated in FIG. 33, the boxplot of the mean and max dose differences calculated by the dose difference equation is plotted for each OAR and PTV across all testing patients including all plans for each patient. The median value denoted by the black line in the box were mildly negative which implied the model slightly over-predicted a dose for the OARs and PTV. To facilitate interpretation, the absolute dose difference statistics (mean value±standard deviation) were enumerated in Table 1. The max dose differences of body, bladder, rectum, and PTV were 1.22%, 1.59%, 1.13%, and 1.69% of the prescription dose, respectively. The mean dose errors for each critical structure were basically lower than the corresponding max dose errors, ranging from 0.12% for body to 1.58% for PTV. Overall, the absolute dose difference statistics between true dose and predicted dose for all 4 critical structures was no more than 1.7% of the prescription dose.

TABLE 1

Absolute dose difference statistics $\left(\left|\frac{dose_{true} - dose_{pred}}{dose_{prescription}}\right| \times 100\right)$ for OARS and PTV (mean value ± standard deviation).

|  | Mean dose difference | Max dose difference |
| --- | --- | --- |
| Body | 0.12 ± 0.32 | 1.22 ± 1.24 |
| Bladder | 0.83 ± 2.23 | 1.59 ± 0.90 |
| Rectum | 0.90 ± 2.81 | 1.13 ± 1.43 |
| PTV | 1.58 ± 0.25 | 1.69 ± 0.78 |

IV.4: Discussion

In this work, a modified 3D U-net architecture is constructed to predict the individualized dose distribution for different trade-offs. 3D network is suitable for learning essential features of patient's anatomy because the geometry of patient is supposed to be 3D, in contrast, 2D network need to avoid non-coplanar problem by selecting coplanar cases manually. The DVH containing different trade-offs is utilized to guide the network to predict diverse physician preferences for the same patient's anatomy and the contour can lead to a conformal dose, therefore the model integrating them as inputs can yield an individualized conformal dose distribution while the previous work just generates an average dose distribution which cannot handle the different trade-offs. The experimental results have demonstrated that the model can generate a desired result with maintaining the details of dose distribution for different patients as shown in FIG. 31 and FIG. 32. Dose difference statistics (FIG. 33 and Table 1) show that the model trends to predict an over dose. However, the error is minor where the largest max dose difference is ~1.69% of the prescription dose and the biggest error in the mean dose is ~1.58%. Although the system's model can yield a superior output, there are still some limitations to be solved further. Firstly, patient's anatomy, trade-off, and beam angle are three critical factors for the dose distribution. In this work, the beam angles of the dataset are fixed because the current model cannot account for diverse beam angles, which restricts its scope of application. This is another significant project needs to be solved. Secondly, the system used 10 plans within the same patient to train the model. In other words, the model just has learned a limited range of trade-offs which implies that the model may not predict a satisfied result when the trade-off exceeds the range using in the training phase. Naturally, a method of dealing with this shortcoming is to train the model using more number of treatment plans in order to cover an almost infinite range to yield any trade-off accurately. However, it would spend much more computational time which may be impractical. Furthermore, the clinical region of interest (ROI) actually calls for a limited set of candidates where 10 optimal plans with different trade-offs are enough for physicians.

IV.5: Conclusion

A deep learning method based on a modified 3D U-net with patient's anatomy and different trade-offs for treatment planning as inputs to predict an individualized dose distribution is provided above. Qualitative measurements have showed analogous dose washes and DVH curves compared to the true dose distribution. Quantitative measurements have demonstrated the model can precisely predict the dose distribution with various trade-offs for different patients, with the largest mean and max dose errors between true dose and predicted dose for the OARs and PTV no more than 1.7% of the prescription dose. In summary, the proposed method has great potential to possess the capability of capturing different trade-offs and patient's anatomy and can provide a guidance for the automatic individualized optimal treatment planning

Section V: Generating Pareto Optimal Dose Distribution for Radiation Therapy Treatment Planning Radiotherapy treatment planning currently requires many trial-and-error iterations between the planner and treatment planning system, as well as between the planner and physician for discussion/consultation. The physician's preferences for a particular patient cannot be easily quantified and precisely conveyed to the planner In some embodiments, one or more techniques disclosed herein present a real-time volumetric Pareto surface dose generation deep learning neural network that can be used after segmentation by the physician, adding a tangible and quantifiable endpoint to portray to the planner From 70 prostate patients, the system first generated 84,000 intensity modulated radiation therapy plans (1,200 plans per patient) sampling the Pareto surface, representing various tradeoffs between the planning target volume (PTV) and the organs-at-risk (OAR), including bladder, rectum, left femur, right femur, and body. The system divided the data to 10 test patients and 60 training/ validation patients. The system then trained a hierarchically densely connected convolutional U-net (HD U-net), to take the PTV and avoidance map representing OARs masks and weights, and predict the optimized plan. The HD U-net is capable of accurately predicting the 3D Pareto optimal dose distributions, with average [mean, max] dose errors of [3.4%, 7.7%](PTV), [1.6%, 5.6%](bladder), [3.7%, 4.2%] (rectum), [3.2%, 8.0%](left femur), [2.9%, 7.7%](right femur), and [0.04%, 5.4%](body) of the prescription dose. The PTV dose coverage prediction was also very similar, with errors of 1.3% (D98) and 2.0% (D99). Homogeneity was also similar, differing by 0.06 on average. The neural network can predict the dose within 1.7 seconds. Clinically, the optimization and dose calculation is much slower, taking 5-10 minutes.

V.1: Introduction

Radiation therapy is one of the major cancer therapy modalities, accounting for two-thirds of cancer patients in the US, either standalone or in conjunction with surgery, chemotherapy, immunotherapy, etc. In the typical current treatment planning work-flow, a treatment planner interacts with a commercial treatment planning system to solve an inverse optimization problem, either in an intensity modulated radiation therapy (IMRT) (Brahme, 1988; Convery and Rosenbloom, 1992; Bortfeld et al., 1994) or volumetric modulated arc therapy (VMAT) (Yu, 1995; Xing, 2003; Earl et al., 2003; Otto, 2008) setting. The planner manually tunes many hyperparameters, such as dose-volume constraints and weightings, to control the tradeoff between multiple clinical objectives. These hyperparameters are meticulously tuned in a time-consuming trial-and-error fashion to reach a suitable clinical solution. In addition, many rounds feedback from the physician is needed for the physician to discuss the plan quality with the planner and to properly portray their desired tradeoffs. This is largely due to the fact that the physician's preferences for a particular patient cannot be fully quantified and precisely conveyed to the planner This trial-and-error process results in hours of planning time, and the many iterations of physician feed-back may extend the time to several days until the plan is accepted.

Recently, deep learning with multi-layered neural networks has exploded in progress, particularly in computer vision. These new developments can be utilized to solve aspects of the treatment planning problem. Specifically, deep learning can be utilized to quickly realize the physician's preferences in a tangible and quantifiable manner that can be presented to the treatment planner prior to treatment planning In this study, a real-time Pareto surface dose generation deep learning neural network that can be used immediately after segmentation by the physician is provided herein. Pareto optimal plans are the solutions to a multicriteria problem with various tradeoffs. In particular, the tradeoff lies with the dose coverage of the tumor and the dose sparing of the various critical structures. The benefit of the of such a model is two-fold. First, the physician can interact with the model to immediately view a dose distribution, and then adjust some parameters to push the dose towards their desired tradeoff in real time. This also allows for the physician to quickly comprehend the kinds of the tradeoffs that are feasible for the patient. Second, the treatment planner, upon receiving the physician's desired dose distribution, can quickly generate a fully deliverable plan that matches this dose distribution, saving time in tuning the optimization hyperparameters and discussing with the physician. The system developed, trained, and tested the feasibility of the model on prostate cancer patients planned with 7 beam IMRT.

V.2: Methods

V.2(a): Prostate Patient Data and Pareto Plan Generation

The anatomical data for 70 prostate patients, in terms of the segmentation of the planning target volume (PTV) and the organs-at-risk, including bladder, rectum, left femur, right femur, and body. Ring and skin structures were added as tuning structures. The patient contours and dose arrays were formatted into 192×192×64 arrays at 2.5 mm$^3$ voxel size. The system then calculates the dose influence arrays for these 70 patients, for a 7 equidistant coplanar beam plan IMRT, with 2.5 mm$^2$ beamlets at 100 cm isocenter—a typical setup for prostate IMRT. Using this dose calculation data, the system generates IMRT plans that sampled the Pareto surface, representing various tradeoffs between the PTV and OARs. The multicriteria objective can be written as $$\underset{x}{\text{minmize}} \quad \{f_{PTV}(x), f_{OAR_1}(x), f_{OAR_2}(x), \ldots, f_{OAR_n}(x)\} \quad (1)$$
$$\text{subject to} \quad x \geq 0,$$

where x is the fluence map intensities to be optimized. There exists individual objectives, $f_s(x)$ $\forall s \in$ PTV, OAR, for the PTV and each of the OARs. Typically, the objective function is designed such that the goal is to deliver the prescribed dose to the PTV, while minimizing the dose to each OAR. Due to the physical aspects of external beam radiation, it is impossible to give the PTV exactly the prescription dose without irradiating normal tissue. Thus, the system arrives at a multicriteria objective, where there does not exist a single optimal x* that would minimize all $f_s(x)$ $\forall s \in$ PTV, OAR. For a proof of concept in this study, L2-norm represents the objective, $$f_s(x) = \frac{1}{2} \|A_s x - p_s\|_2^2.$$

Here, $A_s$ is the dose influence matrix for a given structure, and $p_s$ is the desired dose for a given structure, assigned as the prescription dose if s is the PTV, and 0 otherwise. This allows the system to linearly scalarize (Jahn, 1985) the multicritera optimization problem into a single-objective, convex optimization problem, $$\underset{x}{\text{minmize}} \quad \frac{1}{2} \sum_{s \in S} w_s^2 \|D_s x - p_s\|_2^2 \quad (2)$$
$$\text{subject to} \quad x \geq 0.$$

The key to scalarizing the problem is the addition of $w_s$, which are the tradeoff weights for each objective function, $f_s(x)$ $\forall s \in$ PTV, OAR. With different values of $w_s$, different Pareto optimal solutions are generated. Using an in-house GPU-based proximal-class first-order primal-dual algorithm, Chambolle-Pock (Chambolle and Pock, 2011), the system generates 1,200 pseudo-random plans per patient, totaling to 84,000 plans.

TABLE 1

Weight assignment categories. The function rand (lb, ub) represents a uniform random number between a lower bound, lb, and an upper bound, ub.

| Category | Description |
|---|---|
| Single organ spare | $w_{s_j}$ = rand(0, 1) |
| | $w_{OAR \backslash s_j}$ = rand(0, 0.1) |
| High weights | $w_s$ = rand(0, 1) ∀s ∈ OAR |
| Medium weights | $w_s$ = rand(0, 0.5) ∀s ∈ OAR |
| Low weights | $w_s$ = rand(0, 0.1) ∀s ∈ OAR |
| Extra low weights | $w_s$ = rand(0, 0.05) ∀s ∈ OAR |
| Controlled weight | $w_{bladder}$ = rand(0, 0.2) |
| | $w_{rectum}$ = rand(0, 0.2) |
| | $w_{lt\ fem\ head}$ = rand(0, 0.1) |
| | $w_{rt\ fem\ head}$ = rand(0, 0.1) |
| | $w_{shell}$ = rand(0, 0.1) |
| | $w_{skin}$ = rand(0, 0.3) |

The generation of each plan entailed assigning pseudo-random weights to the organs-at-risk. The weight for the PTV was kept at 1. The weight assignment fell into 1 of 6 categories as shown in Table 1. For each patient, 100 plans for each organ-at-risk used the single organ spare category (bladder, rectum, left femoral head, right femoral head, shell, skin), totaling to 600 single organ spare plans for each patient. To ensure a larger sampling of weights, another 100 plans of the high, medium, low, and extra low weights were generated, as well as 200 plans of the controlled weights category. The bounds for the controlled weights were chosen through trial and error such that the final plan generated had a high likelihood of being in acceptable clinical bounds for an inexperienced human operator, but not necessarily acceptable for an experienced physician. In total 1,200 plans were generated per patient. With 70 patients, the total number of plans generated was 84,000 plans.

V.2(b): Deep Learning Architecture

Figure 34:
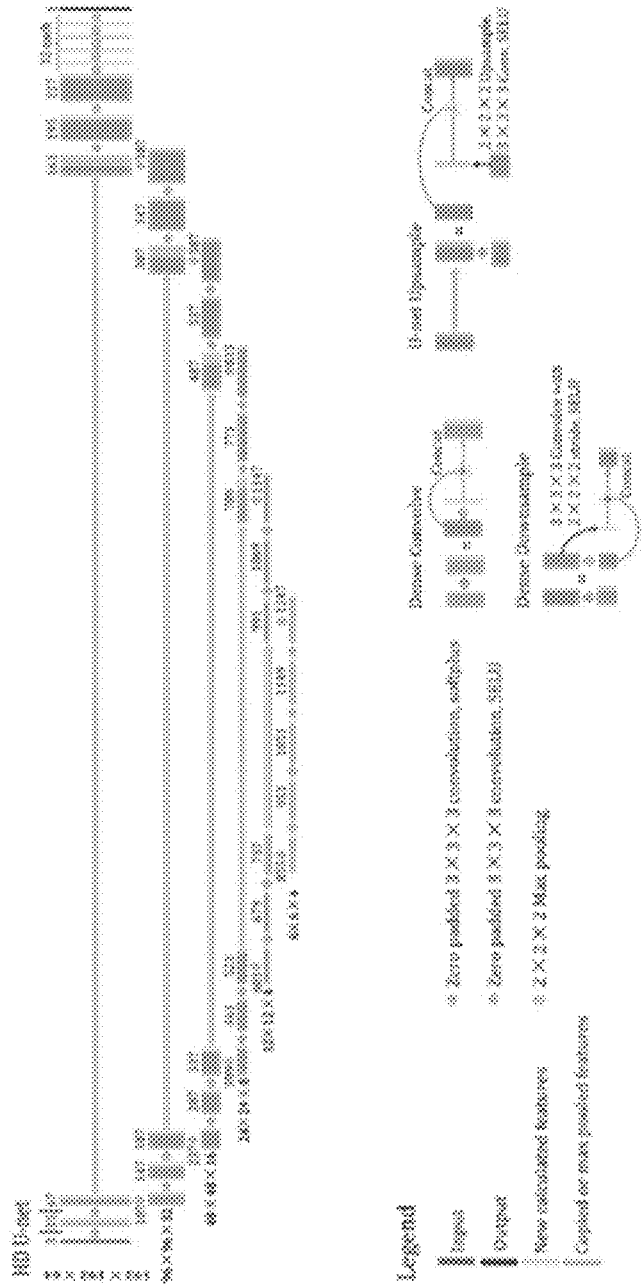
FIG. 34 is a block diagram illustrating HD U-net architecture, according to example embodiments.

A volumetric Hierarchically Dense U-net (HD U-net) architecture (Nguyen et al., 2019a), as shown in FIG. 34 is utilized, which adds in the densely connected convolutional layers (Huang et al., 2017) into the U-net architecture (Ronneberger et al., 2015). The HD U-net was trained to take as input the PTV contour, the body contour, and an avoidance map representing OARs masks assigned their respective $w_s$, and to predict the optimized 3D dose distribution.

In some embodiments, the HD U-net architecture has 5 max pooling and 5 upsampling operations, ultimately reducing the image size from 192×192×64 voxels to 6×6×4 voxels (the lowest level max pooling/upsampling layer reduces/expands leaves the slice dimension untouched), and back to 192×192×64 voxels. Skip connections are added between the first half and second half of the network, to allow for the propagation of local information with the global information. Densely connected convolutional connections are added in each block of the network, allowing for efficient information flow of features. The non-linearity used after each convolution was the scaled exponential linear unit (SELU) as presented by Klambauer et al. for self-normalizing neural networks (Klambauer et al., 2017). The study proved, using the Banach fixed-point theorem, that by having the SELU nonlinear activation, the neuron activations automatically converge towards zero mean and unit variance. Since the densely connection convolutional layers allows for less trainable parameters to be used, instead of doubling the number of kernels after every max pooling, the number of kernels was increased by 1.25 fold, to the nearest integer. The final activation layer as the softplus activation, as the output data is non-negative.

V.2(c): Training and Evaluation

Figure 35:
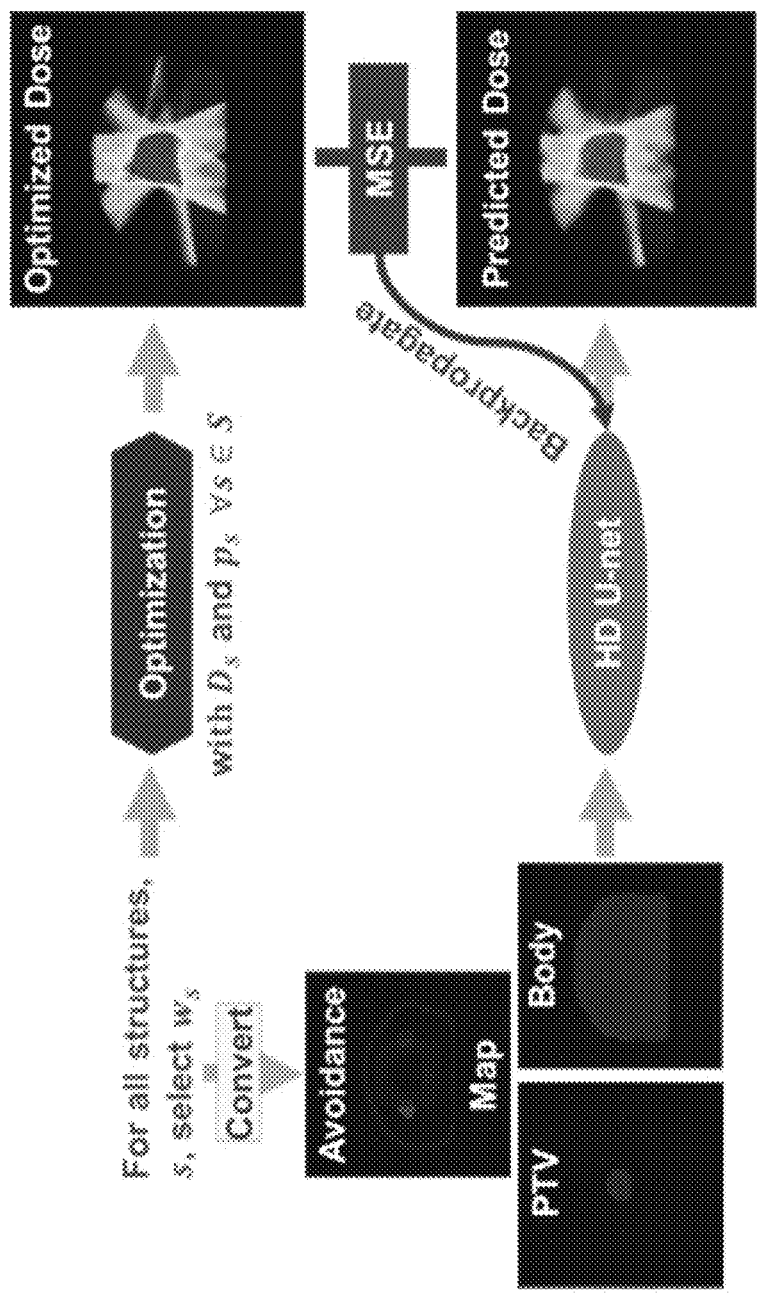
FIG. 35 is a block diagram illustrating a training schematic for HD U-net architecture for generating Pareto optimal doses, according to example embodiments.

The system randomly divided the data to 10 test patients and 60 model development (training and validation) patients. The 10 test patients were held out during the entire model development phase, and only used during evaluation. Five instances of the model were trained and validated, using 54 training patients and 6 validation patients, according the schematic outlined in FIG. 35.

At each training iteration, first a patient is selected and then set of $w_s$ is selected from one of the 1,200 plans. These set of weights are then converted into an avoidance map, which is a single channel of the input that represents the OAR masks assigned their corresponding $w_s$. In addition, the binary mask of the PTV and body are included as input. The HD U-net then makes a prediction using these inputs. The optimized dose, that was generated using the dose influence array and Chambolle-Pock algorithm, is used to minimize against the predicted dose distribution with a mean squared error loss. Alternatively, a plan can be generated on the fly from a given set of $w_s$, but is less efficient for training on a single GPU. During training the model was assessed on the validation data every 200 iterations of training. Each instance of the model used a different set of validation patients for determining the at which iteration the lowest validation score was obtained. Using all 1,200 plans per training patient—64,800 training plans total—the system trained the model for 100,000 iterations using the Adam optimizer, with a learning rate of $1 \times 10^{-4}$, using an NVIDIA V100 GPU. The 10 test patients were then evaluated using the trained models.

To equally compare across patients, the test plans were first normalized such that the dose to 95% of the PTV (D95) was equal to the prescription dose. For evaluation criteria, the PTV coverage (D98, D99), PTV max dose (defined as D2 by the ICRU-83 report (Grégoire and Mackie, 2011)), homogeneity $$\left(\frac{D2 - D98}{D50}\right),$$

and the structure max and mean doses ($D_{max}$ and $D_{mean}$) were evaluated.

V.3: Results

Figure 36:
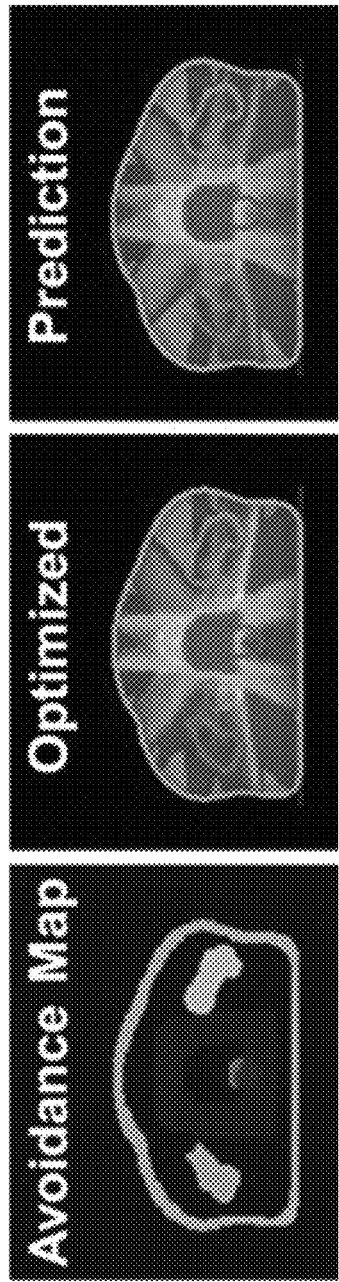
FIG. 36 is a block diagram illustrating an example avoidance map, optimal dose, and prediction for a test patient, according to example embodiments.
Figure 37:
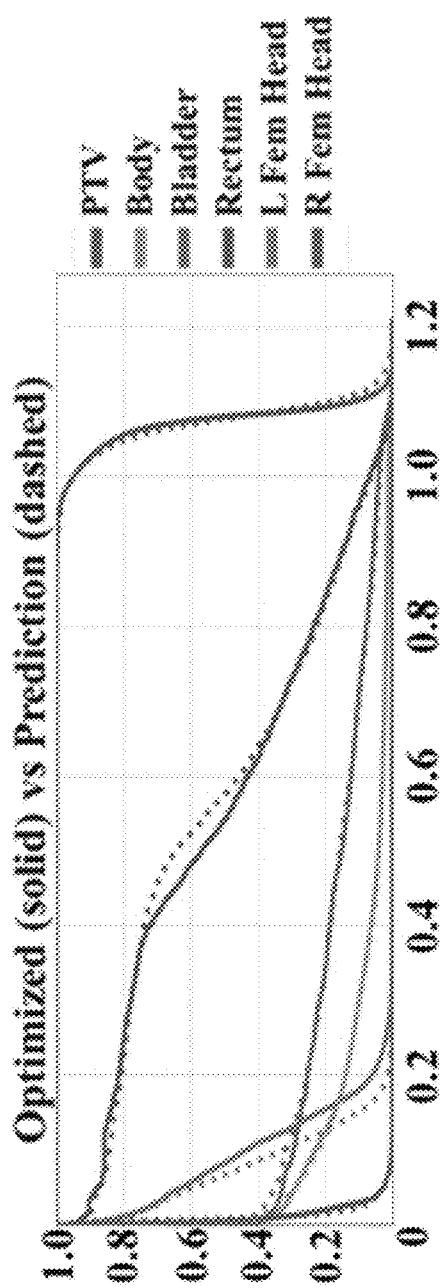
FIG. 37 is a block diagram illustrating a dose volume histogram for a test patient, according to example embodiments.

The HD U-net is capable of accurately predicting the Pareto optimal 3D dose distributions, with average mean dose errors of 3.4% (PTV), 1.6% (bladder), 3.7% (rectum), 3.2% (left femur), 2.9% (right femur), and 0.04% (body) of the prescription dose, as compared to the optimized plans. In addition, the HD U-net maintains the average max dose error of 7.7% (PTV), 5.6% (bladder), 4.2% (rectum), 8.0% (left femoral head), 7.7% (right femoral head), and 5.4% (body) of the prescription dose. The PTV dose coverage prediction was also very similar, with errors of 1.3% (D98) and 2.0% (D99) of the prescription dose. On average, the PTV homogeneity between the optimized reference dose and the prediction differed by 0.06. FIG. 36 shows the avoidance map, optimized dose and prediction, and FIG. 37 shows the dose volume histogram for a test patient.

Figure 38:
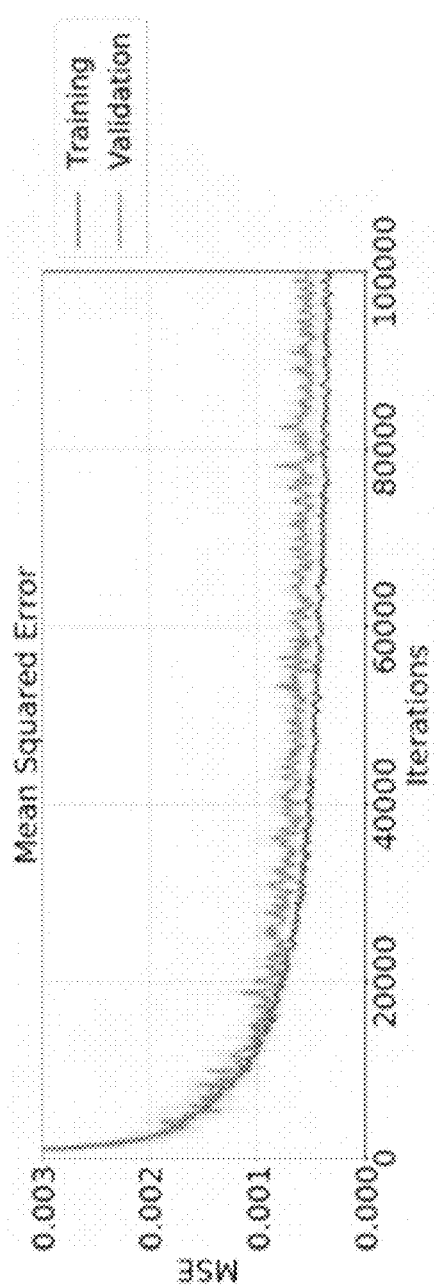
FIG. 38 is a chart illustrating training and validation loss, according to example embodiments.

It took approximately 15 days to train each instance of the model for 100,000 iterations. FIG. 38 represents the mean training and validation loss for the HD U-net over the 100,000 iterations of training. The validation curve begins to flatten out at around 80,000 iterations while the training loss continues to decrease. The small standard deviation in validation loss between the model instances indicate the stability and reproducibility of the overall model framework and choice of hyperparameters.

Given any structure weights set and anatomy, the neural network is capable of predicting the dose distribution in 1.7 seconds. Clinically, the optimization and dose calculation for IMRT takes approximately 5-10 minutes to complete. This makes it feasible for the model to be used in a real-time setting with a human operator.

V.4: Discussion and Conclusion

While other deep learning models designed to learn and predict the dose distribution of a patient plans, based either on historical clinical data or optimized plans to meet standardized clinical criteria, were developed in recent years (Nguyen et al., 2019a; Nguyen et al., 2019b; Chen et al., 2019; Fan et al., 2019; Shiraishi and Moore, 2016; Mahmood et al., 2018; Babier et al., 2018), this Pareto dose distribution model is the first deep learning model to able to generate any optimized plan from just the anatomy and structure weights. The model's real-time prediction capabilities allow for it to be used as a tool for the physician quickly generate a dose distribution with realistic tradeoffs between the PTV and various OARs. This can then be given to the planner as an endpoint, alongside the other typical planning information provided by the physician. The treatment planner now has a tangible, physician-preferred endpoint to meet, and the physician gets an initial understanding of what is physically achievable.

Section 6: Pareto Optimal Dose Distributions in Radiation Therapy

In some embodiments, one or more techniques described herein are directed to a novel domain specific loss, which is a differentiable loss function based on the dose volume histogram, into the training of deep neural networks for volumetric dose distribution prediction. In this study, the system will train a neural network for generating Pareto optimal dose distributions, and evaluate the effects of the domain specific loss on the model performance In this study, 3 loss functions—mean squared error (MSE) loss, dose volume histogram (DVH) loss, and adversarial (ADV) loss—were used to train and compare 4 instances of the neural network model: 1) MSE, 2) MSE+ADV, 3) MSE+DVH, and 4) MSE+DVH+ADV. The data for 70 prostate patients, including the planning target volume (PTV), and the organs-at-risk (OAR) were acquired as 96×96×24 dimension arrays at 5 mm$^3$ voxel size. The dose influence arrays were calculated for 70 prostate patients, using a 7 equidistant coplanar beam plan IMRT setup. Using a scalarized multicriteria optimization, 1200 Pareto surface plans per patient were generated by pseudo-randomizing the PTV and OAR tradeoff weights. With 70 patients, the total number of plans generated was 84,000 plans. The system divides the data into 54 training, 6 validation, and 10 testing patients. Each model was trained for a total of 100,000 iterations, with a batchsize of 2. All models used the Adam optimizer, with a learning rate of 1×10$^{-3}$.

Training for 100,000 iterations took 1.5 days (MSE), 3.5 days (MSE+ADV), 2.3 days (MSE+DVH), 3.8 days (MSE+DVH+ADV). After training, the prediction time of each model is 0.052 seconds. Quantitatively, the MSE+DVH+ADV model had the lowest prediction error of 0.038 (conformation), 0.026 (homogeneity), 0.298 (R50), 1.65% (D95), 2.14% (D98), 2.43% (D99). The MSE model had the worst prediction error of 0.134 (conformation), 0.041 (homogeneity), 0.520 (R50), 3.91% (D95), 4.33% (D98), 4.60% (D99). For both the mean dose PTV error and the max dose PTV, Body, Bladder and rectum error, the MSE+DVH+ADV outperformed all other models. Regardless of model, all predictions have an average mean and max dose error less than 2.8% and 4.2%, respectively.

The MSE+DVH+ADV model performed the best in these categories, illustrating the importance of both human and learned domain knowledge. Expert human domain specific knowledge can be the largest driver in the performance improvement, and adversarial learning can be used to further capture nuanced attributes in the data. The real-time prediction capabilities allow for a physician to quickly navigate the tradeoff space for a patient, and produce a dose distribution as a tangible endpoint for the dosimetrist to use for planning This is expected to considerably reduce the treatment planning time, allowing for clinicians to focus their efforts on the difficult and demanding cases.

VI.1: Introduction

External beam radiation therapy is one of the major treatments available to cancer patients, with major modalities available including intensity modulated radiation therapy (IMRT) (Brahme, 1988; Bortfeld et al., 1990; Bortfeld et al., 1994; Webb, 1989; Convery and Rosenbloom, 1992; Xia and Verhey, 1998; Keller-Reichenbecher et al., 1999) and volume modulated arc therapy (VMAT) (Yu, 1995; Otto, 2008; Palma et al., 2008; Shaffer et al., 2009; Shaffer et al., 2010; Xing, 2003; Earl et al., 2003; Daliang Cao and Muhammad, 2009). IMRT and VMAT have revolutionized the treatment planning over the past decades, drastically improving the treatment plan quality and patient outcome. However, many tedious and time consuming aspects still exist within the clinical treatment planning workflow. In particular, there are two aspects: 1) The dosimetrist must tediously and iteratively tune the treatment planning hyperparameters of the fluence map optimization in order to arrive at a planner-acceptable dose, and 2) many feedback loops between the physician and dosimetrist occur for the physician to provide his or her comments and judgement on the plan quality, until a physician-acceptable dose is finally produced. For a patient, this process can continually repeat for many hours to many days, depending on the complexity of the plan.

Much work over the years have been focused on reducing the treatment complexity by simplifying certain aspects in the planning workflow, such as feasibility seeking (Penfold et al., 2017), multicriteria optimization for tradeoff navigation on the Pareto surface (Craft et al., 2006; Craft et al., 2012; Monz et al., 2008), and other algorithms for performance improvements (Ngu yen et al., 2015; Nguyen et al., 2016b; Nguyen et al., 2016a; Nguyen et al., 2017; O'Connor et al., 2018; Long et al., 2018; Zarepisheh et al., 2014). While effective, these methods still require a large amount of intelligent input from the dosimetrist and physician, such as in weight tuning and deciding appropriate dose-volume constraints and tradeoffs. The field of knowledge-based planning (KBP) (Zhu et al., 2011; Appenzoller et al., 2012; Wu et al., 2014; Shiraishi et al., 2015; Moore et al., 2011; Shiraishi and Moore, 2016; Wu et al., 2009; Wu et al., 2011; Wu et al., 2013; Tran et al., 2017; Yuan et al., 2012; Lian et al., 2013; Folkerts et al., 2016; Good et al., 2013) addressed this by using machine learning techniques and models to predict clinically acceptable dosimetric criteria, using a large pool of historical patient plans and information to draw its knowledge from. Before the era of deep neural networks, KBP's efficacy was heavily reliant on not only the patient data size and diversity, but also on the careful selection of features extracted from the data to be used in the model (Wu et al., 2013; Tran et al., 2017; Wu et al., 2009; Wu et al., 2011; Yuan et al., 2012; Shiraishi and Moore, 2016; Lian et al., 2013; Folkerts et al., 2016; Folkerts et al., 2017). In addition, KBP prediction was limited to predict small dimensional data, such as the dose volume histogram (DVH) or specific dosimetrist criteria.

With the advancements in deep learning, particularly in computer vision (Krizhevsky et al., 2012; Girshick et al., 2014; Simonyan and Zisserman, 2014) and convolutional neural networks (LeCun et al., 1989), many studies have investigated clinical dose distribution prediction using deep learning on several sites such as for prostate IMRT (Nguyen et al., 2019c; Kearney et al., 2018), prostate VMAT (Shiraishi and Moore, 2016), lung IMRT (Barragán-Montero et al., 2019), head-and-neck IMRT (Fan et al., 2019; Babier et al., 2018b; Mahmood et al., 2018; Babier et al., 2018a), head-and-neck VMAT (Nguyen et al., 2019b). In addition to clinical dose prediction, deep learning models are capable of accurately generating Pareto optimal dose distributions, navigating the various tradeoffs between planning target volume (PTV) dose coverage and organs-at-risk (OAR) dose sparing (Nguyen et al., 2019a). Most of these methods utilize a simple loss function for training the neural network—the mean squared error (MSE) loss. MSE loss is a generalized, domain-agnostic loss function that can be applied to many problems in many domains. It's large flexibility also means that it is incapable of driving its performance in a domain-specific manner.

Mahmood and Babier et al. (Mahmood et al., 2018; Babier et al., 2018b; Babier et al., 2018a) investigated the use of adversarial learning for dose prediction. Since the development of generative adversarial networks (GAN) by Goodfellow (Goodfellow et al., 2014), adversarial loss has been popularized in the deep learning community for many applications. While used heavily for generative models, such as GANs, the adversarial loss can be applied to almost any neural network training. The adversarial loss's emerging success in deep learning application is largely due to the discriminator capability to calculate its own feature maps during the training process. In essence, the discriminator is learning its own domain knowledge of the problem. However, an adversarial framework is not without its issues. The user has little control over what kinds of features the discriminator may be learning during the training process. It is possible for the discriminator to learn the correct answer for the wrong reason. In addition, careful balancing the learning between the two networks is essential for preventing catastrophic failure. These may affect the overall performance of the prediction framework.

For the 2018 IEEE International Conference on Big Data, Muralidhar et al. (Muralidhar et al., 2018) proposed a domain adapted loss into their neural network training, in order to address deep learning in cases of limited and poor-quality data, which is a problem commonly found within the medical field. They found that, by including domain-explicit constraints, the domain adapted network model had drastically improved performance over its domain-agnostic counterpart, especially in the limited, poor-quality data situation. In some embodiments, domain specific losses are included into the radiation therapy problem of dose prediction. In some embodiments, differentiable loss function is added based on the dose volume histogram (DVH), one of the most important and commonly used metrics in radiation oncology, into the training of deep neural networks for volumetric dose distribution prediction. In some embodiments, the system is configured to train a neural network for generating Pareto optimal dose distributions, and evaluate the effects of MSE loss, DVH loss, and adversarial loss on the network's performance VI.2: Methods VI.2(a): Loss Functions In this study, 3 loss functions—mean squared error (MSE) loss, dose volume histogram (DVH) loss, and adversarial (ADV) loss—were used to train and compare 4 instances of the neural network model. The first model used only the voxel-wise MSE loss. The second model's loss function used the MSE loss in conjunction with the ADV loss. The third model used the MSE loss in conjunction with the DVH loss. The fourth and last model's loss function combined MSE, DVH, and ADV losses all together. Respectively, the study will denote each variation as MSE, MSE+ADV, MSE+DVH, and MSE+DVH+ADV. The following section will describe the ADV and DVH losses in detail.

VI.2(b): Adversarial Loss

The adversarial-style training utilizes a framework similar to that of generative adversarial networks (GAN) (Goodfellow et al., 2014), with respect to having another model acting as a discriminator to guide the main network to produce a dose distribution close to the real data. The major benefit to this approach is that the discriminator is calculating its own features and metrics to distinguish the ground truth data and predicted data. Effectively, this is allowing the discriminator to learn its own domain knowledge, and then provide feedback to update the main model. In some embodiments, the system utilizes the Least Squares GAN (LSGAN) (Mao et al., 2017) formulation:

$$\underset{\theta_{N_D}}{\text{minimize}}\ L_{ADV_D} = \frac{1}{2}\|N_D(y_{true}) - b\|_2^2 + \frac{1}{2}\|N_D(N_G(x)) - a\|_2^2 \quad (1)$$

$$\underset{\theta_{N_G}}{\text{minimize}}\ L_{ADV_G} = \frac{1}{2}\|N_D(N_G(x)) - c\|_2^2 \quad (2)$$

where $\theta_{N_D}$ and $\theta_{N_G}$ are the trainable weights parameterizing the discriminator, $N_D$, and generator, $N_G$, respectively. $L_{ADV_D}$ and $L_G$ are the loss functions to be minimized with respect to $N_D$ and $N_G$. As per suggestion by the LSGAN publication, to minimize the Pearson $X^2$ divergence, $a=-1$, $b=1$, and $c=0$.

VI.2(c): Dose Volume Histogram Loss

The DVH is one of the most commonly used metrics in radiation oncology for evaluating the quality of a plan, so it natural to assume that including this metric as part of the loss would be beneficial. However, the calculation of the DVH involves non-differentiable operations, which means any loss based on it cannot provide a gradient to update the neural network. The system defines a differential approximation of the DVH as $\widetilde{DVH}$. Given a binary segmentation mask, $M_s$, and a volumetric dose distribution, D, the volume at or above a given dose value, d, can be approximated as $$v_{s,d}(D, M_s) = \frac{\sum_{i,j,k} S\left(\frac{m}{b}(D(i,j,k) - d)\right) M_s(i,j,k)}{\sum_{i,j,k} M_s(i,j,k)} \quad (3)$$

where $$S(x) = \frac{1}{1 + e^{-x}}$$

is the sigmoid function, m controls the steepness of the curve, and b is the bin width of the histogram. Based on this, the $\widehat{DVH}_s$ for any structure, s, can then be defined as:

$$\widehat{DVH}_s(D,M) = (v_{s,d_0}, v_{s,d_1}, \ldots, v_{s,d_n}) \quad (4)$$

With the bin centers defined as $$\text{bin\_center} = \left(\frac{d_0 + d_1}{2}, \frac{d_1 + d_2}{2}, \ldots, \frac{d_n + d_{n+1}}{2}\right) \quad (5)$$

To illustrate Equation 1, the system calculated the DVH and the approximated DVH, of varying steepness values of m={1,2,4,8}, of a PTV and OAR or an example prostate patient. As demonstrated by FIG. 39, when the steepness of the curve m→∞, then $\widehat{DVH}$ →DVH.

Because $\widehat{DVH}$ is computed using sigmoid, the gradient, $$\frac{\partial \widehat{DVH}(D, M)}{\partial D} = \left(\frac{v_{s,d_0}}{\partial D}, \frac{v_{s,d_1}}{\partial D}, \ldots, \frac{v_{s,d_n}}{\partial D}\right),$$

can be computed, allowing for a loss function utilizing $\widehat{DVH}$ to be used to update the neural network weights. The system may then define a mean squared loss of the DVH as $$L_{DVH}(D_{true}, D_{pred}, M) = \quad (6)$$
$$\frac{1}{n_s} \sum_s \frac{1}{n_b} \|\widehat{DVH}_s(D_{true}, M_s) - \widehat{DVH}_s(D_{pred}, M_s)\|_2^2$$

While a gradient of Loss$_{DVH}$ exists, it is possible that the gradient space is ill-behaved and would be not suitable for use. For example, let D=(1,2). The exact DVH and approximate DVH with varying values of m={1,2,4,8} can be calculated, shown in FIG. 40.

Figure 39:
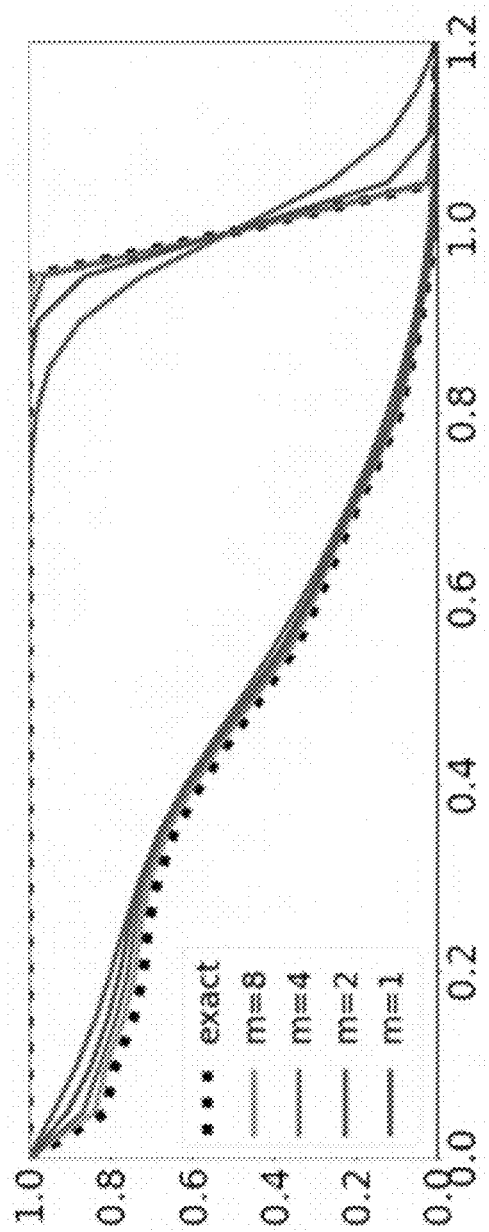
FIG. 39 is a chart illustrating dose volume histogram and dose volume histogram calculations, according to example embodiments.
Figure 40:
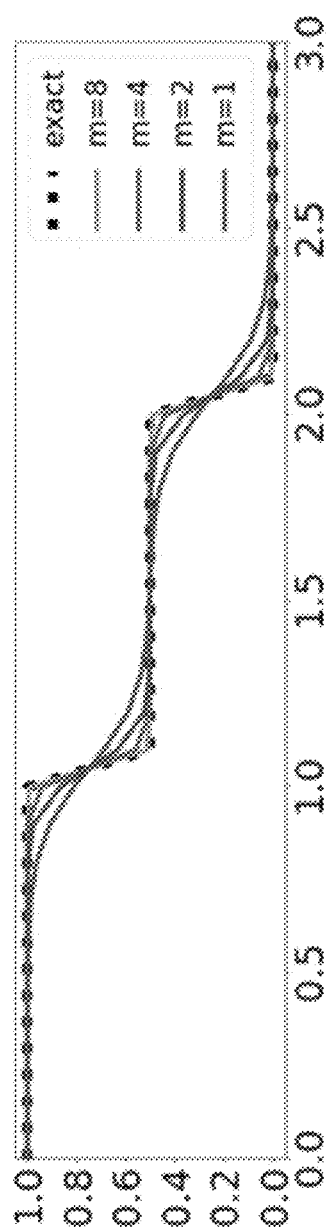
FIG. 40 is a chart illustrating dose volume histogram and dose volume histogram calculations, according to example embodiments.

It can be observed that in this toy example in FIG. 40 the approximation is smoother and has larger error with smaller m, which agrees with FIG. 39. To investigate the gradient properties of the loss using the approximate DVH, the system calculates $$\|DVH([1, 2], M) - \widehat{DVH}([i, j], M)\|_2^2 \forall i, j \in (0, 3)$$

for M=[1,1].

Figure 41:
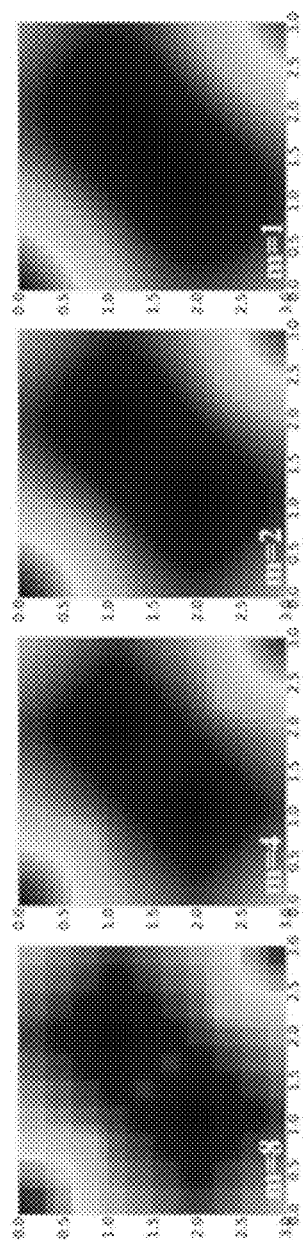
FIG. 41 is a block diagram illustrating an objective value map of a loss function, according to example embodiments.

FIG. 41 shows the squared error value of the difference between DVH for the data (1,2) and the $\widehat{DVH}$ for the data (i, j) ∀i, j ∈ (0,3). There are multiple local minima In this example, it is when (i, j)=(1,2) or (2,1), since either will produce the same DVH. For higher m, the local minimas become more defined, with steeper gradients surrounding them, an undesirable quality for optimization and learning problems. While a lower steepness, m, may not approximate the DVH as well, the loss function involving the $\widehat{DVH}$ maintains the same local minima, and provides a smoother, and more well-behaved gradient than its sharper counterparts. For the remainder of this study, let $\widehat{DVH}$ have m=1.

VI.2(d): Model Architecture

In this study the dose prediction model that was utilized was a U-net style architecture (Ronneberger et al., 2015), and the discriminator model was a classification style architecture (LeCun et al., 1998; LeCun et al., 1999).

Figure 42:
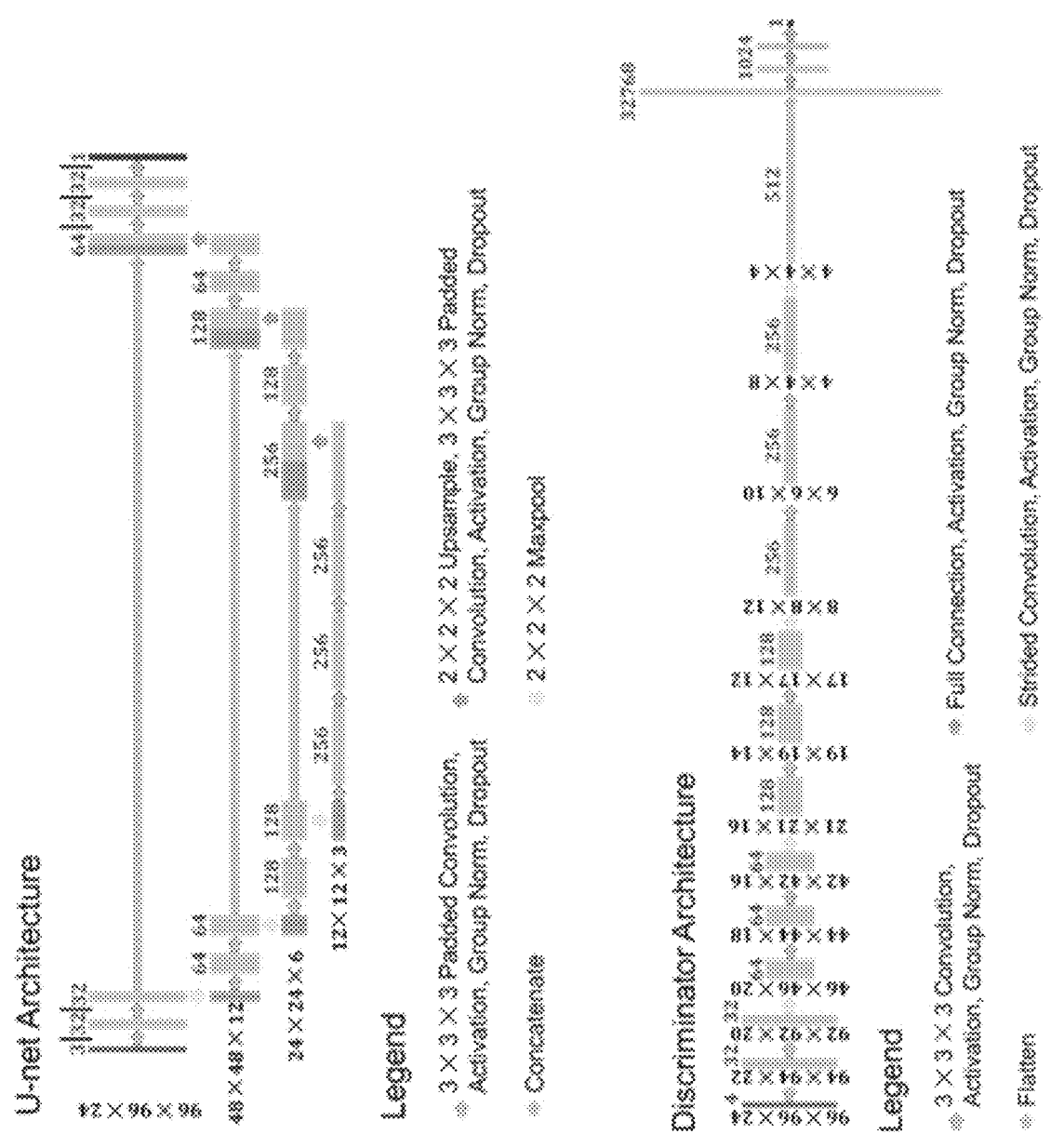
FIG. 42 is a block diagram illustrating deep learning model architectures, according to example embodiments.

Specifically, the models were adjusted to match the data shape. The architectures shown in FIG. 42 depict the models used in the study. The U-net takes as input a 3 channel tensor that consists of, 1) the PTV mask with the value $w_{PTV}$ assigned as its non-zero value, 2) the OAR masks that include all the OARs respectively assigned their $w_{OAR_s}$, and 3) the body mask as a binary. The U-net then performs multiple calculations, with maxpooling operations to reduce the resolution for more global feature calculation, and then upsampling operations to eventually restore the image resolution back to the original. Concatenation operations are used to merge the local features calculated in the first half of the U-net with the global features calculated at the bottom and later half of the U-net.

The discriminator architecture is of an image classification style network. The goal of the discriminator is to learn how to distinguish the optimized dose distributions versus the U-net predicted dose distribution. Similar to conditional generative adversarial network framework (Mirza and Osindero, 2014), the discriminator will additionally take the same input as the U-net. In total, the input data has 4 channels—3 channels of the U-net's input and 1 channel of either the optimized or predicted dose distribution. As shown in FIG. 42., the discriminator goes through a process of convolutions and strided convolutions to calculate new feature maps and to reduce the image resolution, respectively. It is important to note that the strided convolution is used to reduce one or more of the image dimensions by half, but differ in which dimensions are being reduced in order to eventually reduce the image to 4×4×4 pixels. For example, the first strided convolution is applied to the first 2 image dimensions, reducing the image from 92×92×20 to 46×46× 20, but the last strided convolution is reducing the 3$^{rd}$ image dimension. The specific details can be seen in the image sizes specified in FIG. 42.

In addition, Group Normalization (Wu and He, 2018) was used in place of Batch Normalization (Ioffe and Szegedy, 2015), which has been shown to allow for the models to effectively train on small batch sizes. All activations in the hidden layer are rectified linear units (ReLU) activations. Final activations for both the U-net and discriminator are linear activations.

VI.2(e): Patient and Pareto Optimal Plan Data

The data for 70 prostate patients, including the planning target volume (PTV), and the organs-at-risk (OAR)—body, bladder, rectum, left femoral head, and right femoral head— were acquired as 96×96×24 dimension arrays at 5 mm$^3$ voxel size. Ring and skin structures were added as tuning structures. The dose influence arrays were calculated for the 70 patients, using a 7 equidistant coplanar beam plan IMRT setup. The beamlet size was 2.5 mm$^2$ at 100 cm isocenter. Using this dose influence data, the system generated IMRT plans that sampled the Pareto surface, representing various tradeoffs between the PTV dose coverage and OAR dose sparing. The multicriteria objective can be written as $$\operatorname*{minimize}_{x} \{f_{PTV}(x), f_{OAR_1}(x), f_{OAR_2}(x), \ldots, f_{OAR_n}(x)\} \qquad (7)$$

subject to $x \geq 0$, where x is the fluence map intensities to be optimized. The individual objectives, $f_s(x)$ $\forall s \in$ PTV, OAR, are for the PTV and each of the OARs. In radiation therapy, the objective function is formulated with the intention to deliver the prescribed dose to the PTV, while minimizing the dose to each OAR. Because to the physical aspects of radiation in external beam radiation therapy, it is impossible to deliver to the PTV the prescription dose without irradiating normal tissue. In addition, it has been shown that the integral dose to the body is similar regardless of the plan (Nguyen et al., 2014; Reese et al., 2009; Aoyama et al., 2006; D'souza and Rosen, 2003), so, in essence, one can only choose how to best distribute the radiation in the normal tissue. For example, by reducing the dose to one OAR, either the PTV coverage will worsen or more dose will be delivered to another OAR. Therefore, the system arrives at a multicriteria objective, where there does not exist a single optimal x* that would minimize all $f_s(x)$ $\forall s \in$ PTV,OAR. In this study, the system uses the $l_2$-norm to represent the objective, $$f_s(x) = \frac{1}{2}\|A_s x - p_s\|_2^2.$$

In this formulation, $A_s$ is the dose influence matrix for a given structure, and $p_s$ is the desired dose for a given structure, assigned as the prescription dose if s is the PTV, and 0 otherwise. This allows for the system to linearly scalarize the multicriteria optimization problem (Jahn, 1985), by reformulating it into a single-objective, convex optimization problem $$\operatorname*{minimize}_{x} \frac{1}{2}\sum_{s \in S} w_s^2 \|A_s x - p_s\|_2^2 \qquad (8)$$

subject to $x \geq 0$.

Scalarizing the problem required the addition of new hyperparameters, $w_s$, which are the tradeoff weights for each objective function, $f_s(x)$ $\forall s \in$ PTV, OAR. By varying $w_s$ to different values, different Pareto optimal solutions can generated by solving the optimization problem. Using an in-house GPU-based proximal-class first-order primal-dual algorithm, Chambolle-Pock (Chambolle and Pock, 2011), the system generated many pseudo-random plans, by assigning pseudo-random weights to the organs-at-risk. The weight assignment fell into 1 of 6 categories as shown in Table 1.

TABLE 1

Weight assignment categories for the organs at risk. The function rand (lb, ub) represents a uniform random number between a lower bound, lb, and an upper bound, ub. In the high, medium, low, extra low, and controlled weights category, the PTV had a 0.05 probability of being assigned rand (0, 1) instead of 1.

| Category | Description |
| --- | --- |
| Single organ spare | $w_{s_j}$ = rand(0, 1) |
|  | $w_{OAR \setminus s_j}$ = rand(0, 0.1) |

TABLE 1-continued

Weight assignment categories for the organs at risk. The function rand (lb, ub) represents a uniform random number between a lower bound, lb, and an upper bound, ub. In the high, medium, low, extra low, and controlled weights category, the PTV had a 0.05 probability of being assigned rand (0, 1) instead of 1.

| Category | Description |
| --- | --- |
| High weights | $w_s$ = rand(0, 1) $\forall s \in$ OAR |
| Medium weights | $w_s$ = rand(0, 0.5) $\forall s \in$ OAR |
| Low weights | $w_s$ = rand(0, 0.1) $\forall s \in$ OAR |
| Extra low weights | $w_s$ = rand(0, 0.05) $\forall s \in$ OAR |
| Controlled weight | $w_{bladder}$ = rand(0, 0.2) |
|  | $w_{rectum}$ = rand(0, 0.2) |
|  | $w_{lt\,fem\,head}$ = rand(0, 0.1) |
|  | $w_{rt\,fem\,head}$ = rand(0, 0.1) |
|  | $w_{shell}$ = rand(0, 0.1) |
|  | $w_{skin}$ = rand(0, 0.3) |

For each patient, 100 plans of the single organ spare category (bladder, rectum, left femoral head, right femoral head, shell, skin) were generated for each critical structure, yielding 600 organ sparing plans per patient. To further sample the tradeoff space, another 100 plans of the high, medium, low, and extra low weights category were generated, as well as 200 plans of the controlled weights category. In the high, medium, low, extra low, and controlled weights category, the PTV had a 0.05 probability of being assigned rand (0,1) instead of 1. The bounds for the controlled weights were selected through trial-and-error such that the final plan generated was likely to fall within clinically relevant bounds, although it is not necessarily acceptable by a physician. In total 1200 plans were generated per patient. With 70 patients, the total number of plans generated was 84,000 plans.

VI.2(f): Training and Evaluation

The system first notates the mean squared error loss, dose volume histogram loss, and U-net's adversarial loss as $L_{MSE}(y_t, y_p)$, $L_{DVH}(y_t, y_p, M)$, and $L_{ADV_G}(y_t, y_p, x)$, where x is the input into the U-net model, $y_t$ is the ground truth optimized dose distribution, $y_p$ is the predicted dose distribution, and M contains the binary segmentation masks. The total objective for training the U-net is then defined as $$L_{Total} = L_{MSE}(y_t, y_p) + \lambda_{DVH} L_{DVH}(y_t, y_p, M) + \lambda_{ADV} L_{ADV_G}(y_p, x), \qquad (9)$$

and the objective for training the discriminator is simply $L_{ADV_D}(y, x)$, where y can either be $y_t$ or $y_p$ for a given training sample. For each study—MSE, MSE+ADV, MSE+DVH, and MSE+DVH+ADV—the weightings, $\lambda_{DVH}$ and $\lambda_{ADV}$, used are shown in Table 2. These were chosen by evaluating the order of magnitude of the values that each loss function exhibits for a converged model. From previous dose prediction studies and results (Nguyen et al., 2019c; Nguyen et al., 2019b), the system may estimate that the $L_{MSE} \sim 10^{-4}$ and $L_{DVH} \sim 10^{-3}$ for a converged model. Since the system may use least squares GAN framework, the system may estimate the loss $L_{ADV_G}$ ranges from $10^{-1}$ to $10^0$. The choice of $\lambda_{DVH}$ and $\lambda_{ADV}$, shown in Table 2, is to have each component of the loss to be within a similar order of magnitude for when the model is converged.

TABLE 2

Choices of $\lambda_{DVH}$ and $\lambda_{ADV}$ for the loss function shown in Equation 9.

| | $\lambda_{DVH}$ | $\lambda ADV$ |
|---|---|---|
| MSE | 0 | 0 |
| MSE + ADV | 0 | 0.001 |
| MSE + DVH | 0.1 | 0 |
| MSE + DVH + ADV | 0.1 | 0.001 |

The system divided the 70 prostate patients into 54 training, 6 validation, and 10 testing patients, yielding 64,800 training, 7,200 validation, and 12,000 testing plans. For the training that involved adversarial loss, the U-net and discriminator would alternate every 100 iterations, to allow for some stability in the training and loss. The discriminator was trained to take as input the same inputs as the u-net as well as a dose distribution, either from the real training data or from the U-net's prediction. With a 0.5 probability, the discriminator would receive either real training data or data predicted from the U-net. Each U-net model was trained for a total of 100,000 iterations, using a batchsize of 2. All models used the Adam optimizer, with a learning rate of $1\times10^{-3}$. All training was performed on an NVIDIA 1080 Ti GPU with 11 GB RAM. After training, the model with the lowest total validation loss was used to assess the test data.

All dose statistics will also be reported relative to the relative prescription dose (i.e. the errors are reported as a percent of the prescription dose). As clinical evaluation criteria PTV coverage (D98, D99), PTV max dose, homogeneity $$\left(\frac{D2 - D98}{D50}\right),$$

van't Riet conformation number (Van't Riet et al., 1997)

$$\left(\frac{(V_{PTV} \cap V_{100\%Iso})^2}{V_{PTV} \times V_{100\%Iso}}\right),$$

the dose spillage R50

$$\left(\frac{V_{50\%Iso}}{V_{PTV}}\right),$$

and the structure max and mean doses ($D_{max}$ and $D_{mean}$) were evaluated. $D_{max}$ is defined as the dose to mean, 2% of the structure volume, as recommended by the ICRU report no 83 (Grégoire and Mackie, 2011).

VI.3: Results

For each model, training for 100,000 iterations took 1.5 days (MSE), 3.5 days (MSE+ADV), 2.3 days (MSE+DVH), 3.8 days (MSE+DVH+ADV). After training, the prediction time of each U-net is the same at 0.052 seconds, since all 4 U-net models in the study are identical in architecture.

Figure 43:
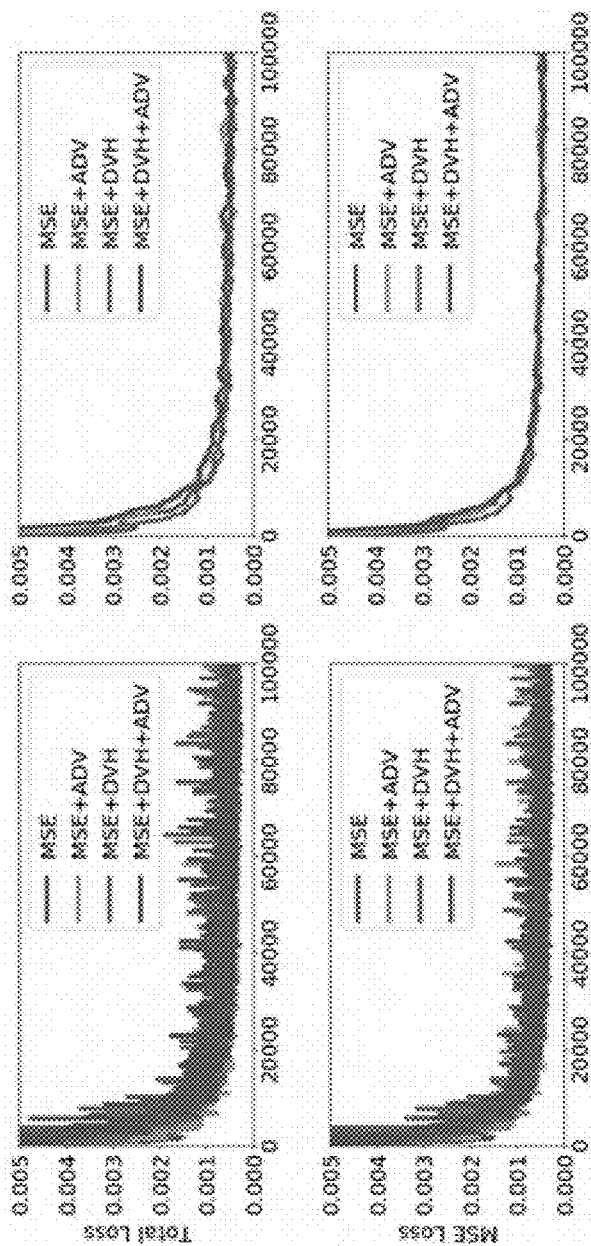
FIG. 43 are charts illustrating total validation loss (upper) and mean square error validation loss (lower), according to example embodiments.

FIG. 43 shows the validation losses for each model. The top row shows the total validation loss, while the bottom row shows just the mean squared error loss. Overall the loss curve had flattened by the end of the 100,000 iterations, indicating that each model converged. The final instances of the models chosen for evaluation were the models that performed the best on their respective total validation loss. Each model has achieved similar MSE losses, with the chosen models having their MSE validation losses at $2.46\times10^{-4}$ (MSE), $2.40\times10^{-4}$ (MSE+ADV), $2.26\times10^{-4}$ (MSE+DVH), $2.5\times10^{-4}$ (MSE+DVH+ADV).

Figure 44:
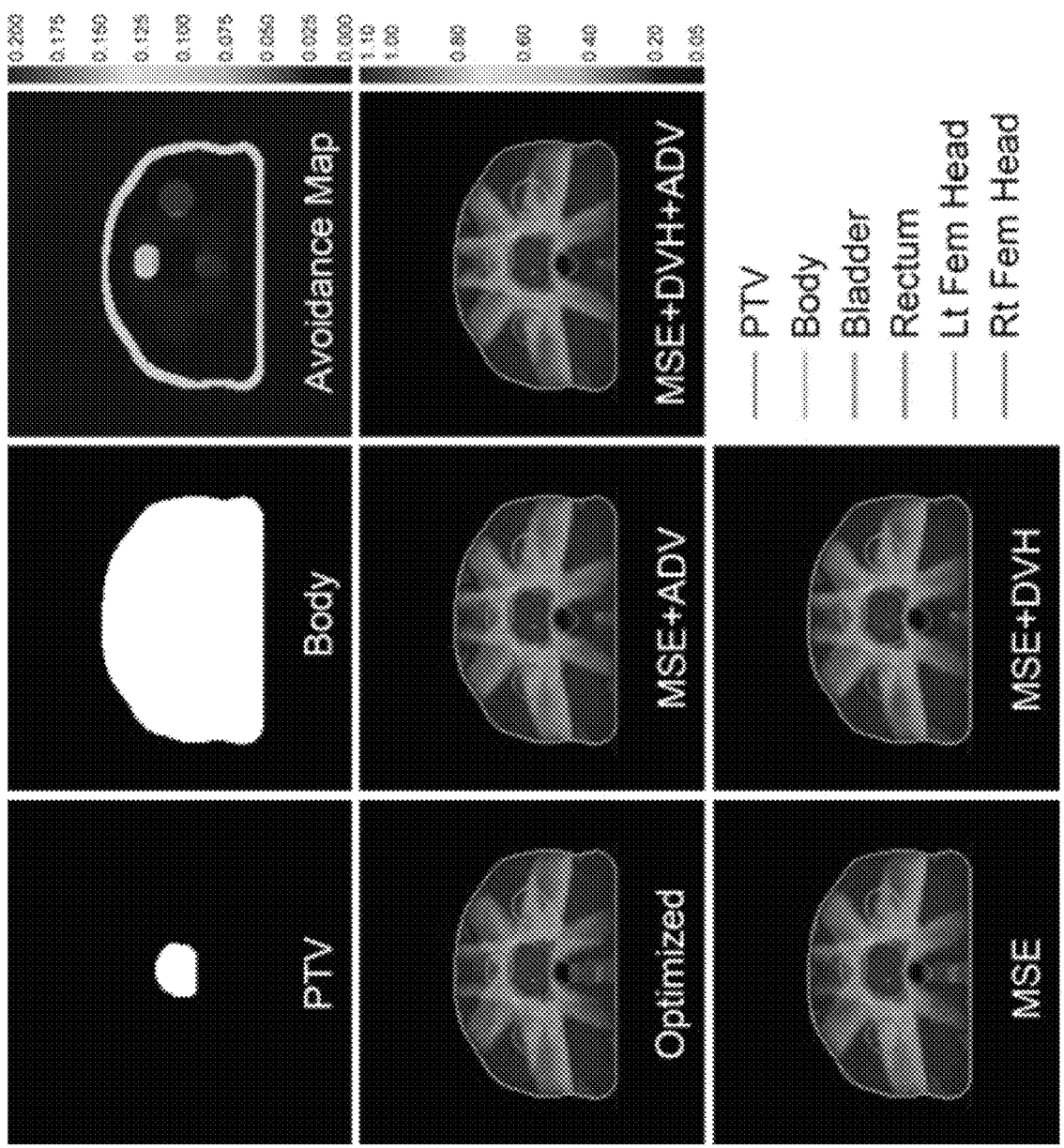
FIG. 44 is a block diagram illustrating input and predictions for a test patient and a rectum sparing plan, according to example embodiments.

FIG. 44 shows a comparison of the predictions between each of the 4 models in the study. The avoidance map is a sum of the critical structures, including a ring and skin tuning structure, with their assigned tradeoff weights. Visually, with the same input, each model produces a strikingly similar dose distribution. The MSE model visually did slightly better in sparing the dose in the normal tissue region posterior of the rectum.

Figure 45:
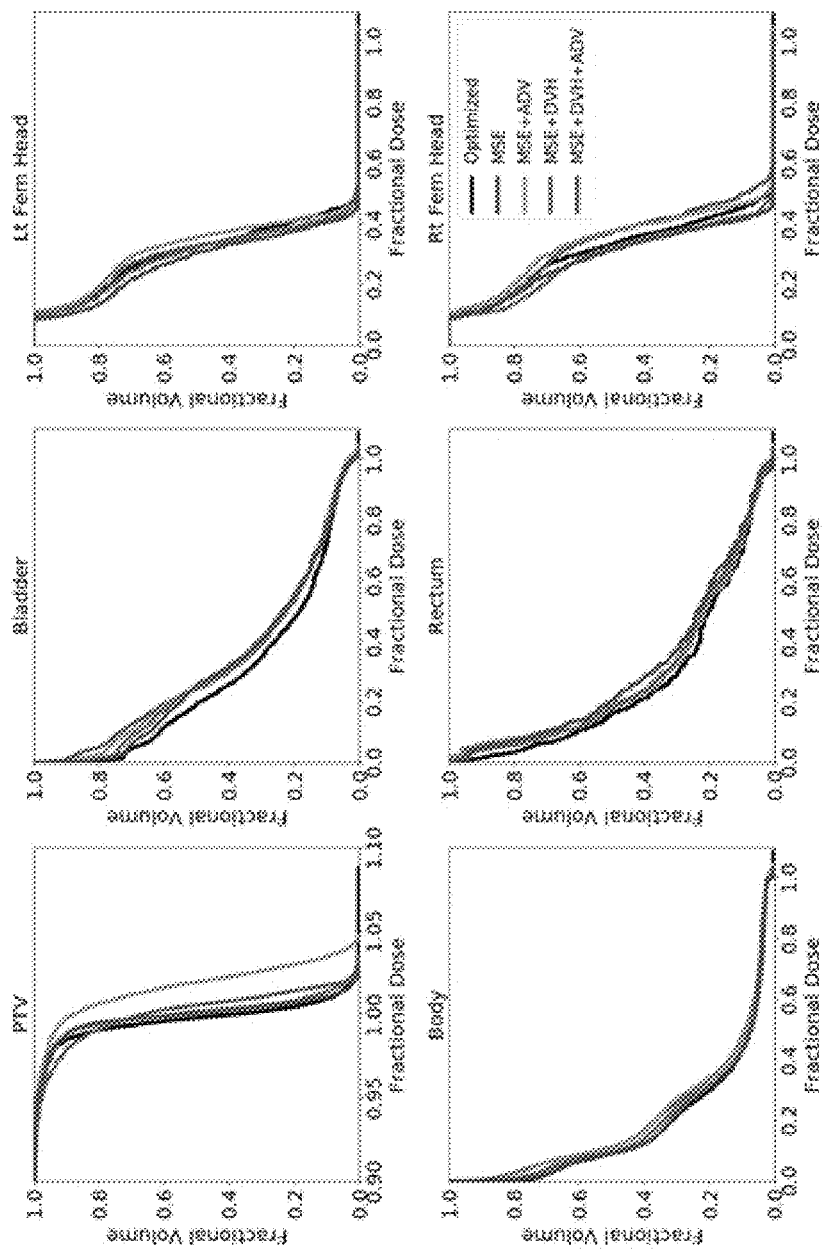
FIG. 45 is a block diagram illustrating dose volume histograms of optimized dose distribution and predicted dose distributions for the same patient, according to example embodiments.

The DVHs of the dose predictions are more revealing to the dose prediction errors in a clinically relevant manner, shown in FIG. 45. The two models involving DVH loss (red and green) have less error in predicting the dose in the PTV, Body, and Bladder, with respect to its DVH, and visually similar predictions for the remaining OARs. Overall, including the domain specific DVH based loss has overall improved the model's dose prediction in regards to the structure's DVH.

Figure 46:
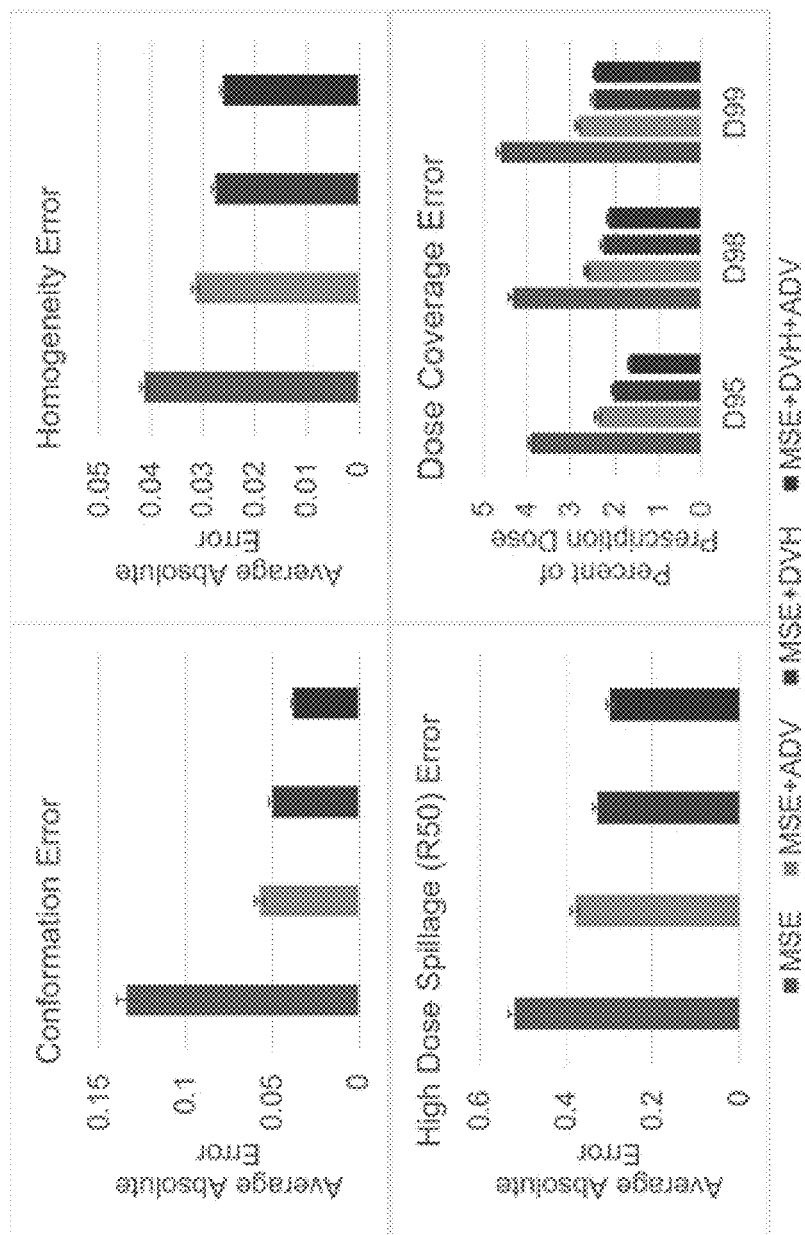
FIG. 46 is block diagram illustrating prediction errors for conformation, homogeneity, high dose spillage, and dose coverage, respectively, according to example embodiments.

FIG. 46 shows the errors for several clinical metrics calculated from the predicted dose distributions, as compared to that of the optimized dose. The MSE model had the largest prediction error of 0.134 (conformation), 0.041 (homogeneity), 0.520 (R50), 3.91% (D95), 4.33% (D98), 4.60% (D99). The additional adversarial and DVH losses further improved the prediction error, with the MSE+DVH+ADV model having the lowest prediction error of 0.038 (conformation), 0.026 (homogeneity), 0.298 (R50), 1.65% (D95), 2.14% (D98), 2.43% (D99). The other two models, MSE+ADV and MSE+DVH, had errors that were betweent the other two, with the MSE+DVH model's having less error than MSE+ADV. In terms of these dosimetric criteria, including the DVH loss has the best performance, even more than just including adversarial loss.

Figure 47:
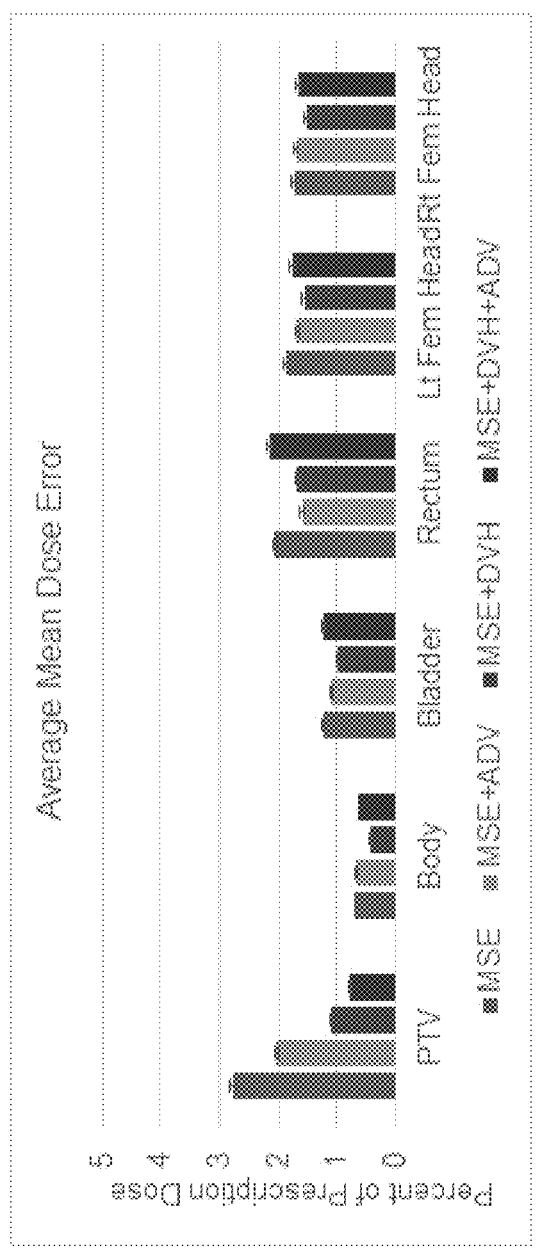
FIG. 47 is a chart illustrating average dose error in the mean dose for planning target volume and organs at risk, according to example embodiments.
Figure 48:
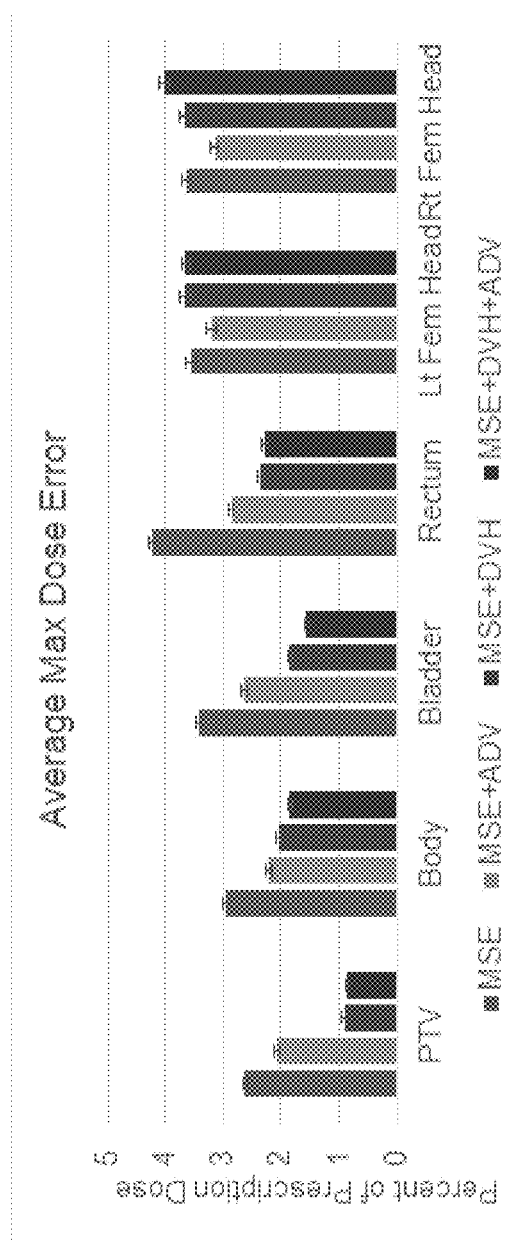
FIG. 48 is a chart illustrating average error in the max dose for planning target volume and organs at risk, according to example embodiments.

For both the mean dose PTV error and the max dose PTV, Body, Bladder and rectum error, the same improving trend can be observed in the order of the MSE model, MSE+ADV model, MSE+DVH model, and MSE+DVH+ADV model shown in FIG. 47 and FIG. 48. However, there is not a clear trend in the mean dose for the OARs, due to the fact that MSE is already designed for reducing average errors, making it competitive for the mean dose error performance There also lacks a trend for the max dose point for the femoral heads, which are further away from the PTV and are in the lower dose region that has higher variability in the dose distribution. All predictions have very low average mean and max dose errors of less than 2.8% and 4.2%, respectively.

VI.4: Discussion

This is the first usage of a domain specific loss function, the DVH loss, for volumetric dose distribution prediction in radiation therapy. The system may compare the performance of deep neural networks trained using various loss combinations, including MSE loss, MSE+ADV loss, MSE+DVH loss, and MSE+DVH+ADV. Inclusion of the DVH loss had improved the model's prediction in almost every aspect, except for mean dose to the OARs and the max dose the femurs. The DVH loss does not directly represent mean or max dose, and thus is not directly minimizing these aspects. In addition, MSE loss is inherently designed to minimize average error, thus it is not surprising that MSE loss alone is competitive for driving the organ mean dose error down, since the additional DVH and ADV losses may have the model focus on aspects other than mean error. Regardless of the model, all predictions have an average mean and max dose error less than 2.8% and 4.2%, respectively, of the prescription dose for every structure of interest.

Overall, the MSE+DVH+ADV performed the best in most of the categories, particularly the conformity, heterogeneity, high dose spillage, and planning target volume (PTV) dose coverage. This illustrates the importance of both human and learned domain knowledge. Expert human domain specific knowledge can greatly improve the performance of the model, tailoring the prediction towards domain relevant aspects. However, by having to explicit formulate this domain knowledge into an equation, it is difficult to capture the nuanced aspects of the problem. Using adversarial learning can then be used to further augment the model's performance, since the discriminator network can pick out the subtle aspects that the domain specific formulation may have missed.

Due to the non-convexity of both the DVH and ADV losses, as well as the inherent non-convex nature of neural networks, the MSE loss was utilized in every variant of the study, acting as the initial driving force and guide for the model to reasonably converge before the DVH and/or ADV losses began to take effect on the model's prediction. MSE loss still has many desirable properties from an optimization perspective. It is convex and has an extremely well behaved gradient. In addition the properties of the squared $l_2$-norm, where $$\ell_p(x) = \sqrt[p]{\sum_i |x|^p},$$

is one of the most understood and utilized functions in optimization (Boyd and Vandenberghe, 2009). It is not surprising that the previous studies achieved the state-of-the-art performance for dose prediction utilizing only MSE loss.

The final errors were assessed with 12,000 plans from 10 test patients, with varying tradeoff combinations. The total large number of plans with the randomization scheme given in Table 1 provides evidence that the entire tradeoff space has been reasonably sampled. The low prediction errors signify that the model is capable of reliably generating Pareto optimal dose distributions with high accuracy. In addition, the raw prediction time of the neural network, including data movement to and from the GPU, is at 0.052 seconds. Realistically, with data loading, prediction, DVH calculation, and displaying the dose wash to a user, it takes approximately 0.6 seconds. This is still fast enough for real time interaction with the model to quickly explore the tradeoff space for a patient. This thus provides a tool for empowering physicians Immediately after segmentation of the cancer patient, the physician can immediately begin to generate a dose distribution with realistic and patient-specific tradeoffs between the PTV and various OARs. Not only does this give the physician a sense of the available and achievable tradeoffs, the resulting dose can then be given to a dosimetrist as an a tangible and physician-preferred endpoint, alongside the other typical planning information provided by the physician. Usage of such a model is expected to drastically reduce the treatment planning time by reducing the number of feedback loops between the physician and dosimetrist, as well as how much the dosimetrist has to iterate though tuning hyperparameters in the fluence map optimization.

The addition of the adversarial loss increases the training time the most for training, since the discriminator has to be trained concurrently. The additional DVH loss does slow down the training as well, but has a much smaller effect than the adversarial loss. While the training times were wildly different, the final trained neural networks all yield the same exact prediction time, due to the fact that they have identical network architectures. The network that took the longest training time, MSE+DVH+ADV, took just under 4 days to train, which is still a very reasonable training time to prepare a model.

While this study was primarily focused on the evaluation of the DVH, ADV, and MSE losses, the final trained models do have their limitations. While these models are capable of generating dose distributions on the Pareto surface, it is currently limited to prostate cancer patients with 7 beam IMRT. In addition, the predicted dose distributions are not guaranteed to be deliverable, hence the current need for heavier dosimetrist involvement in the treatment planning VI.5: Conclusion In this study, a novel domain specific loss function, the dose volume histogram (DVH) loss, and evaluated its efficacy alongside two other losses, mean squared error (MSE) loss and adversarial (ADV) loss is provided herein. The system trained and evaluated four instances of the models with varying loss combinations, which included 1) MSE, 2) MSE+ADV, 3) MSE+DVH, 4) MSE+DVH+ADV. The models that included the domain specific DVH loss outperformed the models without the DVH loss in most of the categories, particularly on the evaluations of conformity, heterogeneity, high dose spillage, and planning target volume (PTV) dose coverage. The MSE+DVH+ADV model performed the best in these categories, illustrating the importance of both human and learned domain knowledge. Expert human domain specific knowledge can be the largest driver in the performance improvement, but it is difficult to capture nuanced aspects of the problem in an explicit formulation. Adversarial learning can be used to further capture these particular subtle attributes as part of the loss. The prediction of Pareto optimal doses can be performed in real-time, allowing for a physician to quickly navigate the tradeoff space for a patient, and produce a dose distribution as a tangible endpoint for the dosimetrist to use for planning.

Figure 49A:
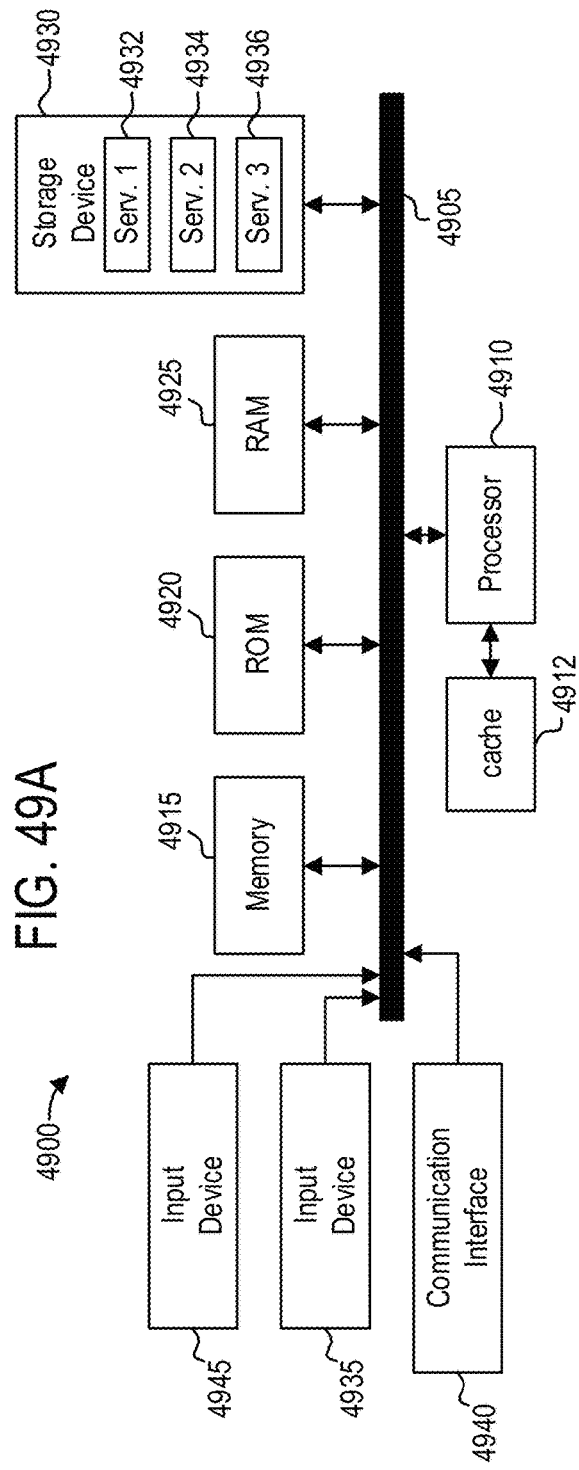
FIG. 49A is a block diagram illustrating a computing device, according to example embodiments.

FIG. 49A illustrates a system bus computing system architecture 4900, according to example embodiments. System 4900 may be representative of a computing system capable of performing the functions described above. One or more components of system 4900 may be in electrical communication with each other using a bus 4905. System 4900 may include a processing unit (CPU or processor) 4910 and a system bus 4905 that couples various system components including the system memory 4915, such as read only memory (ROM) 4920 and random access memory (RAM) 4925, to processor 4910. System 4900 may include a cache of high-speed memory connected directly with, in close proximity to, or integrated as part of processor 4910. System 4900 may copy data from memory 4915 and/or storage device 4930 to cache 4912 for quick access by processor 4910. In this way, cache 4912 may provide a performance boost that avoids processor 4910 delays while waiting for data. These and other modules may control or be configured to control processor 4910 to perform various actions. Other system memory 4915 may be available for use as well. Memory 4915 may include multiple different types of memory with different performance characteristics. Processor 4910 may include any general purpose processor and a hardware module or software module, such as service 1 4932, service 2 4934, and service 3 4936 stored in storage device 4930, configured to control processor 4910 as well as a special-purpose processor where software instructions are incorporated into the actual processor design. Processor 4910 may essentially be a completely self-contained computing system, containing multiple cores or processors, a bus, memory controller, cache, etc. A multi-core processor may be symmetric or asymmetric.

To enable user interaction with the computing device 4900, an input device 4945 may represent any number of input mechanisms, such as a microphone for speech, a touch-sensitive screen for gesture or graphical input, keyboard, mouse, motion input, speech and so forth. An output device 4935 may also be one or more of a number of output mechanisms known to those of skill in the art. In some instances, multimodal systems may enable a user to provide multiple types of input to communicate with computing device 4900. Communications interface 4940 may generally govern and manage the user input and system output. There is no restriction on operating on any particular hardware arrangement and therefore the basic features here may easily be substituted for improved hardware or firmware arrangements as they are developed.

Storage device 4930 may be a non-volatile memory and may be a hard disk or other types of computer readable media which may store data that are accessible by a computer, such as magnetic cassettes, flash memory cards, solid state memory devices, digital versatile disks, cartridges, random access memories (RAMs) 4925, read only memory (ROM) 4920, and hybrids thereof.

Storage device 4930 may include services 4932, 4934, and 4936 for controlling the processor 4910. Other hardware or software modules are contemplated. Storage device 4930 may be connected to system bus 4905. In one aspect, a hardware module that performs a particular function may include the software component stored in a computer-readable medium in connection with the necessary hardware components, such as processor 4910, bus 4905, display 4935, and so forth, to carry out the function.

Figure 49B:
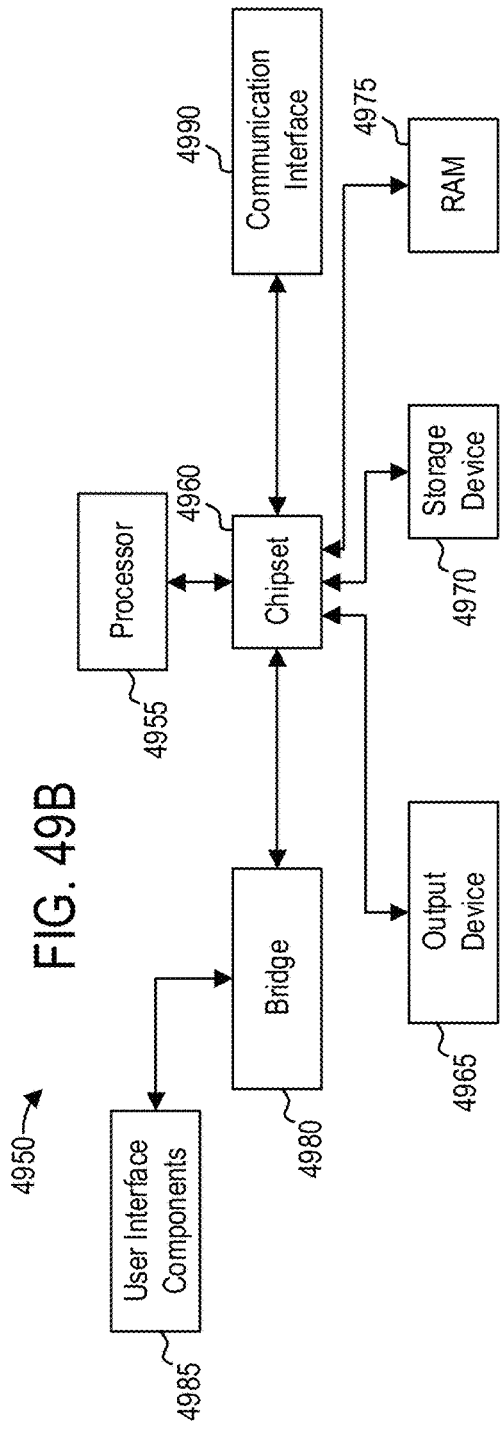
FIG. 49B is a block diagram illustrating a computing device, according to example embodiments.

FIG. 49B illustrates a computer system 4950 having a chipset architecture. Computer system 4950 may be an example of computer hardware, software, and firmware that may be used to implement the disclosed technology. System 4950 may include a processor 4955, representative of any number of physically and/or logically distinct resources capable of executing software, firmware, and hardware configured to perform identified computations. Processor 4955 may communicate with a chipset 4960 that may control input to and output from processor 4955. In this example, chipset 4960 outputs information to output 4965, such as a display, and may read and write information to storage device 4970, which may include magnetic media, and solid state media, for example. Chipset 4960 may also read data from and write data to RAM 4975. A bridge 4980 for interfacing with a variety of user interface components 4985 may be provided for interfacing with chipset 4960. Such user interface components 4985 may include a keyboard, a microphone, touch detection and processing circuitry, a pointing device, such as a mouse, and so on. In general, inputs to system 4950 may come from any of a variety of sources, machine generated and/or human generated.

Chipset 4960 may also interface with one or more communication interfaces 4990 that may have different physical interfaces. Such communication interfaces may include interfaces for wired and wireless local area networks, for broadband wireless networks, as well as personal area networks. Some applications of the methods for generating, displaying, and using the GUI disclosed herein may include receiving ordered datasets over the physical interface or be generated by the machine itself by processor 4955 analyzing data stored n storage 4970 or 4975. Further, the machine may receive inputs from a user through user interface components 4985 and execute appropriate functions, such as browsing functions by interpreting these inputs using processor 4955.

It may be appreciated that example systems 4900 and 4950 may have more than one processor 4910 or be part of a group or cluster of computing devices networked together to provide greater processing capability.

While the foregoing is directed to embodiments described herein, other and further embodiments may be devised without departing from the basic scope thereof. For example, aspects of the present disclosure may be implemented in hardware or software or a combination of hardware and software. One embodiment described herein may be implemented as a program product for use with a computer system. The program(s) of the program product define functions of the embodiments (including the methods described herein) and can be contained on a variety of computer-readable storage media. Illustrative computer-readable storage media include, but are not limited to: (i) non-writable storage media (e.g., read-only memory (ROM) devices within a computer, such as CD-ROM disks readably by a CD-ROM drive, flash memory, ROM chips, or any type of solid-state non-volatile memory) on which information is permanently stored; and (ii) writable storage media (e.g., floppy disks within a diskette drive or hard-disk drive or any type of solid state random-access memory) on which alterable information is stored. Such computer-readable storage media, when carrying computer-readable instructions that direct the functions of the disclosed embodiments, are embodiments of the present disclosure.

It will be appreciated to those skilled in the art that the preceding examples are exemplary and not limiting. It is intended that all permutations, enhancements, equivalents, and improvements thereto are apparent to those skilled in the art upon a reading of the specification and a study of the drawings are included within the true spirit and scope of the present disclosure. It is therefore intended that the following appended claims include all such modifications, permutations, and equivalents as fall within the true spirit and scope of these teachings.

All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed. The article by Dan Nguyen, Xun Jia, David Sher, Mu-Han Lin, Zohaib Iqbal, Hui Liu, Steve Jiang, entitled "Three-Dimensional Radiotherapy Dose Prediction on Head and Neck Cancer Patients with a Hierarchically Densely Connected U-net Deep Learning Architecture," arXiv:1805.10397 [physics.med-ph], May 25, 2018, and Physics in Medicine & Biology 64, 065020, doi: 10.1088/1361-6560/ab039b, Mar. 18, 2019, is hereby incorporated by reference for all purposes. The reference by Dan Nguyen, Troy Long, Xun Jia, Weiguo Lu, Xuejun Gu, Zohaib Iqbal, Steve Jiang, entitled "Dose Prediction with U-net: A Feasibility Study for Predicting Dose Distributions from Contours using Deep Learning on Prostate IMRT Patients," arXiv:1709.09233v3 [physics.med-ph], May 23, 2018, and Scientific Reports 9, 1076, Jan. 31, 2019, is hereby incorporated by reference. The reference by Ana M. Barragan-Montero, Dan Nguyen, Weiguo Lu, Mu-Han Lin, Xavier Geets, Edmond Sterpin, Steve Jiang, entitled "Three-Dimensional Dose Prediction for Lung IMRT Patients with Deep Neural Networks: Robust Learning from Heterogeneous Beam Configurations," arXiv:1812.06934 [physics.med-ph], Dec. 17, 2018, and Medical Physics 6(8):3679-3691 mp.13597, May 18, 2019, is hereby incorporated by reference. The reference by Dan Nguyen, Azar Sadeghnejad Barkousaraie, Chenyang Shen, Xun Jia, Steve Jiang, entitled "Generating Pareto optimal dose distributions for radiation therapy treatment planning," arXiv:1906.04778 [physics.med-ph], Jun. 11, 2019, is hereby incorporated by reference. The reference by Dan Nguyen, Rafe McBeth, Azar Sadeghnejad Barkousaraie, Gyanendra Bohara, Chenyang Shen, Xun Jia, and Steve Jiang, entitled "Incorporating human and learned domain knowledge into training deep neural networks: A differentiable dose volume histogram and adversarial inspired framework for generating Pareto optimal dose distributions in radiation therapy," Aug. 16, 2019, is hereby incorporated by reference.

What is claimed is:

1. A method for generating a treatment plan, comprising:
receiving, by a computing system, a plurality of dose volume histograms for a plurality of patients and a plurality of volumetric dose distributions corresponding to the plurality of dose volume histograms;
generating, by the computing system, a volumetric dose prediction model using a deep learning network comprising a hierarchically densely connected U-net by:
learning, by the deep learning network, a relationship between the plurality of dose volume histograms for the plurality of patients and the corresponding plurality of volumetric dose distributions;
receiving, by the computing system, a candidate dose volume histogram for a target patient;
inferring, by the computing system via the volumetric dose prediction model, a volumetric dose prediction distribution matching the candidate dose volume histogram; and
generating, by the computing system, a treatment plan based on the inferred volumetric dose prediction distribution.

2. The method of claim 1, wherein the deep learning network comprises a dense convolution portion, a dense downsampling portion, and u-net upsampling portion.

3. The method of claim 1, wherein the treatment plan is for one of head and neck cancer, lung cancer, and prostate cancer.

4. The method of claim 1, wherein receiving, by the computing system, the plurality of dose volume histograms for the plurality of patients and the plurality of volumetric dose distributions corresponding to the plurality of dose volume histograms comprises:
contour information for an organ-at-risk.

5. The method of claim 4, wherein receiving, by the computing system, the candidate dose volume histogram for the target patient comprises:
receiving the contour information for a target organ-at-risk.

6. The method of claim 1, further comprising:
receiving, at the computing system, a request for a new prediction, the request comprising a tuning of parameters associated with the treatment plan; and
generating, by the computing system via the volumetric dose prediction model, a new treatment plan based on the tuning of the parameters.

7. The method of claim 1, wherein the treatment plan comprises a Pareto surface recommendation generated in real-time.

8. A system, comprising:
a processor; and
a memory having programming instructions stored thereon, which, when executed by the processor, performs one or more operations comprising:
receiving a plurality of dose volume histograms for a plurality of patients and a plurality of volumetric dose distributions corresponding to the plurality of dose volume histograms;
generating a volumetric dose prediction model using a deep learning network comprising a hierarchically densely connected U-net by:
learning, by the deep learning network, a relationship between the plurality of dose volume histograms for the plurality of patients and the corresponding plurality of volumetric dose distributions;
receiving a candidate dose volume histogram for a target patient;
inferring, by the volumetric dose prediction model, a volumetric dose prediction distribution matching the candidate dose volume histogram; and
generating a treatment plan based on the inferred volumetric dose prediction distribution.

9. The system of claim 8, wherein the neural deep learning network comprises a dense convolution portion, a dense downsampling portion, and u-net upsampling portion.

10. The system of claim 8, wherein the treatment plan is for one of head and neck cancer, lung cancer, and prostate cancer.

11. The system of claim 8, wherein receiving the plurality of dose volume histograms for the plurality of patients and the plurality of volumetric dose distributions corresponding to the plurality of dose volume histograms comprises:
contour information for an organ-at-risk.

12. The system of claim 11, wherein receiving the candidate dose volume histogram for the target patient comprises:
receiving the contour information for a target organ-at-risk.

13. The system of claim 8, wherein the one or more operations further comprise:
receiving a request for a new prediction, the request comprising a tuning of parameters associated with the treatment plan; and
generating, via the volumetric dose prediction model, a new treatment plan based on the tuning of the parameters.

14. The system of claim 8, wherein the treatment plan is a Pareto surface recommendation generated in real-time.

15. A non-transitory computer readable medium having instructions stored thereon, which, when executed by a processor, cause the processor to perform an operation, comprising:
receiving, by a computing system, a plurality of dose volume histograms for a plurality of patients and a plurality of volumetric dose distributions corresponding to the plurality of dose volume histograms;

generating, by the computing system, a volumetric dose prediction model using a deep learning network comprising a hierarchically densely connected U-net by:
  learning, by the deep learning network, a relationship between the plurality of dose volume histograms for the plurality of patients and the corresponding plurality of volumetric dose distributions;
receiving, by the computing system, a candidate dose volume histogram for a target patient;
inferring, by the computing system via the volumetric dose prediction model, a volumetric dose prediction distribution matching the candidate dose volume histogram; and
generating, by the computing system, a treatment plan based on the inferred volumetric dose prediction distribution.

16. The non-transitory computer readable medium of claim 15, wherein the deep learning network comprises a dense convolution portion, a dense downsampling portion, and u-net upsampling portion.

17. The non-transitory computer readable medium of claim 15, wherein the treatment plan is for one of head and neck cancer, lung cancer, and prostate cancer.

18. The non-transitory computer readable medium of claim 15, wherein receiving, by the computing system, the plurality of dose volume histograms for the plurality of patients and the plurality of volumetric dose distributions corresponding to the plurality of dose volume histograms comprises:
  contour information for an organ-at-risk.

19. The non-transitory computer readable medium of claim 18, wherein receiving, by the computing system, the candidate dose volume histogram for the target patient comprises:
  receiving the contour information for a target organ-at-risk.

20. The non-transitory computer readable medium of claim 15, further comprising:
  receiving, at the computing system, a request for a new prediction, the request comprising a tuning of parameters associated with the treatment plan; and
  generating, by the computing system via the volumetric dose prediction model, a new treatment plan based on the tuning of the parameters.

* * * * *